US012214156B2

(12) United States Patent
Ben-David et al.

(10) Patent No.: US 12,214,156 B2
(45) Date of Patent: Feb. 4, 2025

(54) SYSTEMS, METHODS, APPARATUSES AND DEVICES FOR DRUG OR SUBSTANCE DELIVERY

(71) Applicant: Triple Jump Israel Ltd., Yokneam Illit (IL)

(72) Inventors: Yishai Ben-David, Givat Ela (IL); Kfir Solomon, Modi'in (IL); Ofer Yodfat, Modi'in (IL); Guy Shinar, Givatayim (IL)

(73) Assignee: TRIPLE JUMP ISRAEL LTD., Yokneam Illit (IL)

( * ) Notice: Subject to any disclaimer, the term of this patent is extended or adjusted under 35 U.S.C. 154(b) by 1041 days.

(21) Appl. No.: 16/643,218

(22) PCT Filed: Aug. 28, 2018

(86) PCT No.: PCT/IL2018/050952
§ 371 (c)(1),
(2) Date: Feb. 28, 2020

(87) PCT Pub. No.: WO2019/043702
PCT Pub. Date: Mar. 7, 2019

(65) Prior Publication Data
US 2020/0345929 A1 Nov. 5, 2020

Related U.S. Application Data

(60) Provisional application No. 62/599,493, filed on Dec. 15, 2017, provisional application No. 62/572,887, (Continued)

(51) Int. Cl.
*A61M 5/142* (2006.01)
*A61M 5/145* (2006.01)
*A61M 5/172* (2006.01)

(52) U.S. Cl.
CPC ...... *A61M 5/14248* (2013.01); *A61M 5/1456* (2013.01); *A61M 5/1723* (2013.01);
(Continued)

(58) Field of Classification Search
CPC ............ A61M 5/14248; A61M 5/1452; A61M 5/1456; A61M 5/1723; A61M 2005/14252; A61M 2005/14208; A61M 2005/1585
See application file for complete search history.

(56) References Cited

U.S. PATENT DOCUMENTS 4,306,976 A 12/1981 Bazzato
5,092,856 A 3/1992 Johnston
(Continued)

FOREIGN PATENT DOCUMENTS

CN 1471413 A 1/2004
CN 1874809 A 12/2006
(Continued)

OTHER PUBLICATIONS

Extended European Search Report for European Application No. EP22184226.3 dated Jan. 23, 2023, 8 Pages.
(Continued)

*Primary Examiner* — Laura A Bouchelle
(74) *Attorney, Agent, or Firm* — COOLEY LLP

(57) ABSTRACT

Embodiments of the present disclosure are directed to miniature insulin patch pump, assistance devices (e.g., for reservoir filling and/or cannula insertion), and methods related thereto. For example, in some embodiments, a substance/drug-delivery patch pump is provided and includes a reusable part (RP) including a power source, a driving mechanism, and an electronic module, and a disposable part
(Continued)

(DP), where the disposable part can include at least a plurality of an adhesive base, a reservoir, a dosing mechanism, and a cannula.

21 Claims, 55 Drawing Sheets

Related U.S. Application Data filed on Oct. 16, 2017, provisional application No. 62/551,082, filed on Aug. 28, 2017.

(52) U.S. Cl.
CPC ............ *A61M 2005/14208* (2013.01); *A61M 2005/14252* (2013.01); *A61M 2202/0486* (2013.01); *A61M 2205/273* (2013.01)

(56) References Cited

U.S. PATENT DOCUMENTS

| | | | |
|---|---|---|---|
| 5,135,485 | A | 8/1992 | Cohen et al. |
| 5,803,712 | A | 9/1998 | Davis et al. |
| 6,485,461 | B1 | 11/2002 | Mason et al. |
| 8,262,617 | B2 | 9/2012 | Aeschlimann et al. |
| 8,277,415 | B2 | 10/2012 | Mounce et al. |
| 8,529,513 | B2 | 9/2013 | Peter et al. |
| 8,573,027 | B2 | 11/2013 | Rosinko et al. |
| 9,227,010 | B2 | 1/2016 | Neta et al. |
| 9,250,106 | B2 | 2/2016 | Rosinko et al. |
| 9,314,564 | B2 | 4/2016 | Imhof et al. |
| 9,364,185 | B2 | 6/2016 | Strickland |
| 9,415,158 | B2 | 8/2016 | Miller et al. |
| 9,750,873 | B2 | 9/2017 | Brown et al. |
| 9,798,859 | B2 | 10/2017 | Yodfat et al. |
| 9,942,091 | B2 | 4/2018 | Harvey et al. |
| 10,010,674 | B2 | 7/2018 | Rosinko et al. |
| 10,434,254 | B2 | 10/2019 | Imhof et al. |
| 10,438,696 | B2 | 10/2019 | Shapley et al. |
| 10,583,244 | B2 | 3/2020 | Yodfat et al. |
| 10,811,129 | B2 | 10/2020 | Bush et al. |
| 11,241,534 | B2 | 2/2022 | Miller et al. |
| 11,554,209 | B2 | 1/2023 | Yodfat et al. |
| 11,596,733 | B2 | 3/2023 | Yodfat et al. |
| 2005/0101912 | A1 | 5/2005 | Faust et al. |
| 2007/0088271 | A1 | 4/2007 | Richards |
| 2008/0255516 | A1 | 10/2008 | Yodfat et al. |
| 2009/0088694 | A1 | 4/2009 | Carter et al. |
| 2009/0099521 | A1 | 4/2009 | Gravesen et al. |
| 2009/0287180 | A1 | 11/2009 | Diperna |
| 2010/0008795 | A1 | 1/2010 | Diperna |
| 2010/0145303 | A1 | 6/2010 | Yodfat et al. |
| 2011/0054399 | A1 | 3/2011 | Chong et al. |
| 2011/0137255 | A1 | 6/2011 | Nielsen et al. |
| 2011/0196308 | A1 | 8/2011 | Kodgule et al. |
| 2012/0022453 | A1 | 1/2012 | Yodfat et al. |
| 2012/0192951 | A1 | 8/2012 | Yodfat et al. |
| 2013/0237955 | A1 | 9/2013 | Neta et al. |
| 2014/0039392 | A1 | 2/2014 | Geipel et al. |
| 2014/0135699 | A1 | 5/2014 | Gyory |
| 2015/0029816 | A1 | 1/2015 | Beyer et al. |
| 2015/0038906 | A1 | 2/2015 | Cane' |
| 2015/0157788 | A1 | 6/2015 | Gescheit et al. |
| 2015/0265765 | A1 | 9/2015 | Yavorsky et al. |
| 2015/0265768 | A1 | 9/2015 | Vazquez et al. |
| 2017/0246379 | A1 | 8/2017 | Kruse |
| 2019/0015582 | A1 | 1/2019 | Naftalovitz et al. |
| 2019/0099551 | A1 | 4/2019 | Yodfat et al. |
| 2019/0160258 | A1 | 5/2019 | Kristen |
| 2019/0321544 | A1 | 10/2019 | List |
| 2020/0013495 | A1 | 1/2020 | Torai |
| 2020/0179594 | A1 | 6/2020 | Yodfat et al. |
| 2020/0206417 | A1 | 7/2020 | Yodfat et al. |
| 2023/0256160 | A1 | 8/2023 | Yodfat et al. |
| 2024/0001028 | A1 | 1/2024 | Yodfat et al. |

FOREIGN PATENT DOCUMENTS

| | | |
|---|---|---|
| CN | 101563120 A | 10/2009 |
| CN | 101772359 A | 7/2010 |
| CN | 101808679 A | 8/2010 |
| CN | 102186515 A | 9/2011 |
| CN | 102596289 A | 7/2012 |
| CN | 102813976 A | 12/2012 |
| CN | 102985124 A | 3/2013 |
| CN | 103370007 A | 10/2013 |
| CN | 103442749 A | 12/2013 |
| CN | 203647799 U | 6/2014 |
| CN | 203815967 U | 9/2014 |
| CN | 104203311 A | 12/2014 |
| CN | 104474606 A | 4/2015 |
| CN | 104717991 A | 6/2015 |
| CN | 106659845 A | 5/2017 |
| DE | 3708857 A1 | 9/1988 |
| EP | 0236543 A1 | 9/1987 |
| EP | 1704886 A1 | 9/2006 |
| EP | 2295093 A2 | 3/2011 |
| EP | 2295098 A1 | 3/2011 |
| EP | 2365453 A2 | 9/2011 |
| EP | 2698178 A2 | 2/2014 |
| EP | 2719410 A2 | 4/2014 |
| EP | 2763064 A2 | 8/2014 |
| EP | 2919831 A1 | 9/2015 |
| EP | 3095255 A1 | 11/2016 |
| EP | 3284507 A1 | 2/2018 |
| EP | 3335745 A1 | 6/2018 |
| JP | S56116470 A | 9/1981 |
| JP | H0388547 U | 9/1991 |
| JP | 2002248168 A | 9/2002 |
| JP | 2006512114 A | 4/2006 |
| JP | 2011516097 A | 5/2011 |
| JP | 2012513786 A | 6/2012 |
| JP | 2013-503691 A | 2/2013 |
| JP | 2013503706 A | 2/2013 |
| JP | 2013-544161 A | 12/2013 |
| JP | 2014050686 A | 3/2014 |
| JP | 2014531922 A | 12/2014 |
| WO | WO-2004052725 A1 | 6/2004 |
| WO | WO 2007/108987 A2 | 9/2007 |
| WO | WO 2008/024808 A1 | 2/2008 |
| WO | WO 2008/122983 A1 | 10/2008 |
| WO | WO 2009/045779 A2 | 4/2009 |
| WO | WO-2010076275 A1 | 7/2010 |
| WO | WO-2011009224 A2 | 1/2011 |
| WO | WO-2011028846 A2 | 3/2011 |
| WO | WO-2013033421 A2 | 3/2013 |
| WO | WO 2016/145094 A2 | 9/2016 |
| WO | WO 2016/157638 A1 | 10/2016 |
| WO | WO 2016/181384 A2 | 11/2016 |
| WO | WO-2017060899 A2 | 4/2017 |
| WO | WO 2018/229783 A1 | 12/2018 |
| WO | WO 2019/043702 A1 | 3/2019 |

OTHER PUBLICATIONS

Office Action in Japanese Patent Application No. 2021-036270 dated Dec. 27, 2021, and English translation, 7 pages.
Extended European Search Report, dated Jan. 9, 2019, for European Application No. 16792303.6, 6 pages.
Extended European Search Report, dated Sep. 23, 2020, for European Application No. 18818197.8, 7 pages.
Extended European Search Report, dated Apr. 26, 2021, for European Application No. 18851689.2, 9 pages.
International Preliminary Report on Patentability, dated Dec. 17, 2019, for International Application No. PCT/IL2018/050668, 6 pages.
International Preliminary Report on Patentability, dated Nov. 14, 2018, for International Application No. PCT/IL2016/050481, 6 pages.
International Search Report and Written Opinion, dated Dec. 6, 2016, for International Application No. PCT/IL2016/050481, 9 pages.

(56) References Cited

OTHER PUBLICATIONS

International Search Report and Written Opinion, dated Dec. 6, 2018, for International Application No. PCT/IL2018/050668, 8 pages.
International Search Report and Written Opinion, dated Dec. 6, 2018, for International Application No. PCT/IL2018/050952, 9 pages.
International Preliminary Report on Patentability, dated Mar. 3, 2020, for International Application No. PCT/IL2018/050952, 7 pages.
Invitation to pay additional search fees, dated Sep. 20, 2016, for International Application No. PCT/IL2016/050481, 2 pages.

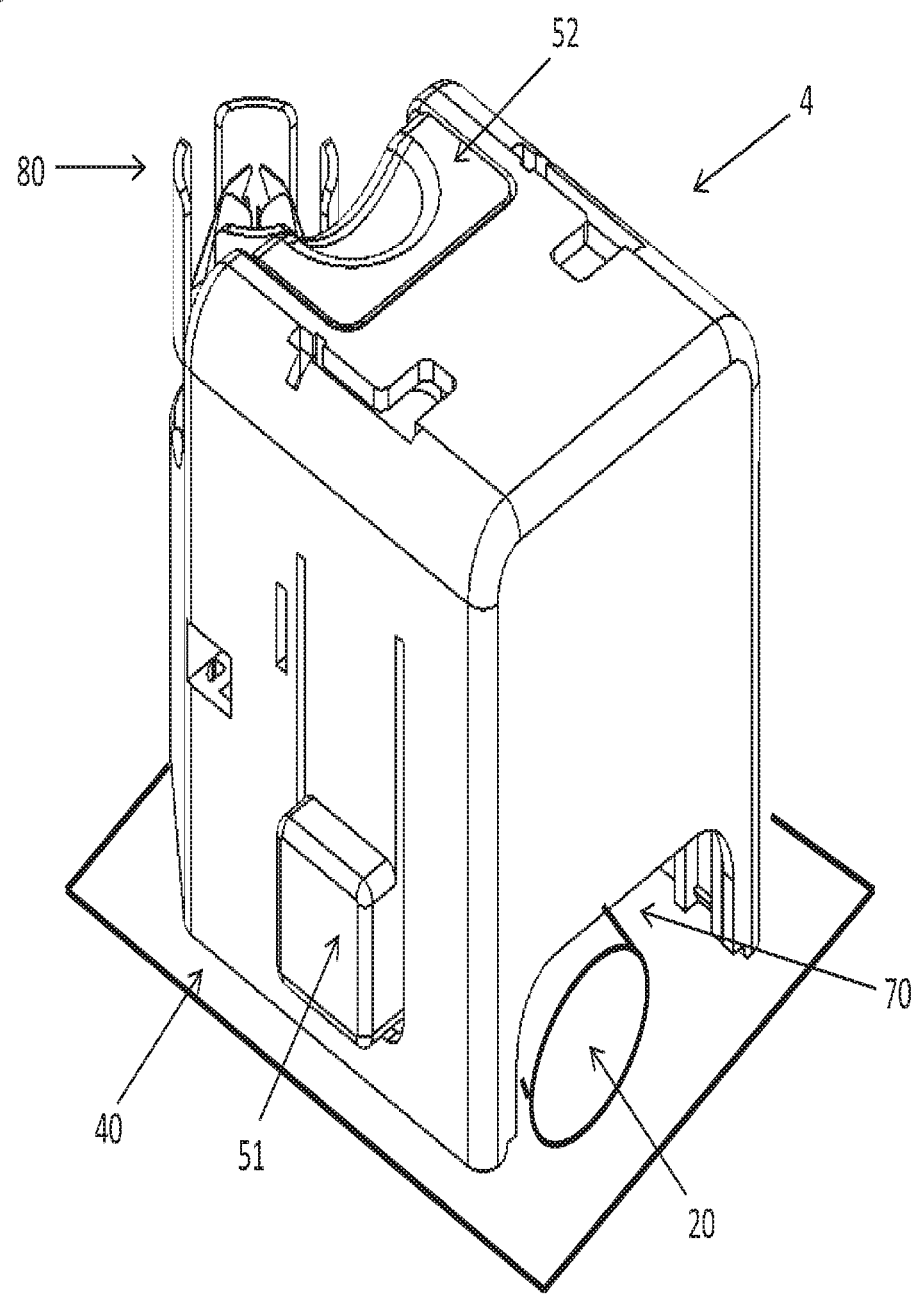

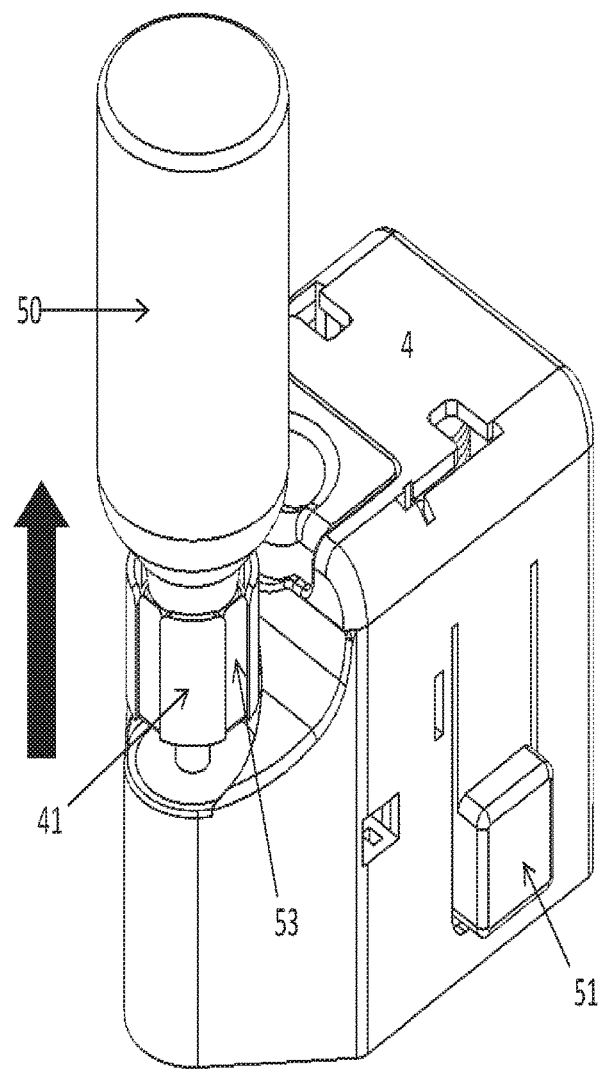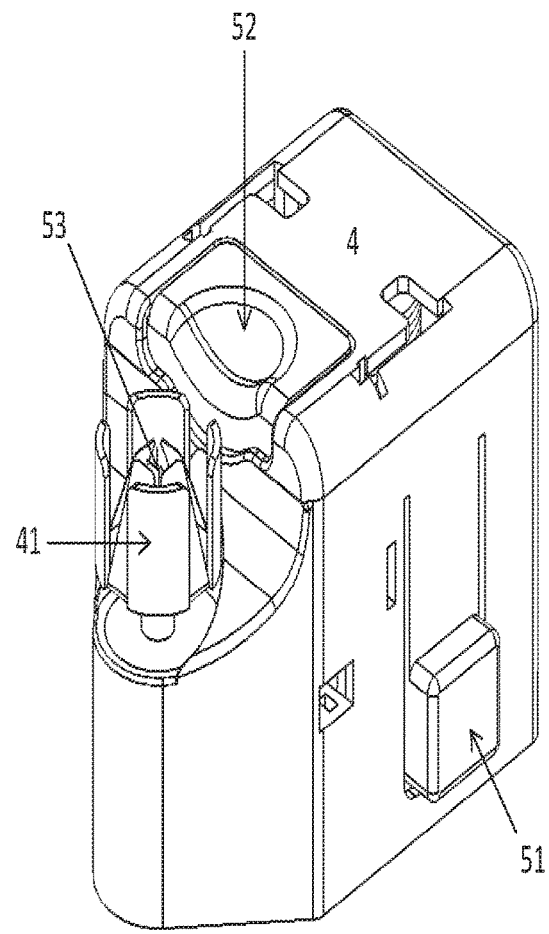

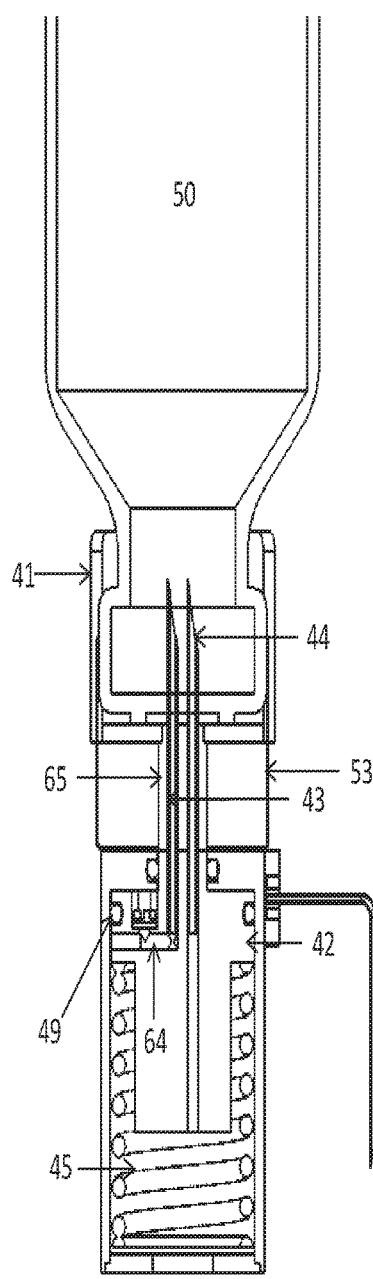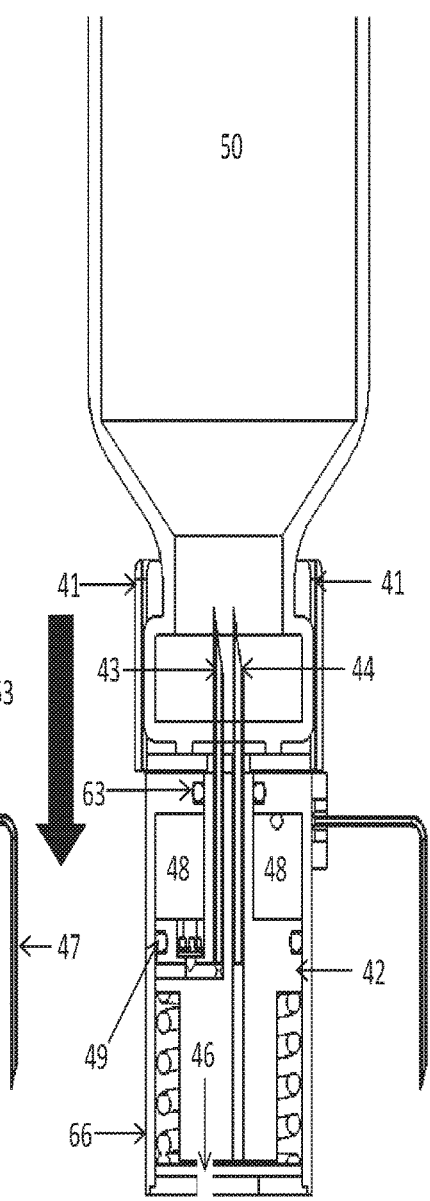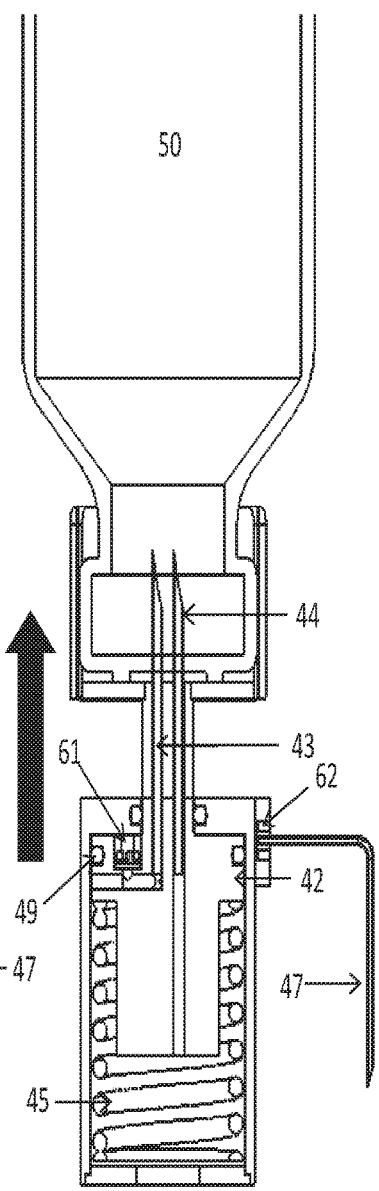

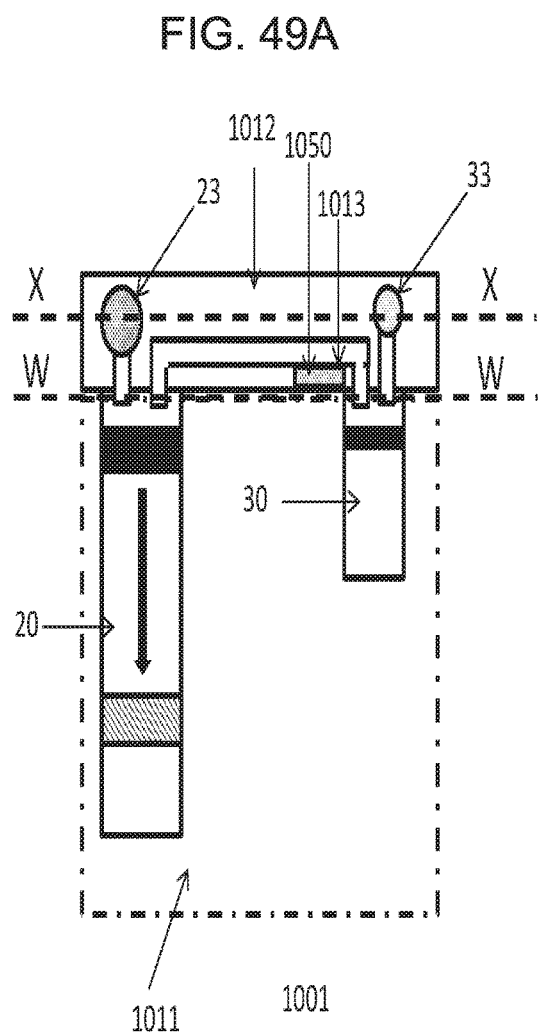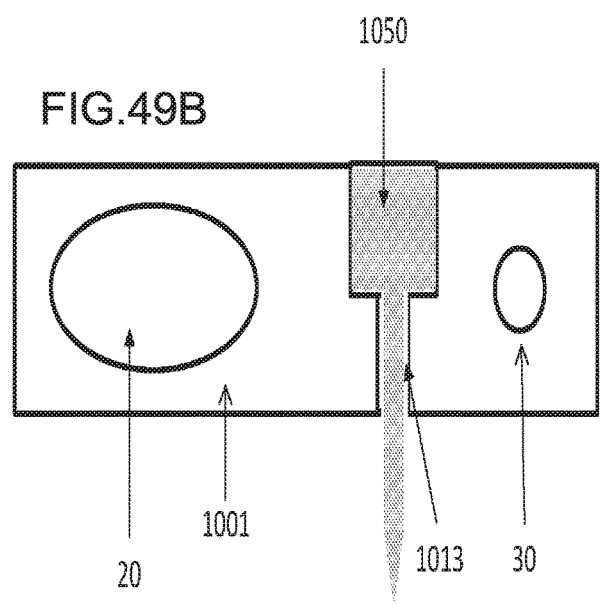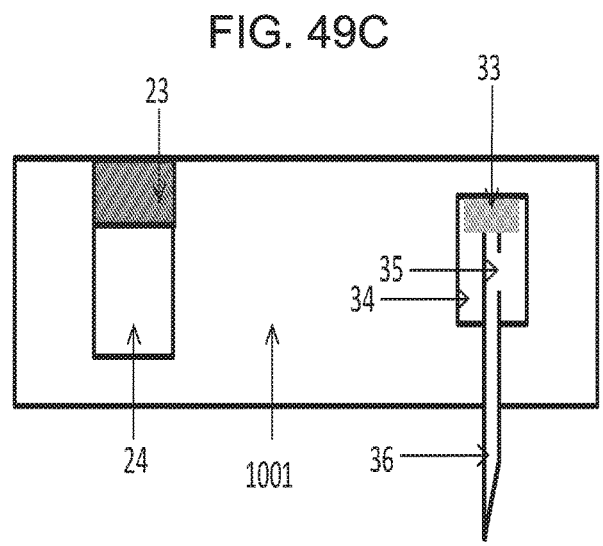

SYSTEMS, METHODS, APPARATUSES AND DEVICES FOR DRUG OR SUBSTANCE DELIVERY

RELATED APPLICATIONS

This application is a national stage entry of, and claims priority to, International Application No. PCT/IL2018/050952, filed Aug. 28, 2018, entitled "Systems, Methods, Apparatuses and Devices for Drug or Substance Delivery", which claims benefit of, and priority to, the following prior disclosures: U.S. provisional appln. No. 62/551,082, filed Aug. 28, 2017, entitled, "Systems, Methods, and Devices for Drug Delivery," U.S. provisional appln. No. 62/572,887, filed Oct. 16, 2017, entitled, "Systems, Methods, and Devices for Drug Delivery," and U.S. provisional appln. No. 62/599,493, filed Dec. 15, 2017, entitled, "Systems, Methods, and Devices for Drug Delivery." The application is also a continuation in part to PCT Appln. No. PCT/IL2018/050668, filed Jun. 15, 2018, entitled, "Patch Pump Systems and Apparatus for Managing Diabetes, and Methods thereof," which claims benefit of U.S. provisional application No. 62/519,982, filed Jun. 15, 2018, entitled "Patch Pump Systems and Apparatus for Managing Diabetes, and Methods Thereof." Each of these disclosures is herein incorporated by reference in their entireties.

FIELD OF THE DISCLOSURE

Embodiments of the present disclosure are directed at an insulin (or other substance) dispensing pump (e.g., a miniature pump, or patch pump), as well as an assistance device for at least one of reservoir filling and cannula insertion (for example).

BACKGROUND OF THE INVENTION

Diabetes mellitus patients require administration of varying amounts of insulin throughout the day to control their blood glucose levels. Ambulatory portable insulin infusion pumps can be used as superior alternatives to multiple daily syringe injections of insulin. However, although these devices represent an improvement over multiple daily injections, they nevertheless all suffer from several drawbacks. One drawback is the large size and weight of the devices, caused by the configuration and the relatively large size of the driving mechanism and syringe. These relatively bulky devices have to be regularly carried in a patient's pocket or attached to his/her belt. Inserting of cannulas for transcutaneous delivery of insulin (and/or other substance), as well as reservoir filling of pumps, has also not be adequately addressed in current systems and devices.

SUMMARY OF SOME OF THE EMBODIMENTS

Embodiments of the present disclosure are directed to miniature insulin patch pump and an assistance device for reservoir filling and cannula insertion. Although discussions of several embodiments in the current disclosure refer to insulin as the drug being delivered by the patch pump disclosed herein, it is to be understood that the use of the disclosed patch pump to other fluids/drugs is deemed to be within the scope of the inventive embodiments described herein.

In some embodiments of the present disclosure, a drug delivery system is provided and includes at least two or more, and in some embodiments, all of a drug-delivery patch pump, an assistance device configured for at least one of reservoir filling and cannula insertion, and, optionally, a gateway device.

Such embodiments may include one or more of (and in some embodiments, a plurality of, and in some embodiments, all of) the following additional features, functions, structures, and/or clarifications (as the case may be), creating yet further embodiments:
 the gateway device can be a smartphone;
 the gateway device can be configured to enable communication to and/or from the pump to at least one server; and
 one or more of a charger, and an assistance device, where the assistance device may include at least one of a reservoir filling mechanism, a cannula insertion mechanism, and a DR-RP alignment mechanism;

In some embodiments, a substance/drug-delivery patch pump is provided and includes a reusable part (RP) including a power source, a driving mechanism, and an electronic module, and a disposable part (DP), where the disposable part can include at least a plurality of an adhesive base, a reservoir, a dosing mechanism, and a cannula.

In some embodiments, an assistance device is provided, which is configured for use with a drug delivery pump (e.g., patch pump). Such embodiments may comprise a housing that includes at least one of a reservoir filling mechanism, a cannula insertion mechanism, and/or a disposable part (DP), reusable part (RP) alignment mechanism.

Such embodiments may include one or more of (and in some embodiments, a plurality of, and in some embodiments, all of) the following additional features, functions, structures, and/or clarifications (as the case may be), creating yet further embodiments:
 the device can be configured for preassembly with a disposable part of drug delivery patch pump;
 one or more notches configured for insertion of a reusable part (RP) of a drug delivery patch pump, and for alignment of the RP and a disposable part (DP) of the drug delivery patch;
 the reservoir filling mechanism resides in a first housing and the cannula insertion mechanism and the DR-RP alignment mechanism reside in a second housing;
 the reservoir filling mechanism can be configured to provide delivery of insulin (and/or other drug or substance) from an insulin vial to a reservoir of a patch pump;
 the device can be configured such that the vial is connected to the device and delivers a set quantum/quantity of drug (e.g., 50 units) from the vial to the reservoir;
 delivery of a drug (into the reservoir) can be accomplished via pressing the vial once and releasing;
 consecutive vial pressing delivers multiple insulin quantities;
 a rotational and/or linear means configured to set an amount of drug to be delivered from the vial;
 the reservoir filling mechanism can include an interspace having a changeable volume, such that, when the interspace volume increases, drug can be delivered from the vial via a filling needle into the interspace, and when the interspace volume decreases, drug can be delivered from the interspace via a transferring needle into the reservoir;
 the reservoir filling mechanism can include at least one of, and preferably a plurality of, and more preferably all of: a cylindrical filling sleeve having upper and lower caps and upper and lower openings, a filling piston configured for linearly displacement within the filling sleeve, and a sliding rod that transverses the upper opening of the filling sleeve;
  the sliding rod can be connected to the filling piston at one side and can be connected to a vial adaptor at the other side;
  an interspace can be formed between the filling piston and the upper part of the filling sleeve;
one or more gaskets configured to hermetically seal components of the reservoir filling mechanism;
the reservoir filling mechanism can include at least one of, and preferably, a plurality of, and more preferably, all of: a vial adaptor, a filling needle, having a sharp tip residing within the vial adaptor, where the filling needle can be configured to transverse the sliding rod and can provide hydraulic communication between the filling needle tip and an interspace;
the reservoir filling mechanism can include a first unidirectional valve configured to provide one-way fluid delivery through the filling needle, and/or a second unidirectional valve which can be configured to provide one-way fluid delivery through a transferring needle;
the reservoir filling mechanism can further comprise a venting needle including a sharp tip that can be arranged within the vial adaptor, and transverses the sliding rod to provide air communication between the atmosphere and the venting needle tip;
the reservoir filling mechanism can include a piston spring configured for compression and decompression when the piston is displaced (e.g., downward, upward, one direction, and an opposite direction);
the reservoir filling mechanism can include at least one needle protector;
at least one of the needle protectors can comprise a petal-like shaped spring;
  the petal-like spring can comprise one or more bending leaves;
prior to connection of a/the vial to a/the vial adaptor, the leaves of the needle protector are configured to be parallel to at least one of a/the filling needle and a/the venting needle;
the leaves are configured to bend over at least one needle so as to protect the user from inadvertent self-pricking;
In some embodiments, a drug delivery system is provided and includes at least one of a cannula insertion mechanism, and a reservoir filling mechanism. Such embodiments may include one or more of (and in some embodiments, a plurality of, and in some embodiments, all of) the following additional features, functions, structures, and/or clarifications (as the case may be), creating yet further embodiments:
  the reservoir filling mechanism can include a plurality of: a vial adaptor, a plunger, a venting needle, a filling needle, a filling needle cap, and a cylinder, where:
    the filling needle and/or venting needle can be configured to traverse through the body of the plunger;
    ends of the filling needle and/or venting needle protrude from one and/or another extremity of the plunger;
    a first end of the plunger can be connected with the vial adaptor;
    the venting needle and a first end of the filling needle can both protrude from a first end of plunger into an interior of the vial adaptor;
    a second end of the plunger can be configured to fit within the cylinder;
    a seal can be included between the plunger and the cylinder via a gasket;
    a closed end of the cylinder can be configured with a septum;
    the filling and/or venting needles include sharp tips ends;
    the vial adaptor can be configured to reversibly receive a vial;
    upon the vial being placed in the vial adaptor, the septum of the vial adaptor can be pierced by a first end of the venting needle and a first end of filling needle;
    the venting needle includes a unidirectional valve configured to enable air to flow from an interior of the cylinder to an interior of the vial;
    an end of the filling needle includes a filling needle cap;
    the filling needle cap is configured to seal the end the of filling needle; and/or
    the reservoir filling mechanism can be configured within an assistance device such that the septum of the cylinder is adjacent to or in contact with a filling port septum.
In some embodiments, a reservoir filling method for filling the reservoir of a drug delivery system with a substance, is provided and includes, for example, placing a vial in a vial adaptor such that a tip of a venting needle and a first tip of a filling needle pierce a septum of the vial, such that air from an interior of a cylinder flows through the venting needle and into the interior of the vial, pushing a plunger of the vial adaptor in a direction of a closed end of the cylinder, such that air trapped in the interior of the cylinder is reduced and/or compressed and a substance from the vial flows to a filling well and a filling conduit. As a result of a pressure differential across a reservoir plunger, the reservoir plunger then moves to increase a volume of the reservoir of the drug delivery system thereby filling the reservoir with the substance. The method also includes optionally sending a level of the substance within the reservoir, which may be used to provide a user information on the amount of substance in the reservoir.
In some embodiments, a patch pump assisting system is provided and includes an assisting device including a soft cannula insertion mechanism configured to at least insert a soft cannula in tissue. The device can comprise a housing, a first exit port septum configured within a cup opening, an exit port well, and a second exit port septum. The system can also further include a soft cannula having a lumen, and a rigid cannula having a lumen. In some embodiments:
  the soft cannula and rigid cannula each include at least one lateral opening along a length thereof;
  the housing can be configured for placement on the skin of a user for cannula insertion;
  prior to insertion, the rigid cannula can be positioned within the soft cannula with both cannulas initially traversing the cup septum, and the distal ends of the soft cannula and rigid cannula are positioned within the exit port well;
  after insertion (or immediately after), the distal ends of the rigid cannula and soft cannula are positioned within and/or below the skin of a user, and corresponding lateral openings thereof are positioned within the well, and/or
  the rigid cannula can be configured for removal from the soft cannula by retraction of the assistance device from the skin tissue of the user.
Such embodiments may include one or more of (and in some embodiments, a plurality of, and in some embodiments, all of) the following additional features, functions, structures, and/or clarifications (as the case may be), creating yet further embodiments:

a cannula bending spring, where, in some embodiments, energy stored in the cannula bending spring can be released upon separation of the assisting device from a drug/substance delivery system;
  an/the energy released by a/the cannula bending spring moves the rigid cannula from a first position to a second position, where the first position can be approximately orthogonal relative to a side or portion of the housing, and/or the second position can be approximately parallel to the side or portion of the housing;
  the device can further comprise at least one of the following (and in some embodiments, a plurality of, and in some embodiments, all of): a trigger, an inserter spring, an inserter hammer, a cup, and a cup septum, where the cup can be configured to fit within the cup opening;
  the lateral opening of the soft cannula can be aligned with the lateral opening of the rigid cannula;
  a first end of the rigid cannula can be rigidly connected to an/the inserter hammer;
  a first end of the soft cannula can include a stopper configured to prevent the soft cannula from moving out of an end of a/the cup, where the stopper can be integral with the soft cannula;
  a/the cup septum can be configured to seal the interior of the cup;
  a/the cup opening can be integral with the housing;
  a sharp end of the rigid cannula can protrude beyond an end of the soft cannula, where the sharp end of the rigid cannula and the end of the soft cannula can reside at least initially in the exit port well;
  at least initially, the rigid cannula and the soft cannula can traverse the second exit port septum;
  a/the inserter spring can be configured with potential energy;
  a/the cannula bending spring can be configured with potential energy;
  a/the cannula bending spring can be prevented from bending towards the cannulas by a side of the patch pump;
  the assisting device can be configured with a reusable part and a disposable part;
  a reservoir filling mechanism configured to fill a reservoir of the patch pump with a substance;
  at least one end of the rigid and the soft cannulas are sealed, where, in some embodiments, an end of the soft cannula establishes a seal with the rigid cannula such that, insulin or substance being dispensed, can only flow out of the exit port well during priming via the lateral openings;
  and
  the system includes an adhesive configured to adhere the device to the skin of a user, and/or the soft cannula insertion mechanism can be configured to place a tip of the soft cannula within or under the skin.

In some embodiments, a drug delivery patch-pump system is provided and includes, for example, a drug-delivery patch pump including a reservoir, a doser device, an assisting device according to any of the disclosed assisting device embodiments (and/or corresponding systems; e.g., see above). In some embodiments, upon filing the reservoir, the pump is configured for priming via the doser, such that, fluid is pumped through an exit port conduit into a filling port well, through the lumen of the rigid cannula, and out the lateral openings of each cannula. In some embodiments, the pump can be configured for continued priming until at least one of: substantially any and all air exits the doser and/or reservoir, and the drug being delivered begins to flow from the lateral openings of the cannulas.

In some embodiments, a method for inserting a soft cannula for a drug delivery system into the tissue of a user is provided, for example, and includes triggering a trigger of a cannula insertion mechanism such that one or more safety catches release energy stored in an inserter spring of the inserter mechanism such that an inserter hammer of the inserter mechanism is driven in a first direction, a cup, a cup opening, a cup septum, a rigid cannula and a soft cannula of the inserter mechanism move towards a patient's skin, and a tip of a rigid cannula punctures the skin establishing a path for a soft cannula. In some embodiments, upon an end of the cup residing on an end of cup septum, the cup placed in the cup opening, and lateral openings of the rigid and the soft cannulas being in fluid communication with an exit port well, and corresponding ends of the rigid cannula and the soft cannula are under the patient's skin, the assisting device can be removed while removing the rigid cannula from the lumen of the soft cannula.

In some such method embodiments, the energy stored in a cannula bending spring can be released upon separation of the assistance device form a drug/substance delivery system. Additionally, in some embodiments, the method further includes providing one and/or another of assisting devices disclosed herein (e.g., see above), and/or corresponding systems.

In some embodiments, a closed loop insulin delivery system is provided and includes, for example, a pump, a controller, a charger, and an assistance device. Such embodiments may include one or more of (and in some embodiments, a plurality of, and in some embodiments, all of) the following additional features, functions, structures, and/or clarifications (as the case may be), creating yet further embodiments:

the pump can include a reusable motor unit and a disposable cannula unit, where the motor unit and cannula unit can be reversibly attachable;
  the motor unit can include at least one of an electronics module, a driving mechanism and a power source;
  the electronics module can include at least one of a microprocessor, memory, and communication means;
  the communication means can comprise either or both of Bluetooth or wifi (or other nearfield communication means);
  the memory can store thereon a closed loop algorithm configured to calculate an instantaneous insulin infusion rate as a function of inputs, where the inputs can comprise past and/or present glucose levels;
  the motor unit can include a plurality of electrical contacts electrically connected to the electronics module, where the electrical contacts may include one or more contacts, of which one or more may be configured to supply power from the motor unit and one or more may be configured to transmit data in analog and/or digital form;
  the cannula unit can include at least one of a reservoir, a doser, and an adhesive base;
  the cannula unit can include a channel traversing from a first side to a second side, and where the channel can optionally be configured to at least one of: receive a continuous glucose sensor, and assist in establishing electrical contact between one or more electrical contacts on the motor unit and one or more contacts on the continuous glucose sensor;

the controller can include computer instructions operating thereon configured to perform and/or operate in combination with a closed loop algorithm;

the assistance device can include at least one of a reservoir filling mechanism, a cannula insertion mechanism, and a disposable part/reusable part alignment mechanism;

the cannula insertion mechanism can be configured to store a continuous glucose sensor and insert the sensor under the patient's skin; and a continuous glucose sensor.

In some embodiments, a continuous glucose sensor configured for use with a closed loop delivery system according to any one or more of the embodiments disclosed herein. Such embodiments include, for example, one or more of (and in some embodiments, a plurality of, and in some embodiments, all of) the following additional features, functions, structures, and/or clarifications (as the case may be), creating yet further embodiments:

the sensor comprises a head, and a prong, one or both of which may include an insulative base, such as a biocompatible plastic or a ceramic;

one or more electrical contacts may be provided on or within the head of the sensor, where the one or more contacts may be configured to interface with corresponding contacts on the motor unit, and/or may include one or more contacts for transmitting power from the motor unit, and/or one or more contacts for transmitting analog and/or digital data;

the sensor can include an electronic chip (e.g., front end chip);

the sensor can include at least one of an analog-to-digital converter, a working electrode, a counter-electrode and a reference electrode;

the sensor includes one or more additional contacts for connection with the reference electrode;

the working electrode can include a conductor made of a metal (such as platinum), and an enzyme (such as glucose oxidase), where the working electrode may also be configured to generate an electrical current proportional to an ambient glucose concentration;

a membrane (which may be PTFE) which can be configured to prevent or substantially prevent interference from non-glucose electrochemically active agents;

one or more layers of the working electrode can be printed;

the counter electrode can be made from silver and/or silver chloride;

the working electrode can be configured for electrical connection to the front end chip via a conductor;

the counter-electrode can be connected to the chip via a conductor, where the conductor may be configured to traverse the prong from a first end to a second end via an opening in the prong;

the working electrode can comprise a metal catalyst in lieu of the enzyme, and the selective membrane may be optional;

an area of tape which can be configured with adhesive on at least one side, where the tape can include a high electrical conductivity in at least one direction (e.g., the Z direction) and a low electrical conductivity in at least another direction (and preferably two directions; (e.g., the X and Y directions);

the tape may comprise a ring or frame of double sided adhesive, which can be configured to establish a water proof seal around at least one or more of the electrical contacts, when pressed between two plane surfaces sandwiching the contacts;

a liner which can be configured to cover the head of the sensor, where the liner comprises at least one of a layer of plastic, a layer of paper, and a layer of paper coated by a layer of plastic;

the liner can include a motor unit facing part and/or a cannula-unit facing part, where the cannula unit facing part may be folded over itself and can be connected to a first side (e.g., back side) of the head of the sensor with an adhesive layer;

the motor unit facing part may also be folded over itself and connected to a second side (e.g., front side) of the head using the tape;

a proximal end of the liner may be connected to a/the hammer of a/the assistance device insertion mechanism, and/or In some embodiments, an assistance device for reservoir filling and cannula insertion for use with a drug delivery device is provided and includes, for example, a filling mechanism, and an insertion mechanism configured to subcutaneously insert both a cannula and a continuous glucose sensor. In some such embodiments, the device can further include an inserter hammer configured to, in some embodiments, simultaneously deploy the cannula and the sensor, optionally through a drug delivery pump (and optionally via a channel), through a user's skin. Additionally, the hammer can comprise a plurality of hammers each configured to insert one of the cannula and the sensor.

In some embodiments, a method of operating a drug delivery system is provided and includes, for example, at least one of, in some embodiments, a plurality of, and in some embodiments, all of: inserting a motor unit of a drug delivery system into a slot of an assistance device, where a pump from the motor until can be assembled with a cannula unit of the system, filling the pump with insulin via an insulin filling mechanism, priming the pump, exposing an adhesive on a skin-facing side of the pump by peeling a liner therefrom, placing the pump on the user's skin at a desired location via an assistance device, and once the pump is adhered to the skin, triggering the cannula unit such that the cannula and the sensor are inserted into the user. Insertion can occur via elastic energy stored in a spring, force generated by the spring may be transmitted to the cannula and the sensor via at least one hammer.

Some embodiments of the present disclosure are directed to system(s) or device(s) according to any of the embodiments described and/or illustrated in any one or more of FIGS. 1-55.

Some embodiments of the present disclosure are directed to a method(s) according to any of the embodiments described herein, and/or illustrated in any one or more of FIGS. 1-55.

Support for further embodiments, as well as for one and/or another of certain features/functionality disclosed herein, and features/functionality which may be combined with features/functionality of the present disclosure (to yield yet further embodiments), can be found with reference to:

U.S. patent application No. 62/259,158, filed May 8, 2015;

PCT patent application no. PCT/IL2016/050481, filed May 5, 2016;

U.S. patent application Ser. No. 15/526,736, filed May 5, 2016;

U.S. patent application No. 62/519,982, filed Jun. 15, 2017; and

U.S. patent application No. 62/551,082, filed Aug. 28, 2017.

Each of the above noted disclosures, in its entirety, are incorporated herein by reference.

BRIEF DESCRIPTION OF THE DRAWINGS FOR AT LEAST SOME OF THE EMBODIMENTS OF THE DISCLOSURE

FIG. 3 shows a spatial view of an assistance device of the system of FIG. 1, according to some embodiments;

Figure 5:
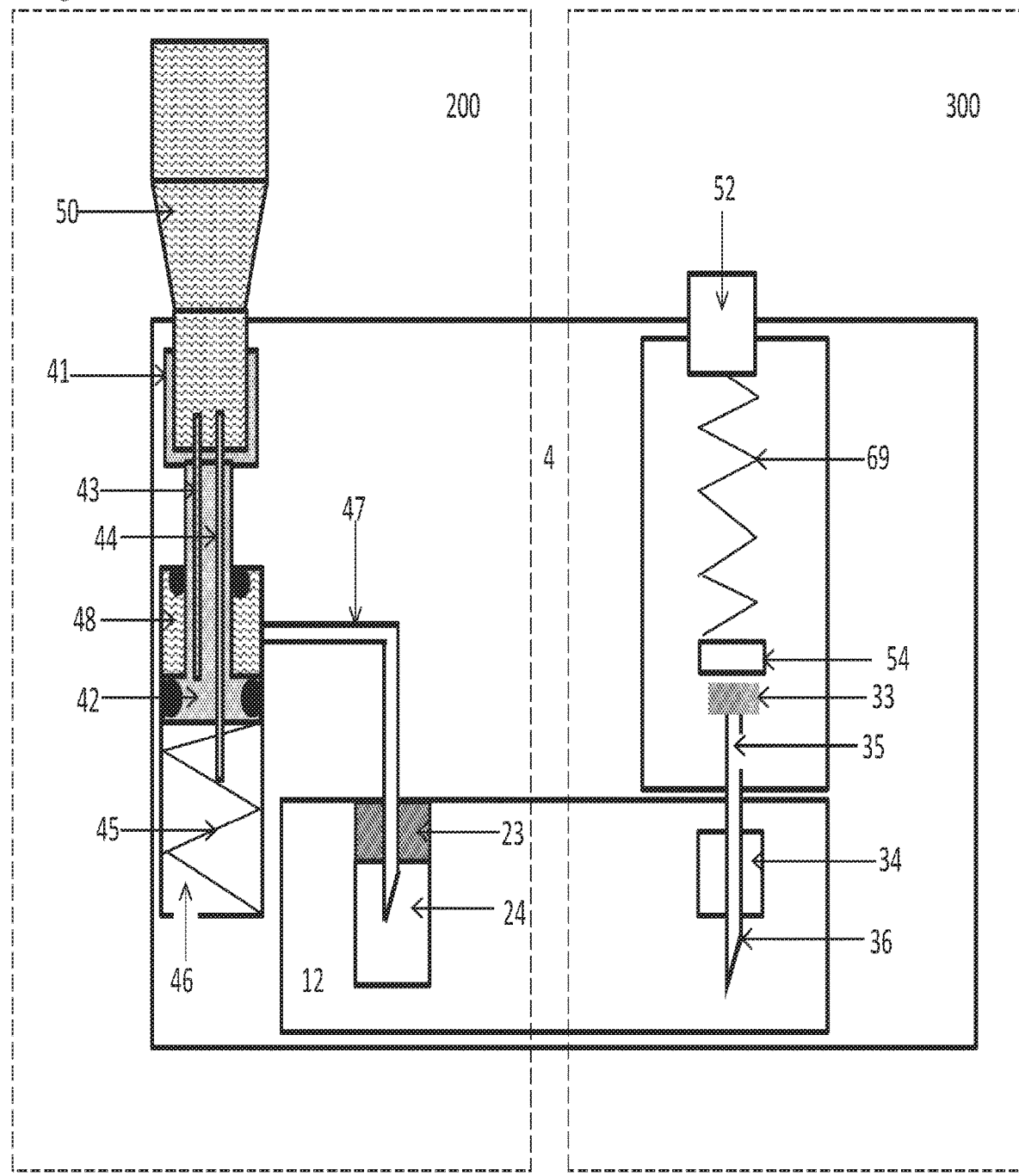
Figure 15:
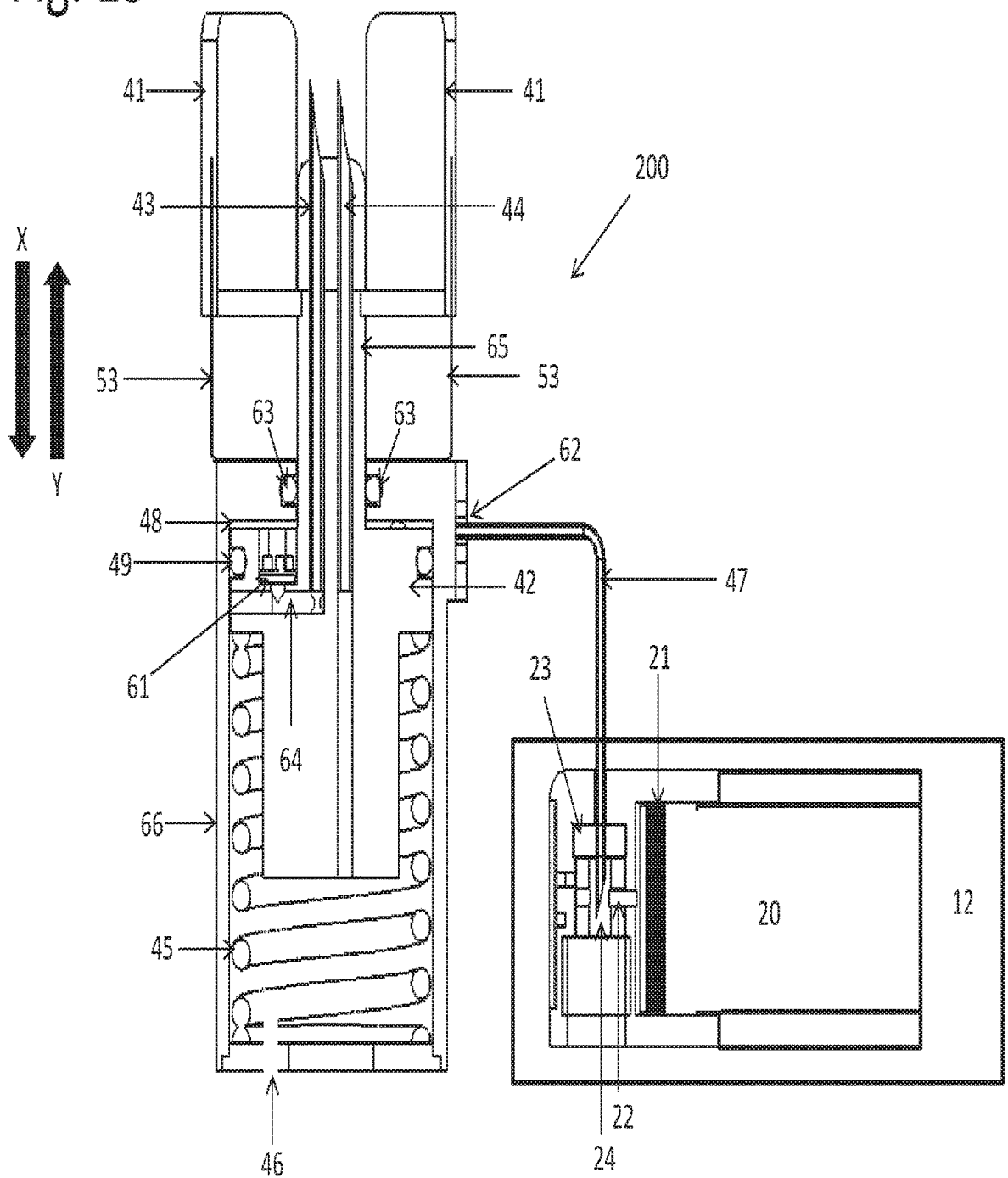
Figure 16:
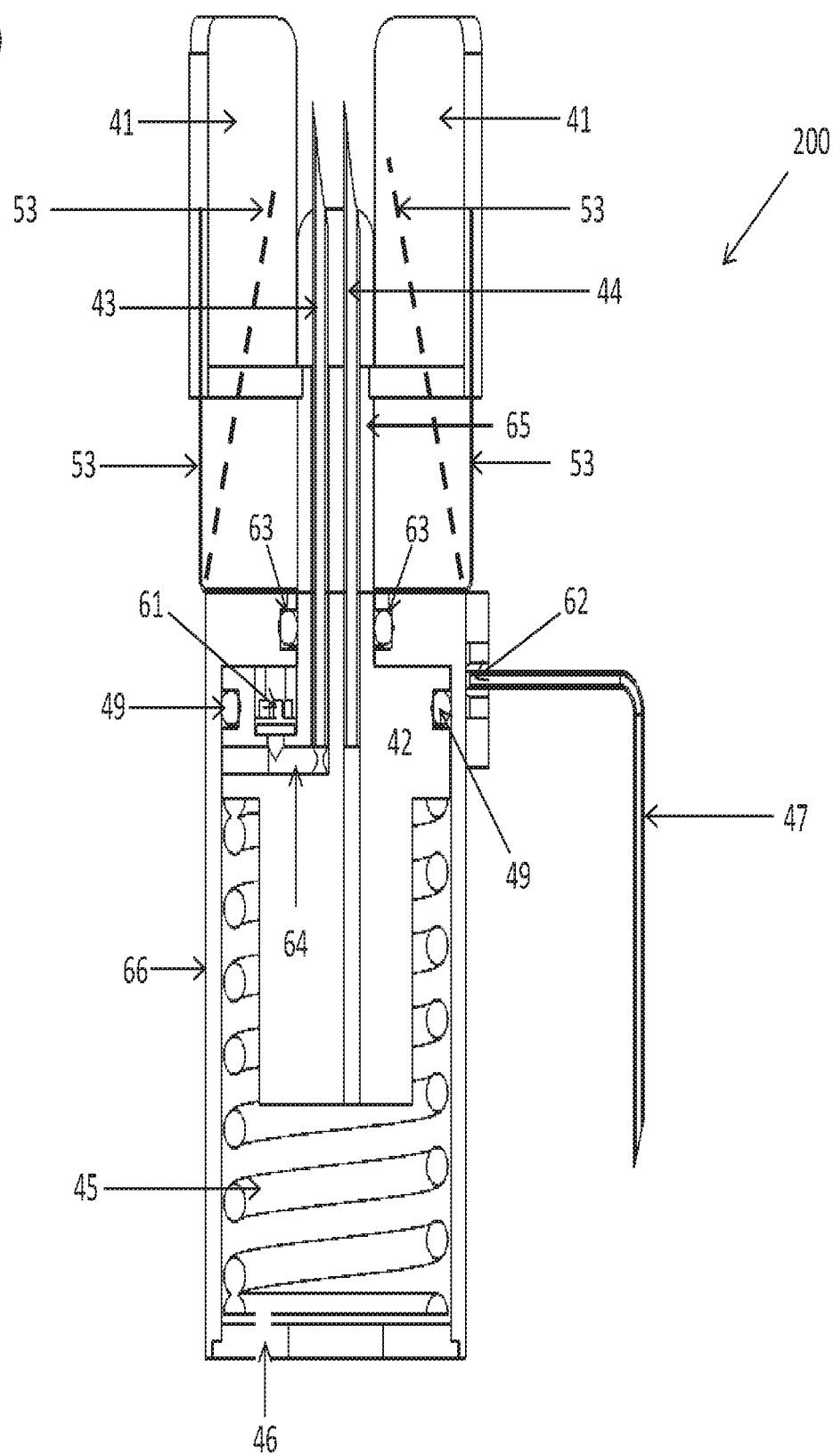
Figure 18:
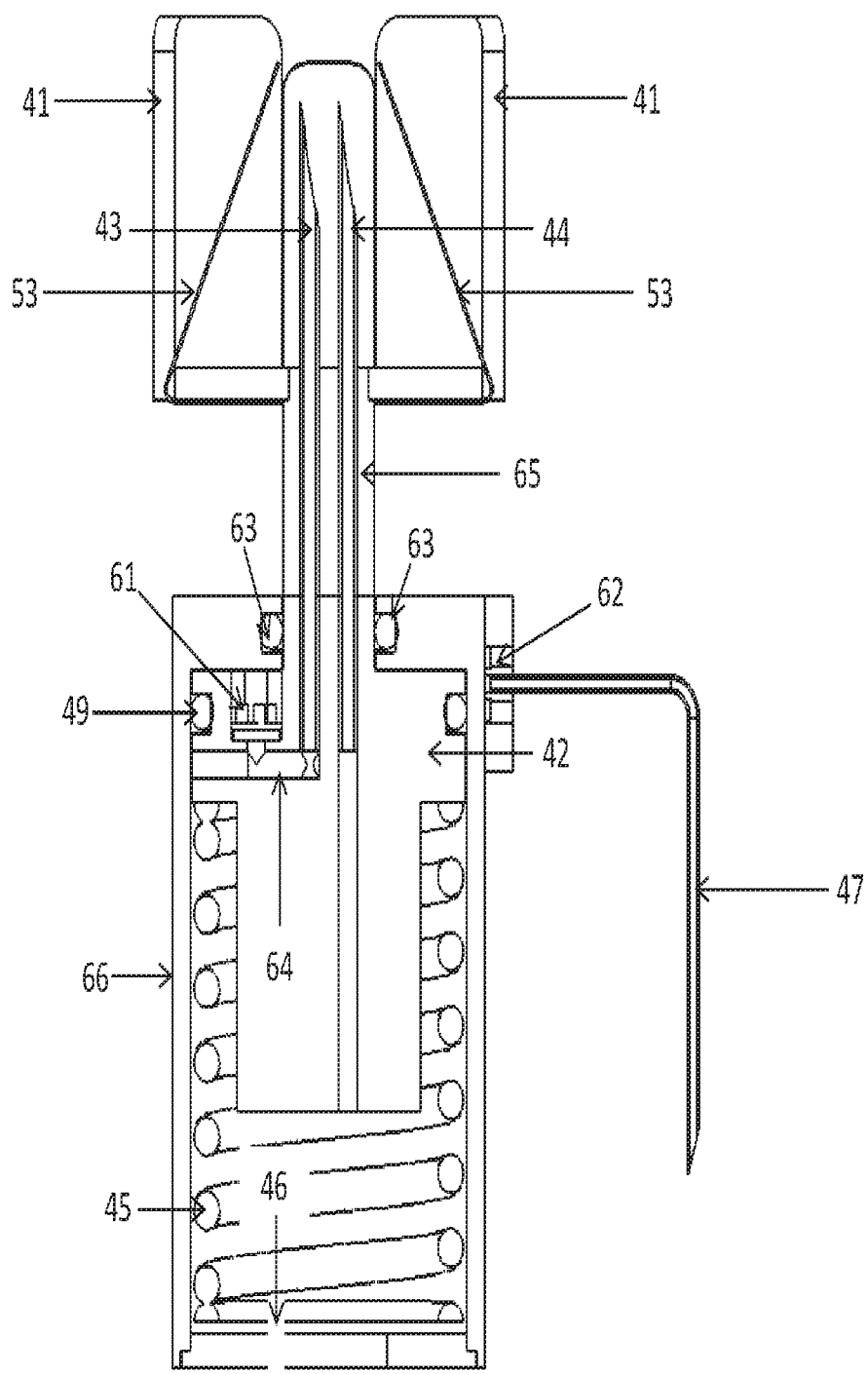
Figure 19:
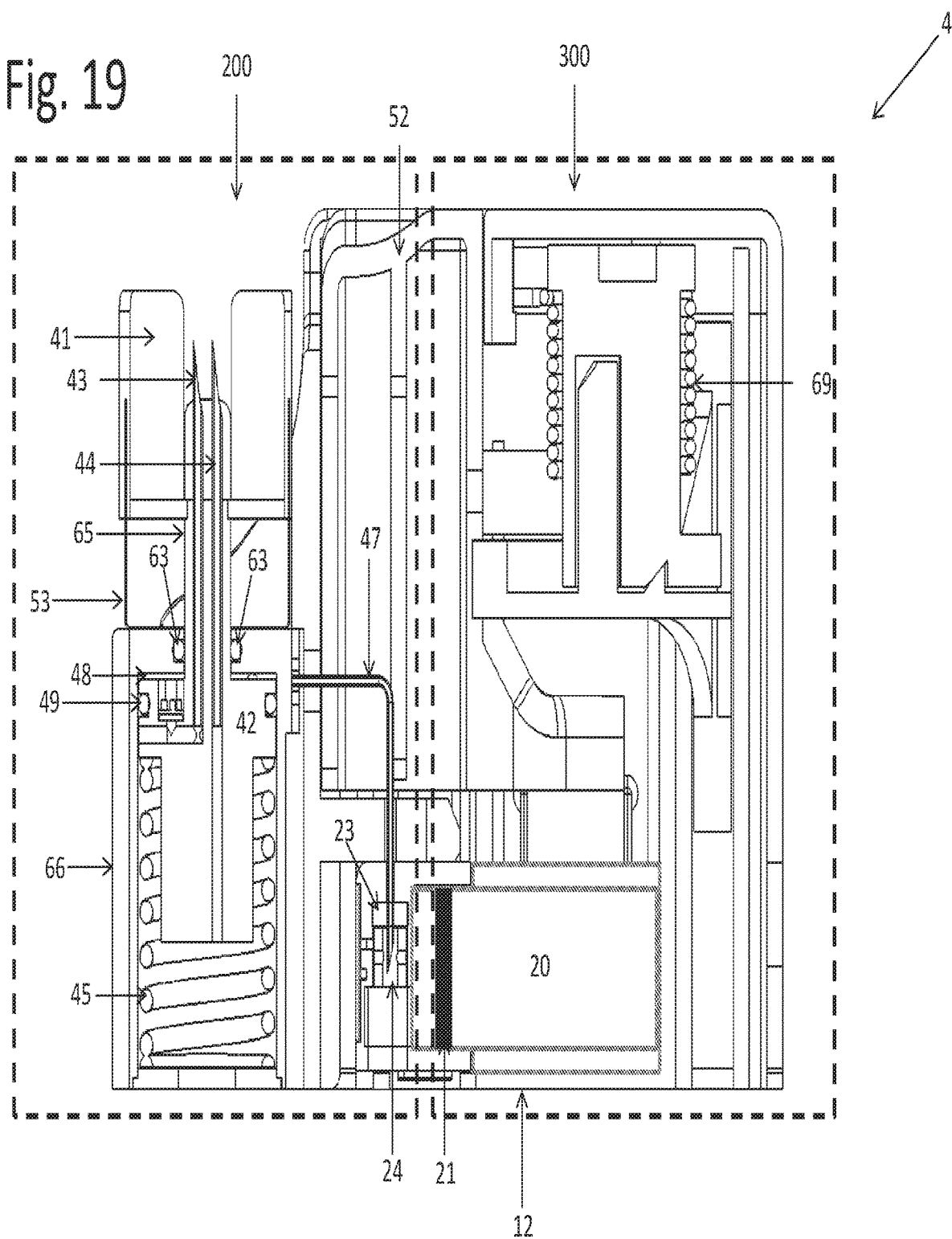

FIGS. 4A-D show a patch pump (A) and cross section views of the disposable part (B-D) thereof, according to some embodiments;

FIG. 5 shows a scheme of the main components of the assistance device of FIG. 3, and the preassembled disposable part, according to some embodiments;

FIGS. 6, 7A-B, and 8A-B show spatial views of the assistance device according to some embodiments;

FIGS. 9-14 show schemes of a reservoir filling mechanism of the assistance device (FIG. 9), and the operation phases (phase 1→phase 4) of the reservoir filling process (FIGS. 10-14), according to some embodiments;

FIGS. 15-16 show cross section views of the reservoir filling mechanism, the disposable part (FIG. 15), and the standalone reservoir filling mechanism (FIG. 16), according to some embodiments;

FIGS. 17A-C show cross section views of the reservoir filling mechanism at the first three phases of the filling process, according to some embodiments;

FIG. 18 shows a magnified cross section view of the reservoir filling mechanism after the filling process is completed and the vial is disconnected, according to some embodiments; and FIG. 19 shows a transverse cross-section view of the assistance device including a few components of the reservoir filling mechanism, cannula insertion mechanism, and the disposable part, according to some embodiments.

Figure 20:
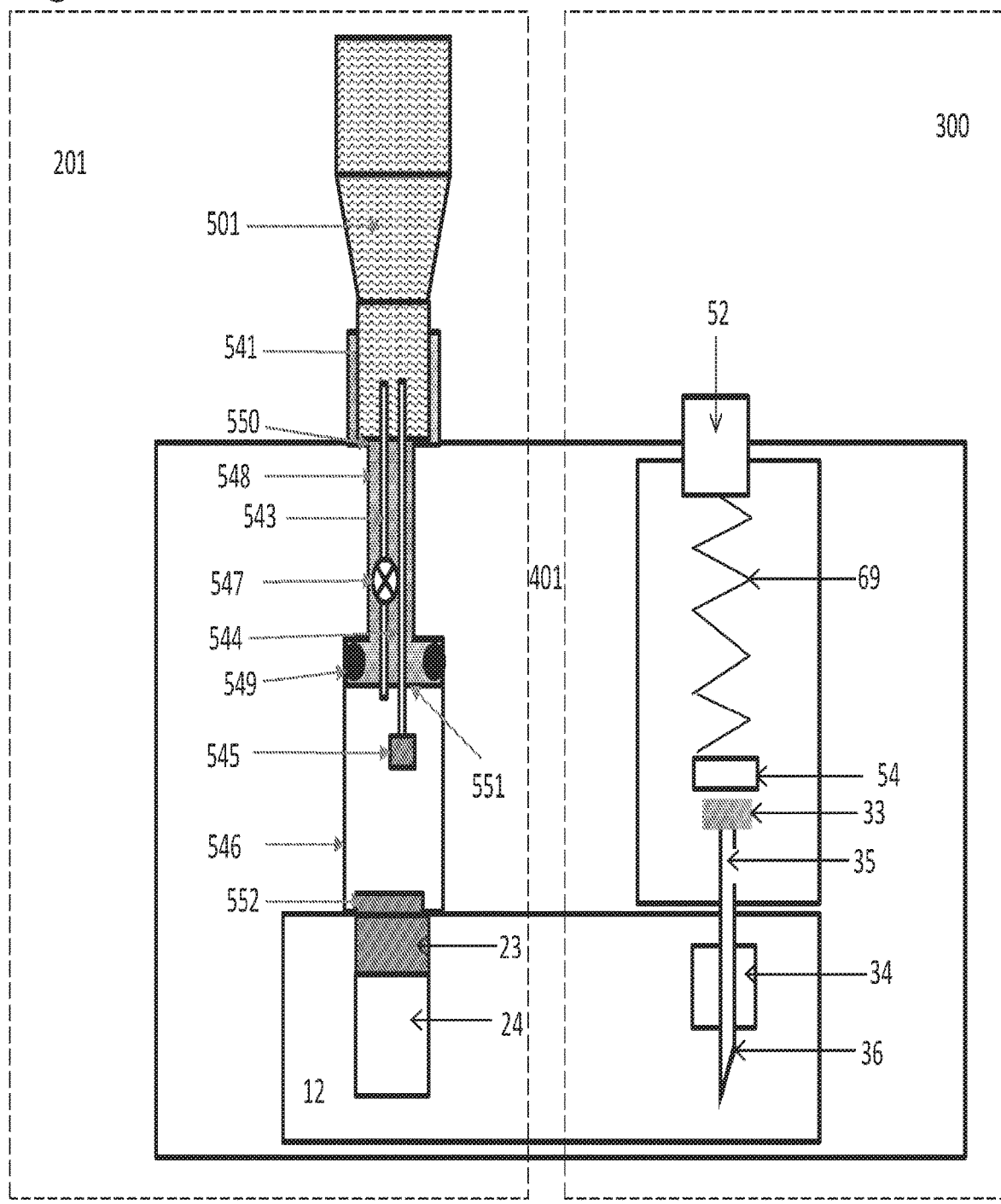

FIG. 20 shows a schematic cross section of an assistance device according to some embodiments of the present disclosure, which employs air compression using a plunger and a cylinder to cause insulin to flow from a vial to a reservoir.

FIGS. 21-26 shows a schematic cross section of the filling mechanism of FIG. 20 during various stages of its operation, according to some embodiments.

Figure 27:
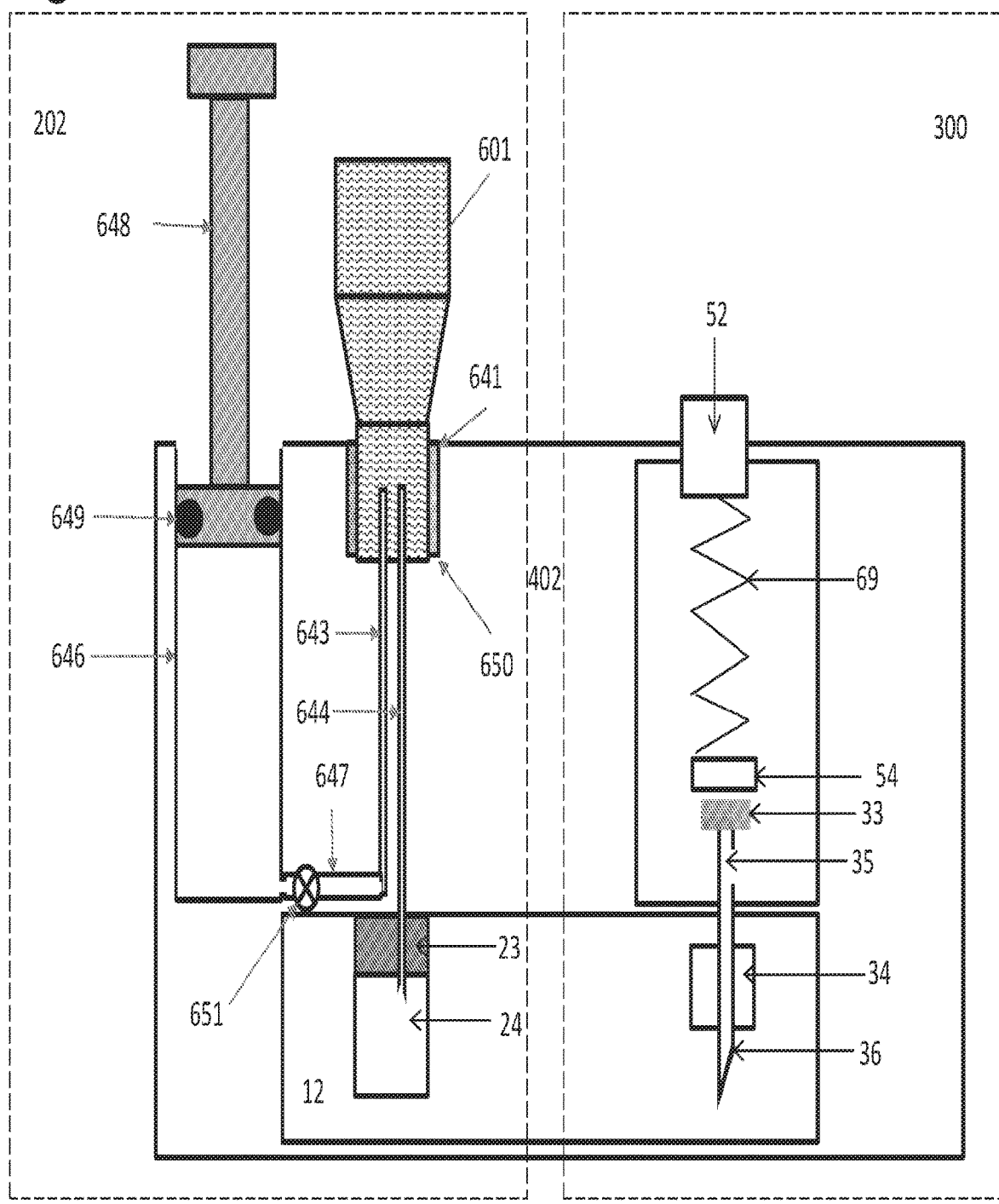

FIG. 27 shows a schematic cross section of another assistance device according to some embodiments of the present disclosure, which employs air compression using a plunger and a cylinder to cause insulin to flow from a vial to a reservoir.

FIGS. 28-32 shows a schematic cross section of the filling mechanism of FIG. 27 during various stages of its operation, according to some embodiments.

Figure 33:
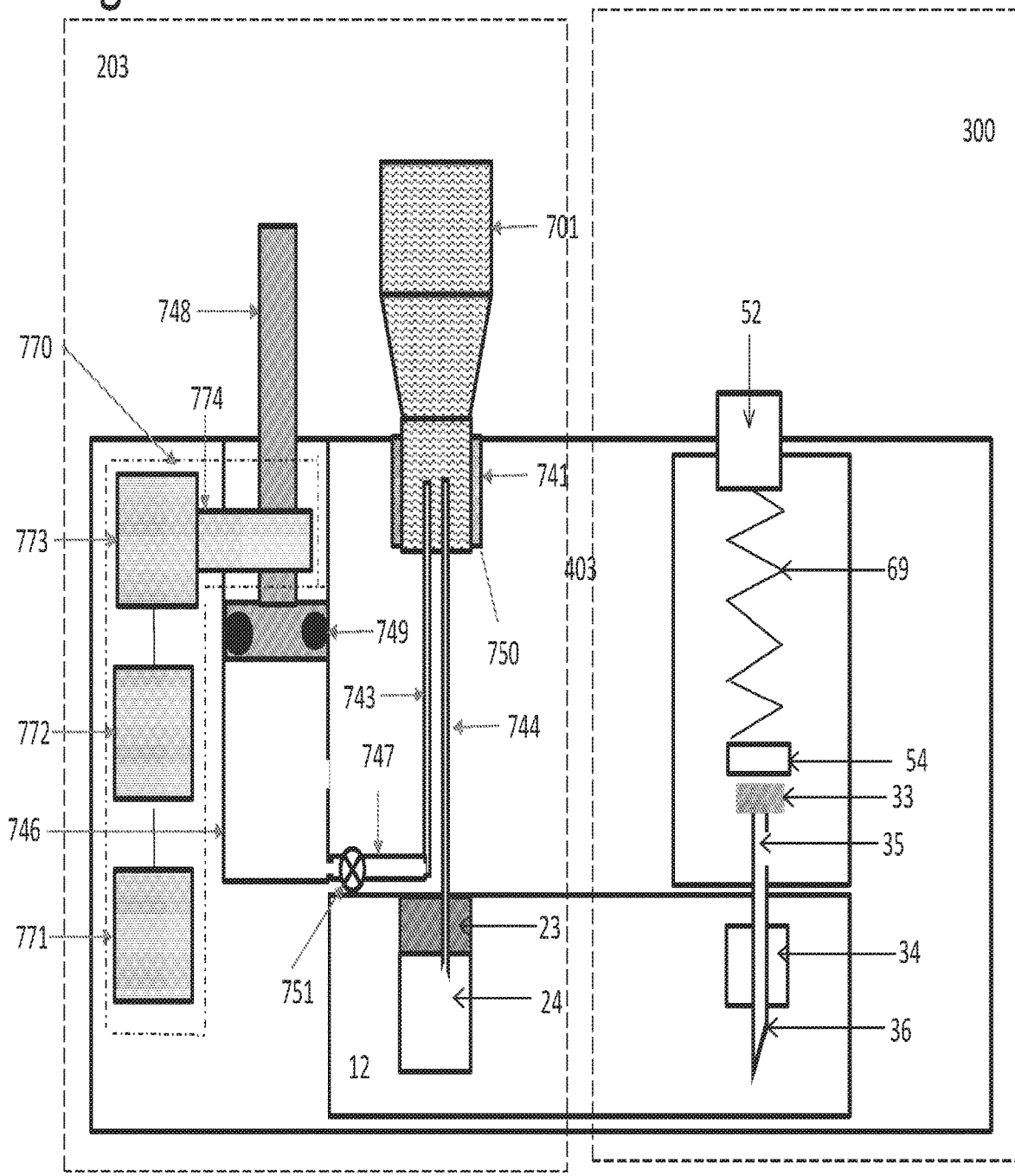

FIG. 33 shows a schematic cross section of another assistance device according to some embodiments of the present disclosure, which employs air compression using a plunger and a cylinder to cause insulin to flow from a vial to a reservoir, and utilizes a driving mechanism to move the plunger.

Figure 34:
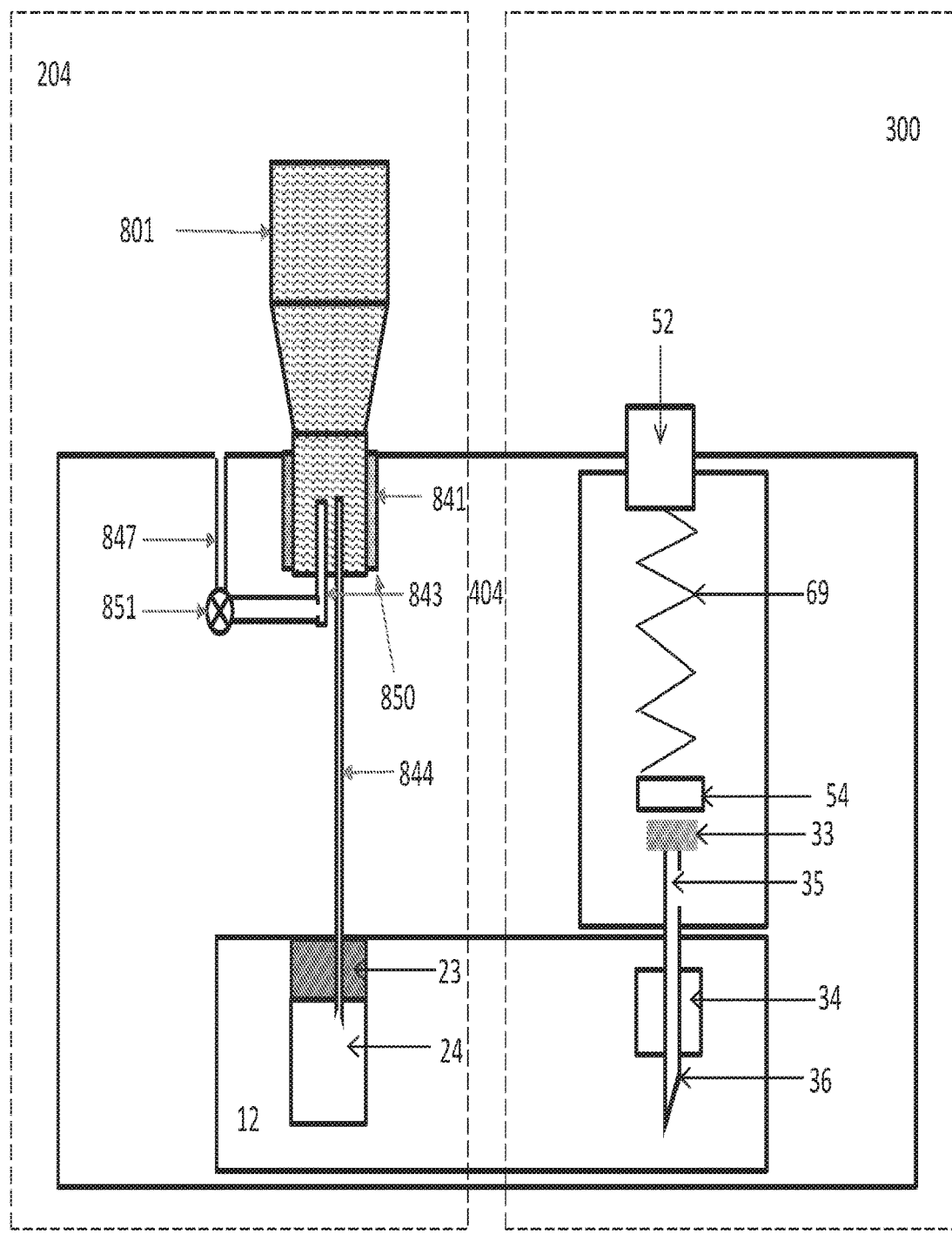
Figure 35:
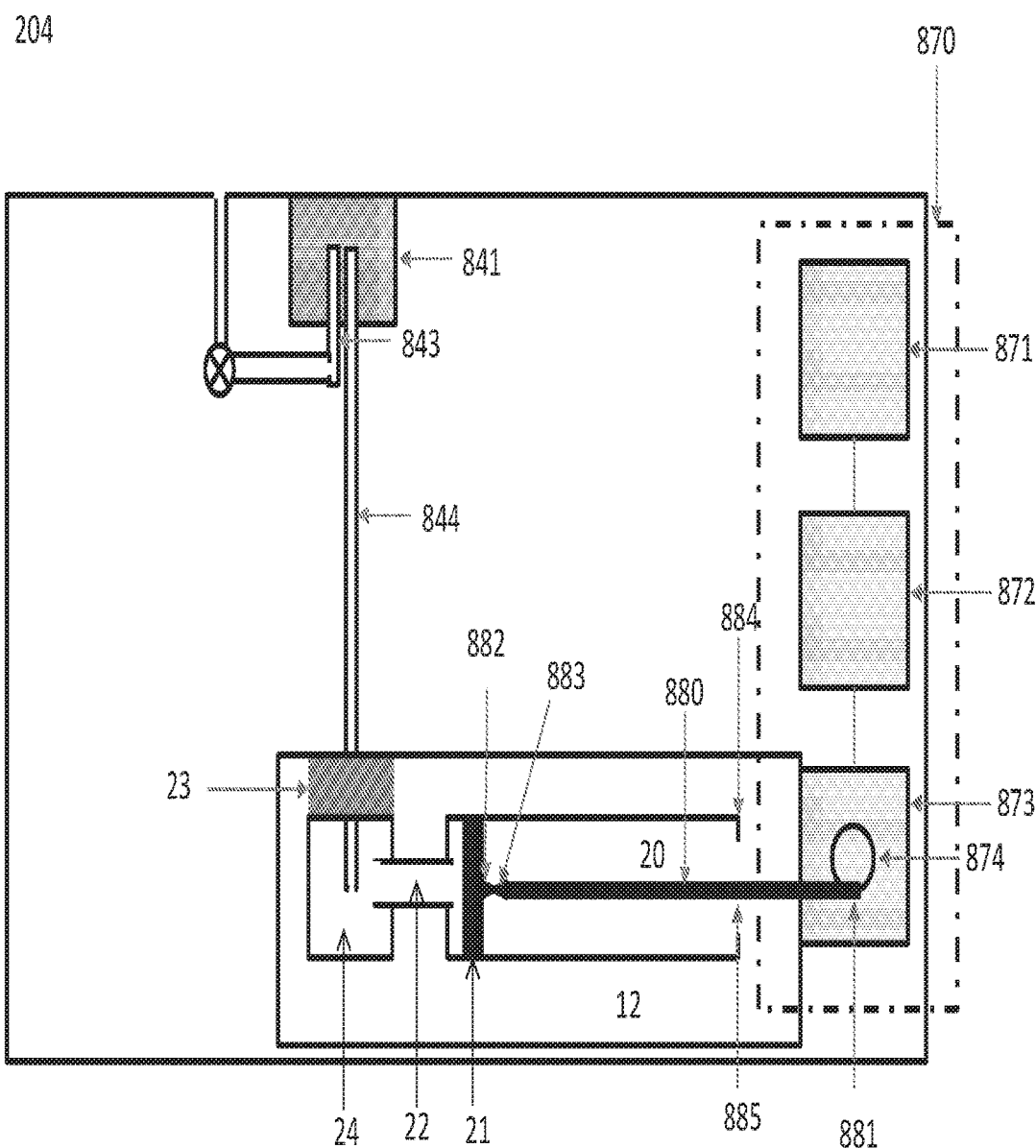
Figure 36:
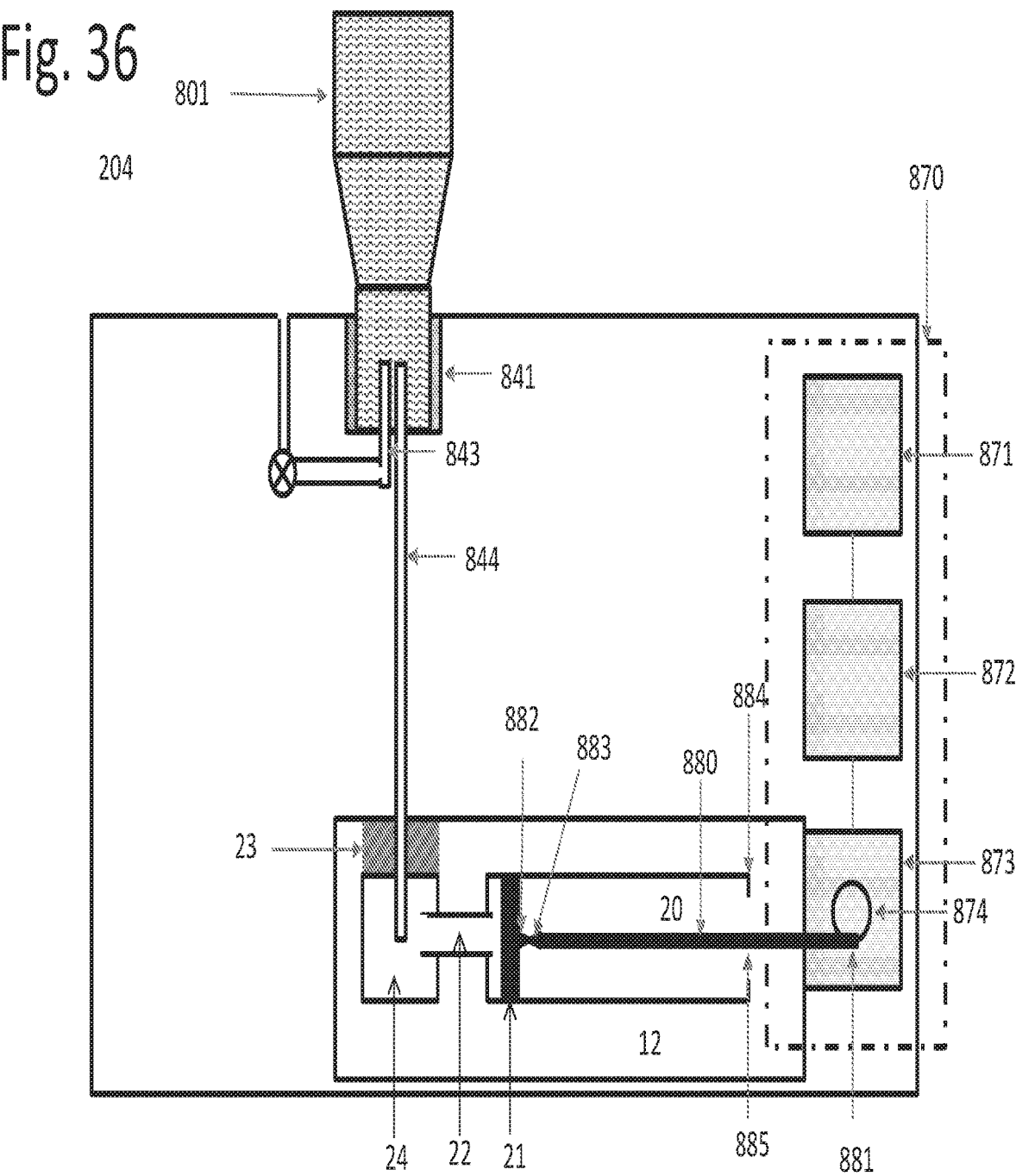
Figure 37:
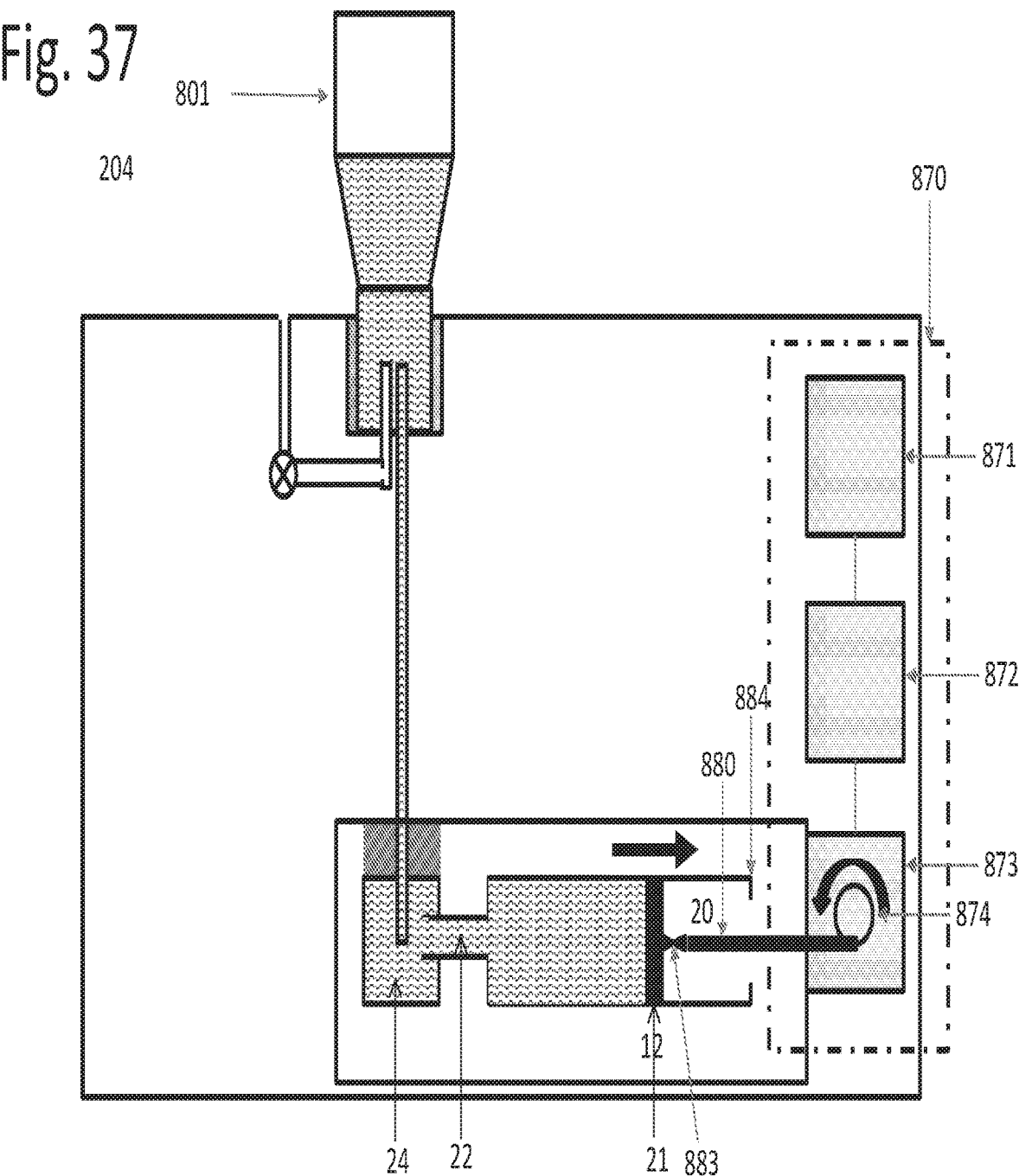

FIGS. 34-35 show schematic cross sections of another assistance device according to some embodiments of the present disclosure, which utilizes a driving mechanism to fill a reservoir with insulin by retracting the reservoir plunger.

FIGS. 36-40 show a schematic cross section of the filling mechanism of FIGS. 34-35 during various stages of its operation, according to some embodiments.

Figure 41:
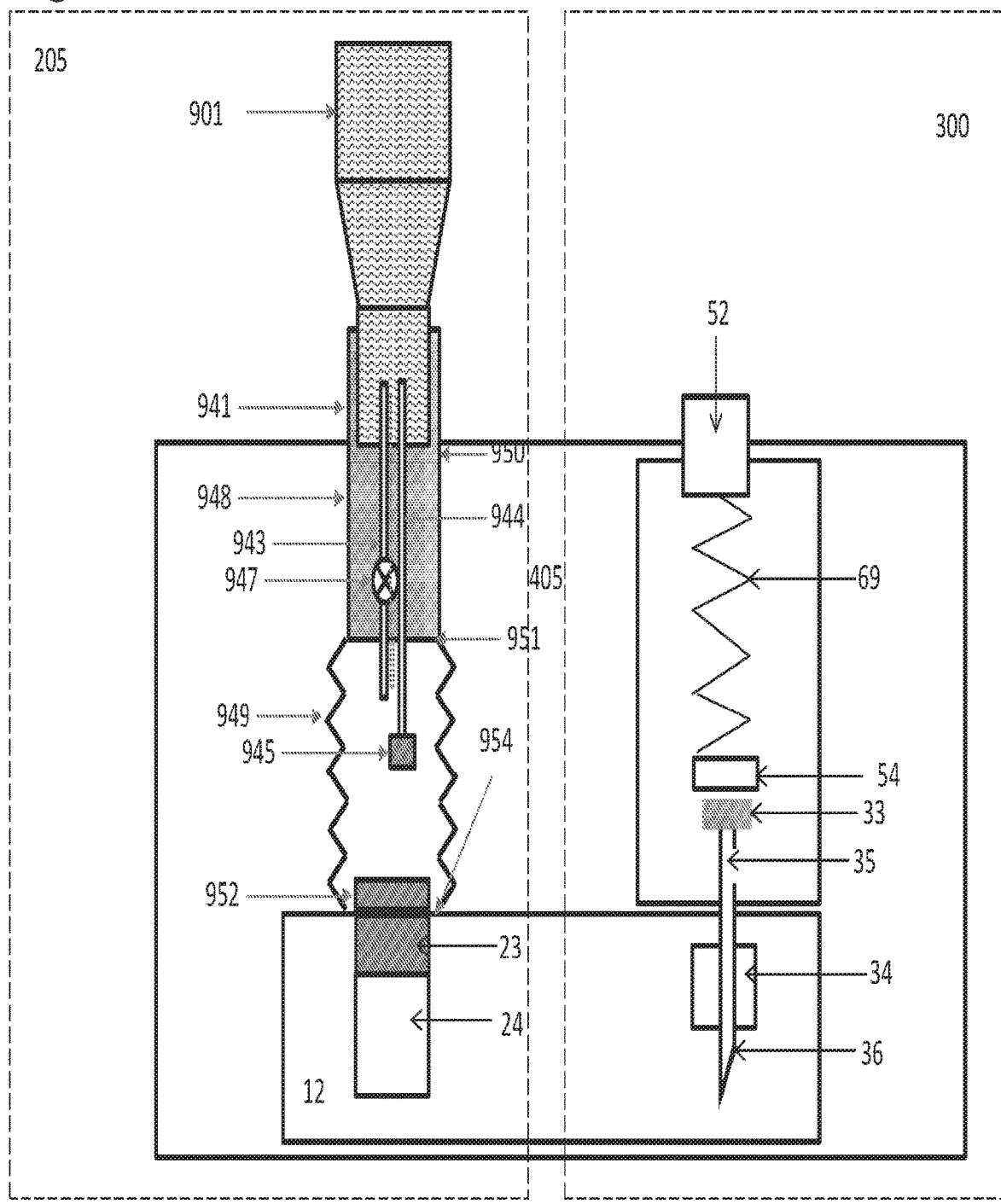

FIG. 41 shows a schematic cross section of yet another assistance device according to some embodiments of the present disclosure, which employs air compression using a bellow to cause insulin to flow from a vial to a reservoir.

Figure 43:
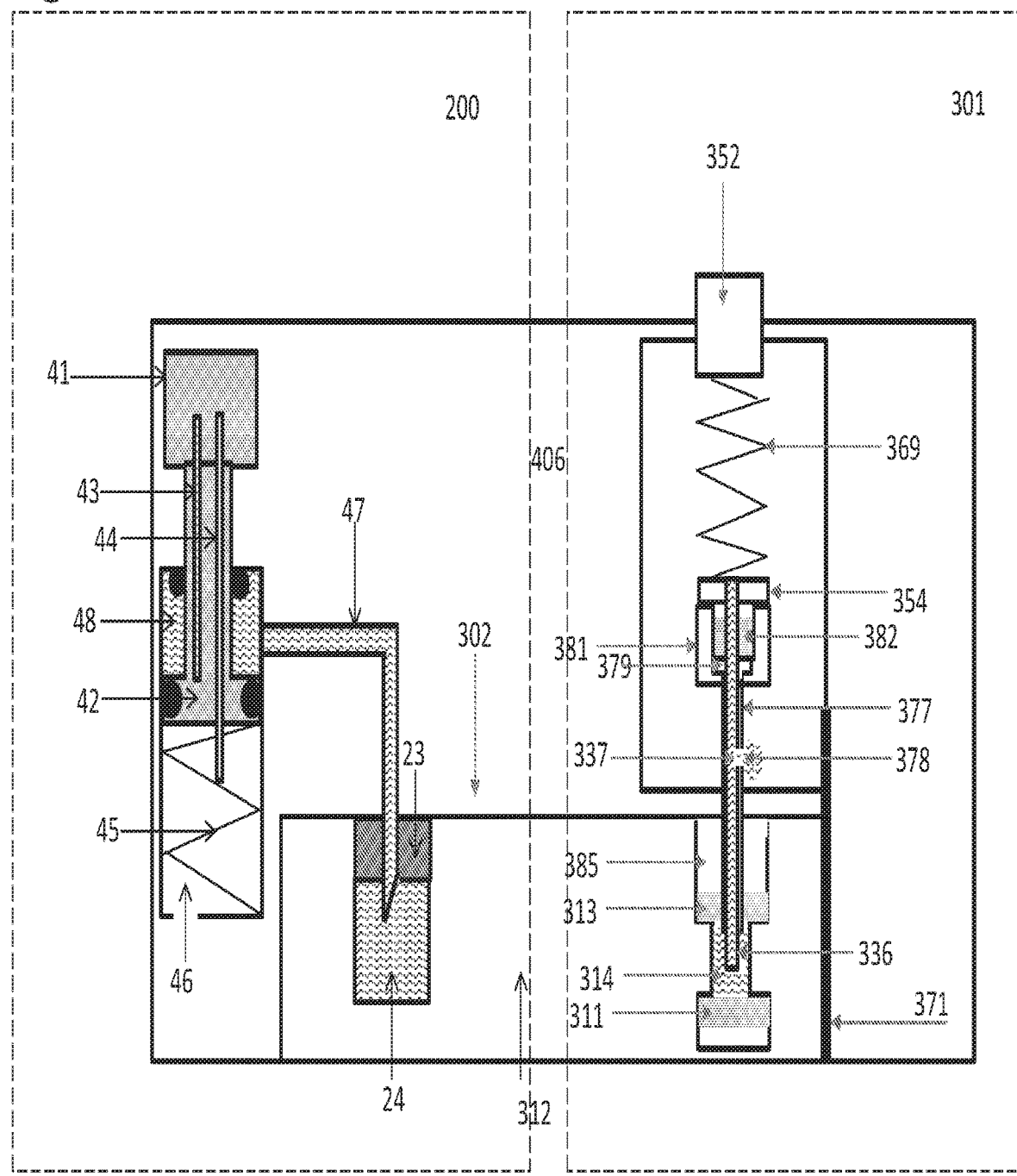

FIGS. 42A-D show a patch pump (A) and cross section views of the disposable part (B-D) thereof, according to some embodiments;

FIG. 43 shows a schematic cross section of yet another assistance device according to some embodiments of the present disclosure, which includes a soft cannula and a soft cannula insertion mechanism.

Figure 44:
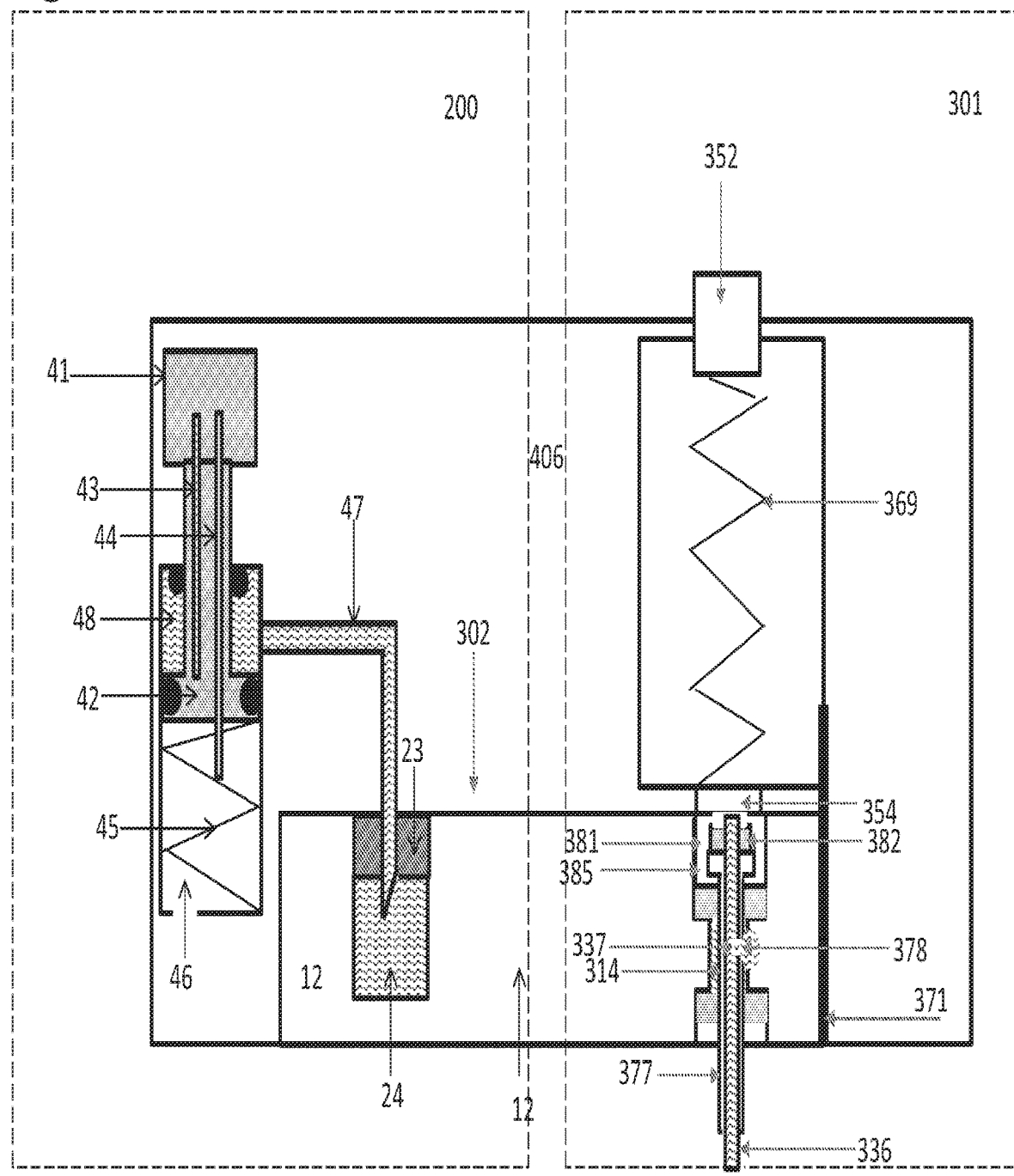
Figure 45:
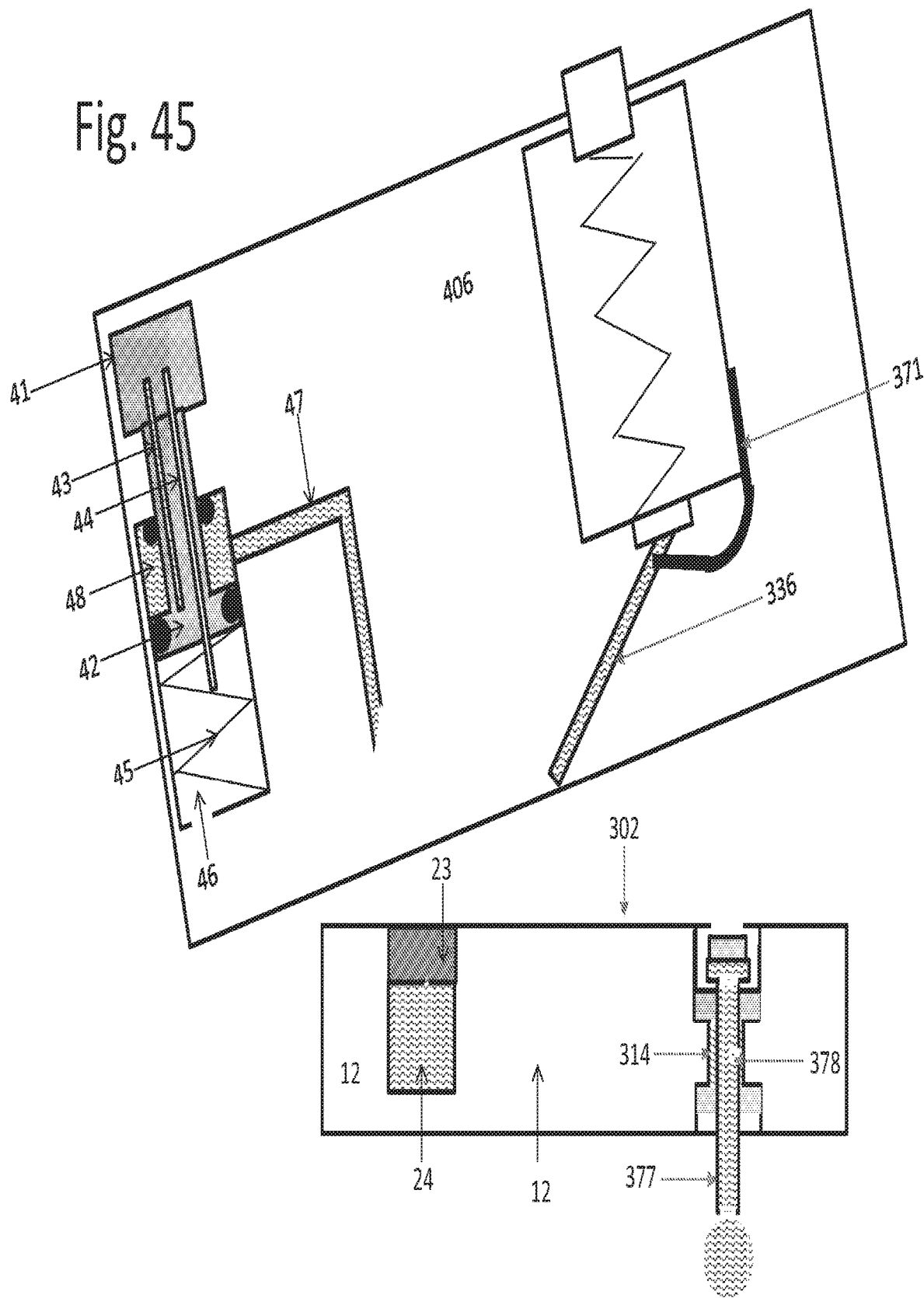

FIGS. 43-45 show a schematic of the assistance device of FIG. 43 during various stages of its operation.

Figure 46:
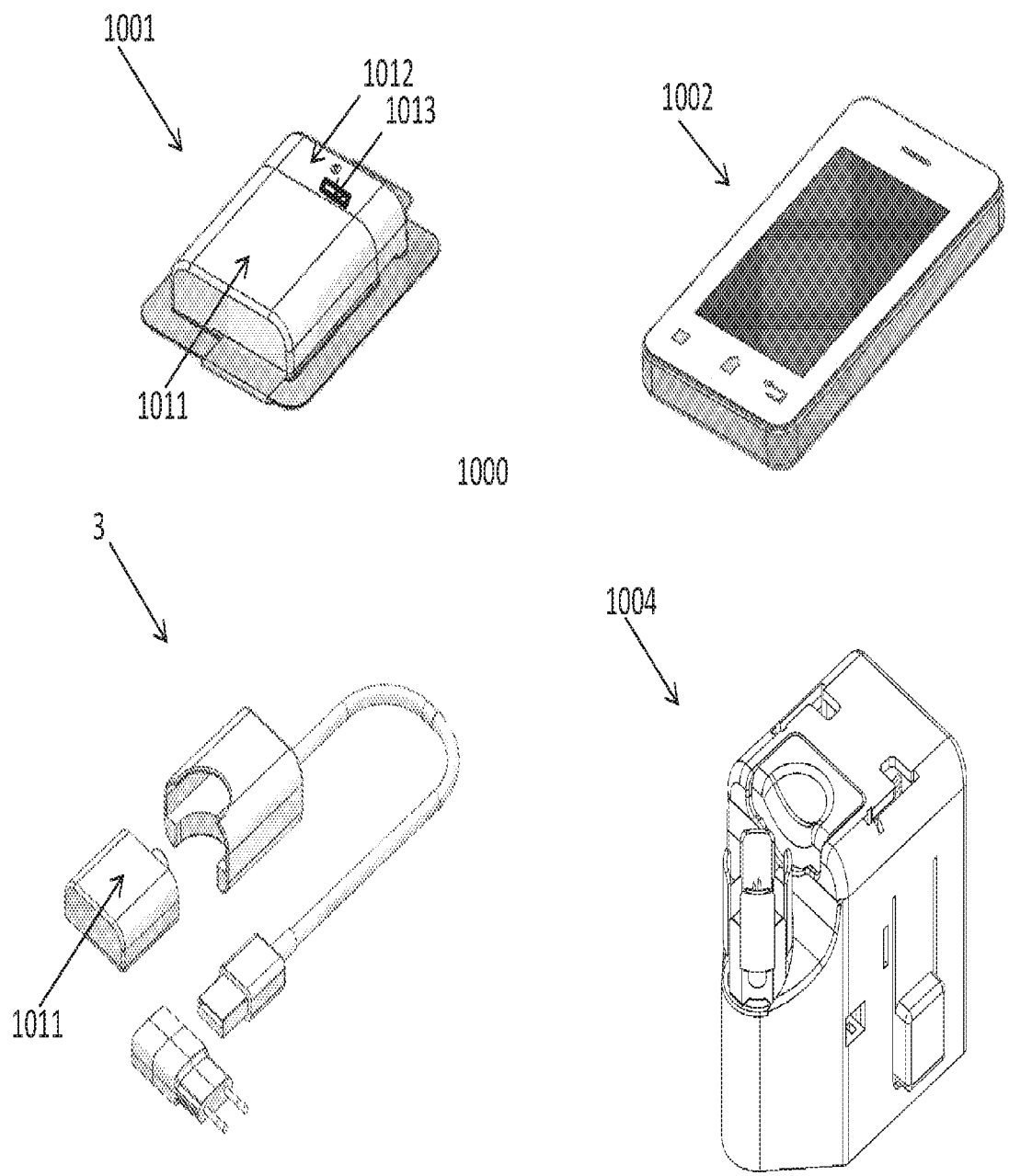

FIG. 46 shows the components of a closed loop insulin infusion system (artificial pancreas), according to some embodiments.

Figure 47:
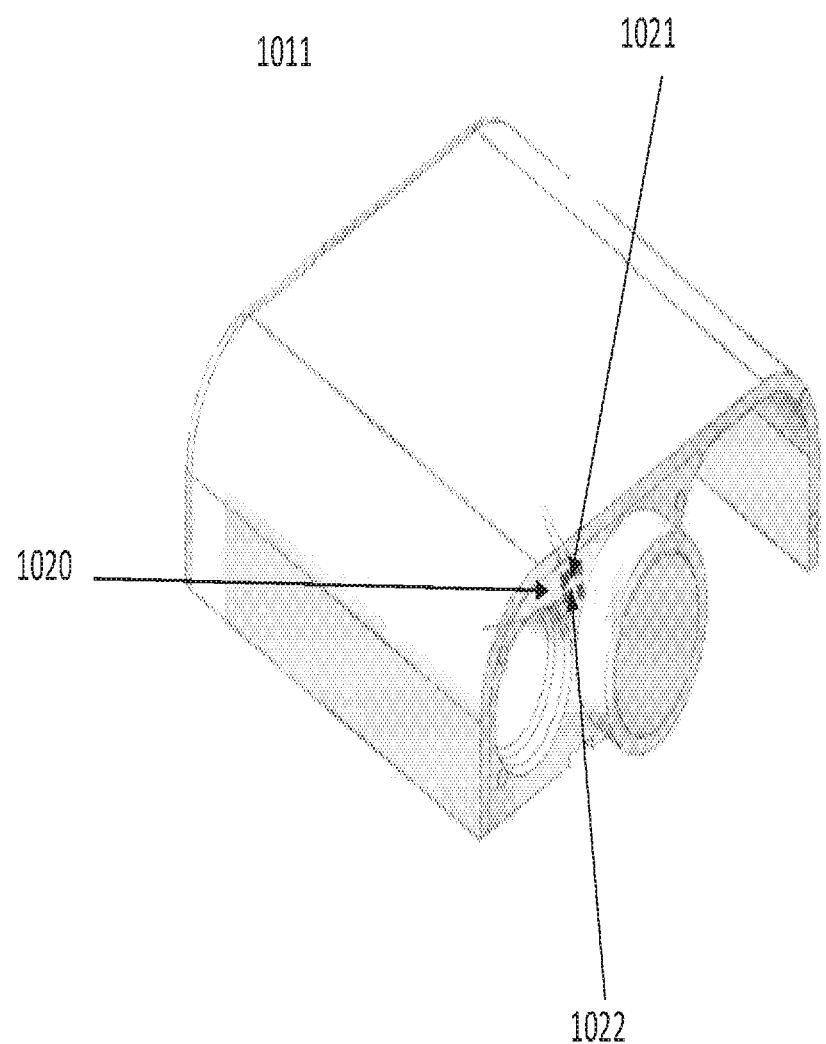

FIG. 47 shows the motor unit of the pump of a closed loop insulin infusion system (artificial pancreas), including electrical contacts on the cannula unit facing side, according to some embodiments.

Figure 48:
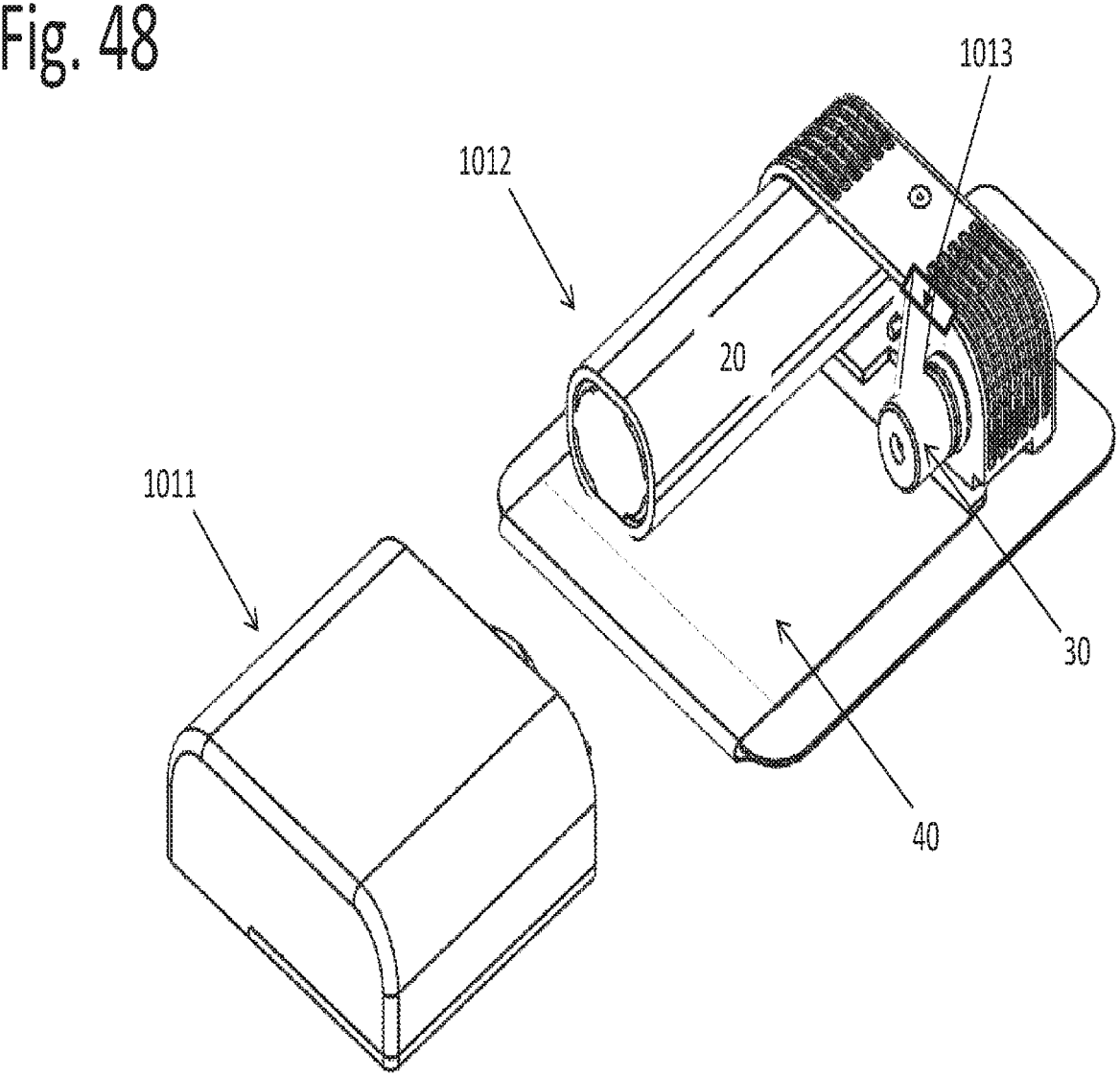

FIG. 48 shows the motor unit and the cannula unit of the pump of a closed loop insulin infusion system (artificial pancreas), according to some embodiments.

FIG. 49A-C show a top view and cross sections of the pump including a continuous glucose sensor of an artificial pancreas, according to some embodiments.

Figure 50:
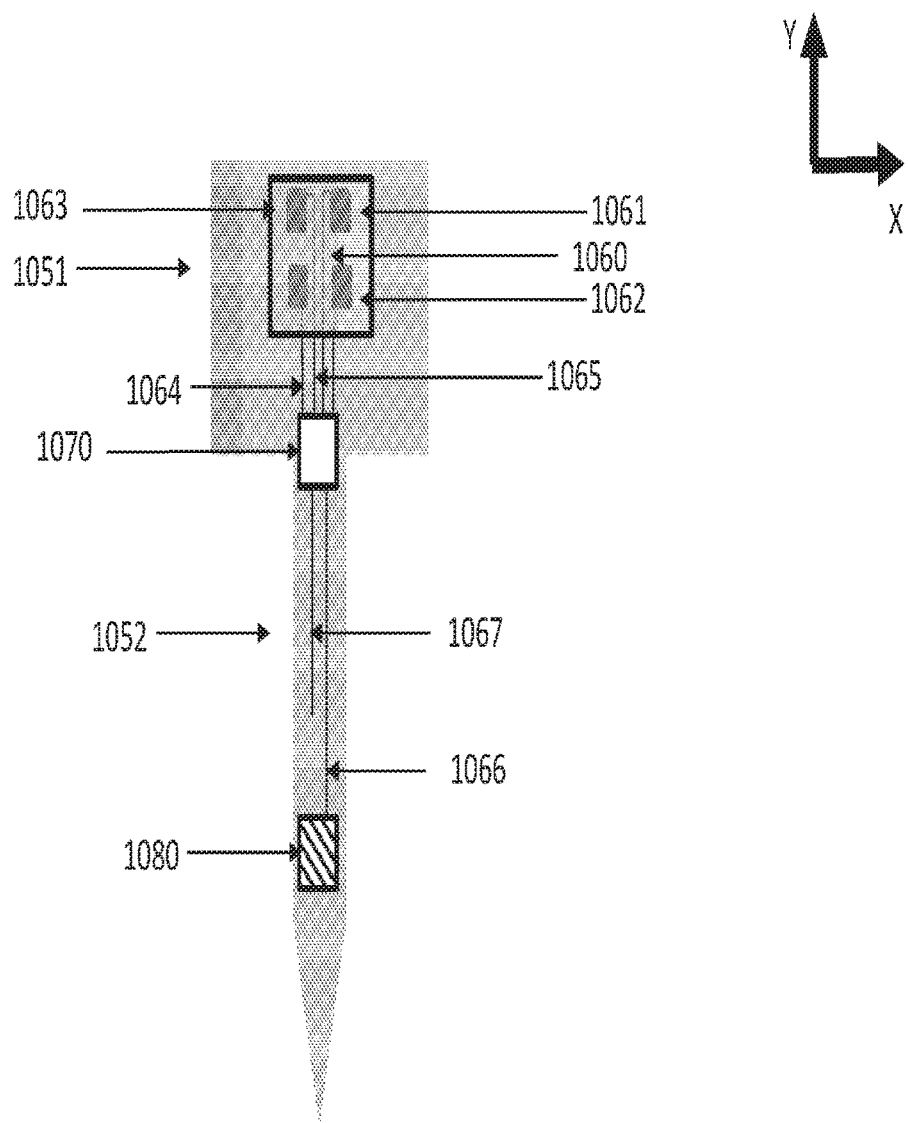

FIG. 50 shows a front view of a continuous glucose sensor of an artificial pancreas, according to some embodiments.

Figure 51:
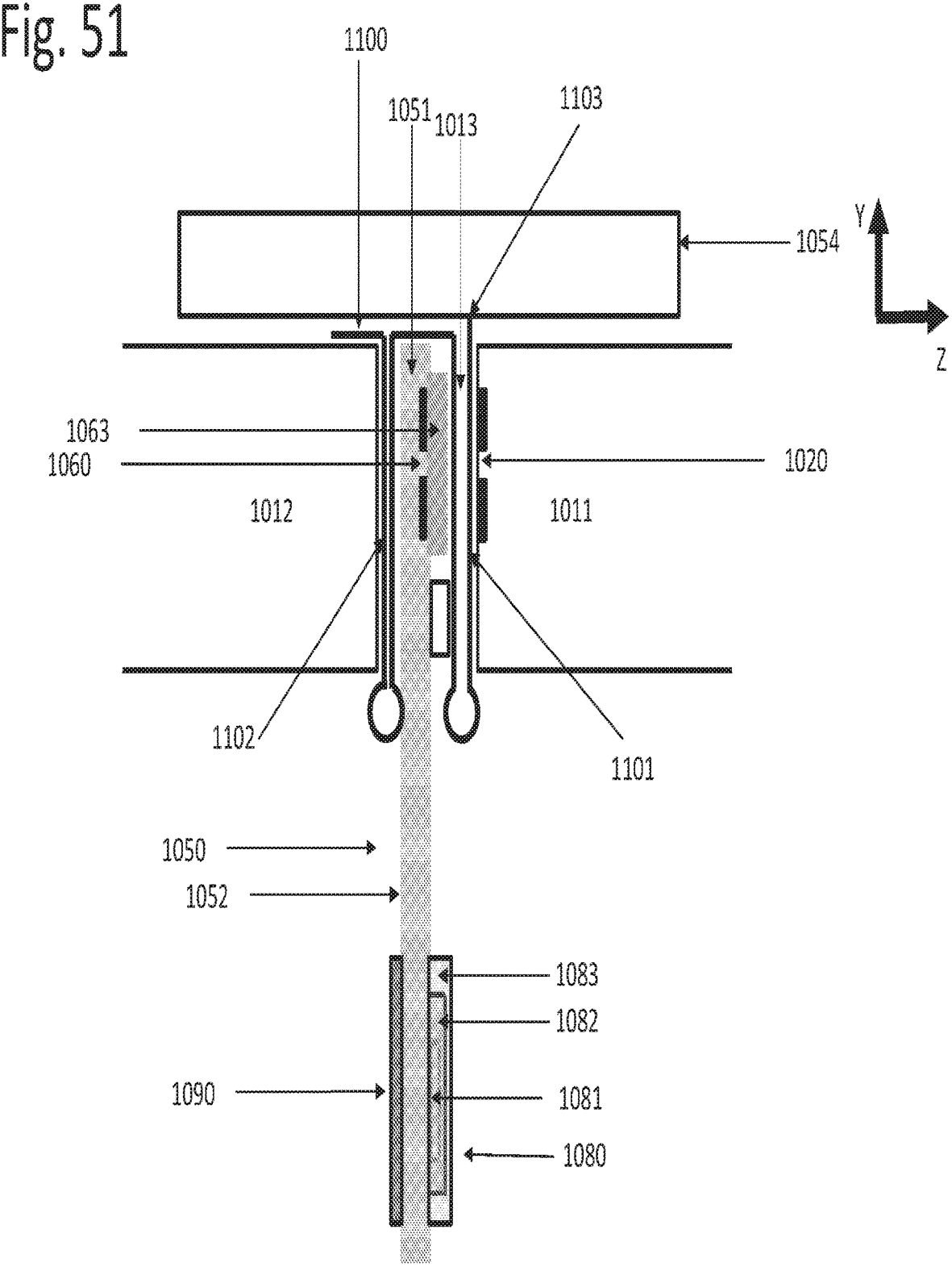

FIG. 51 shows a side view of a continuous glucose sensor of an artificial pancreas, placed in a channel in the pump of the artificial pancreas, according to some embodiments.

Figure 52:
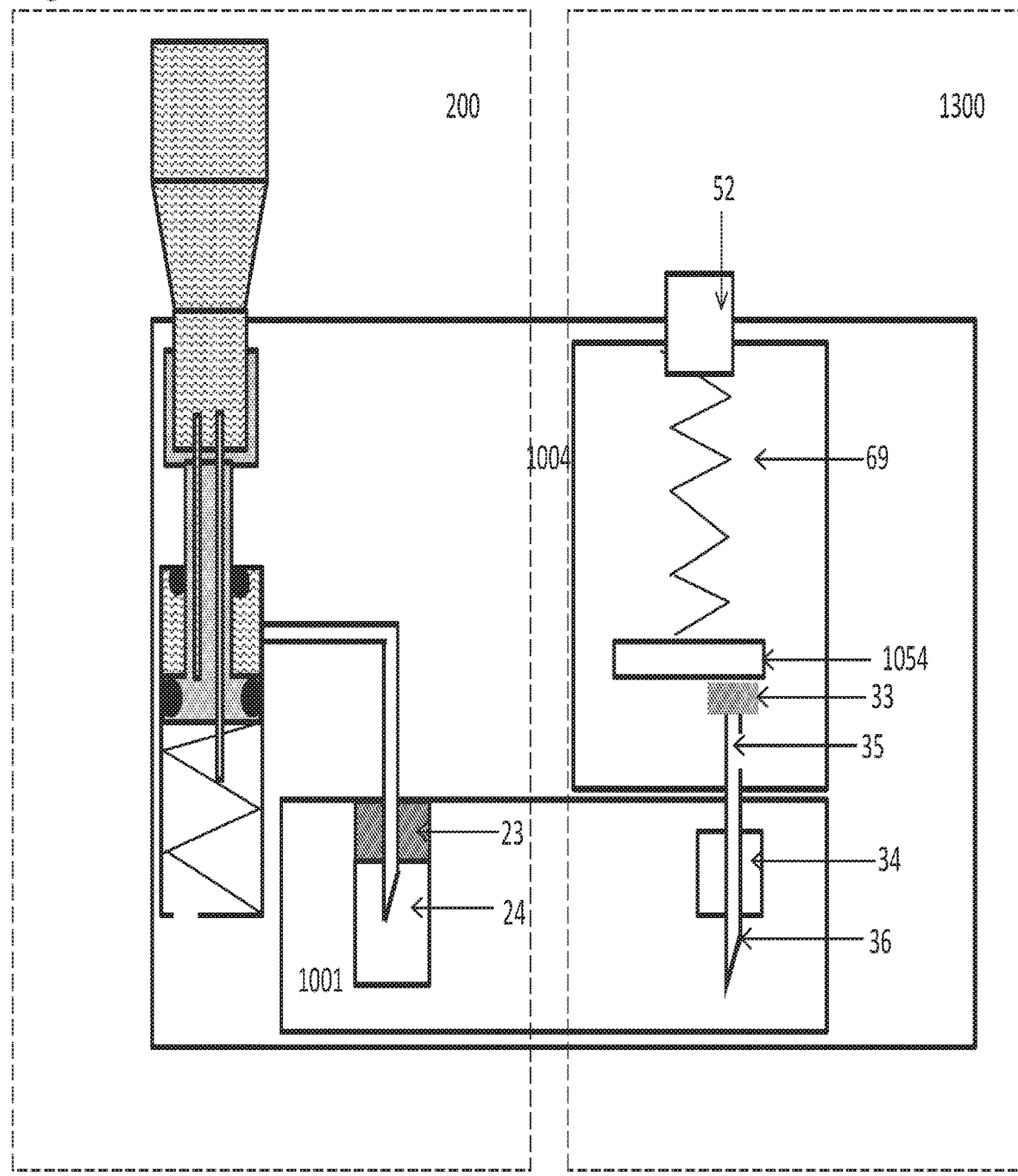
Figure 53:
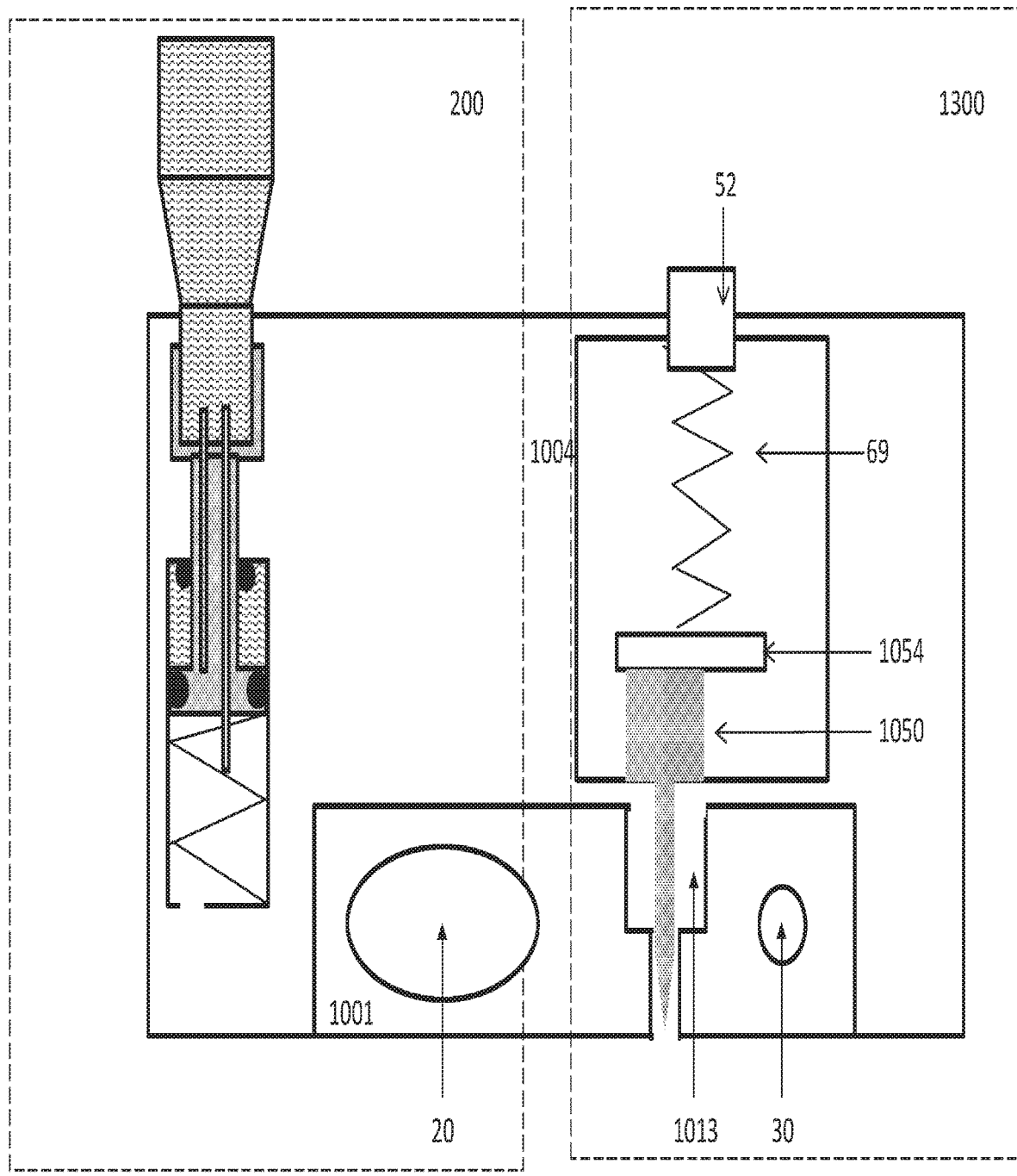

FIGS. 52-53 show schematic cross sections of an assistance device for an artificial pancreas, configured to fill a pump with insulin, and deploy a cannula and a continuous glucose sensor in a user, according to some embodiments.

Figure 54:
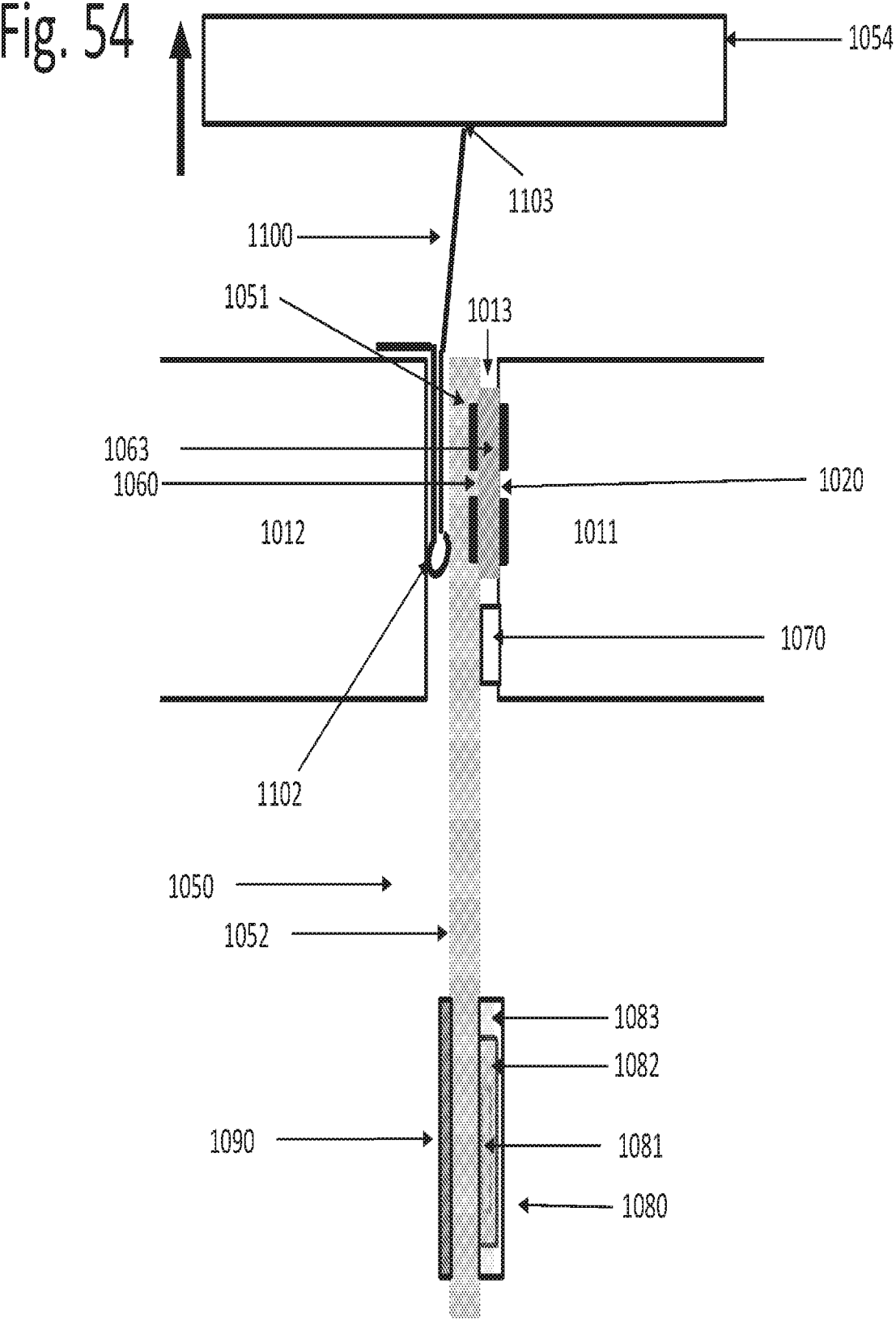

FIG. 54 shows a side view of a continuous glucose sensor of an artificial in the process being electrically and mechanically connected to the pump of the artificial pancreas, according to some embodiments.

Figure 55:
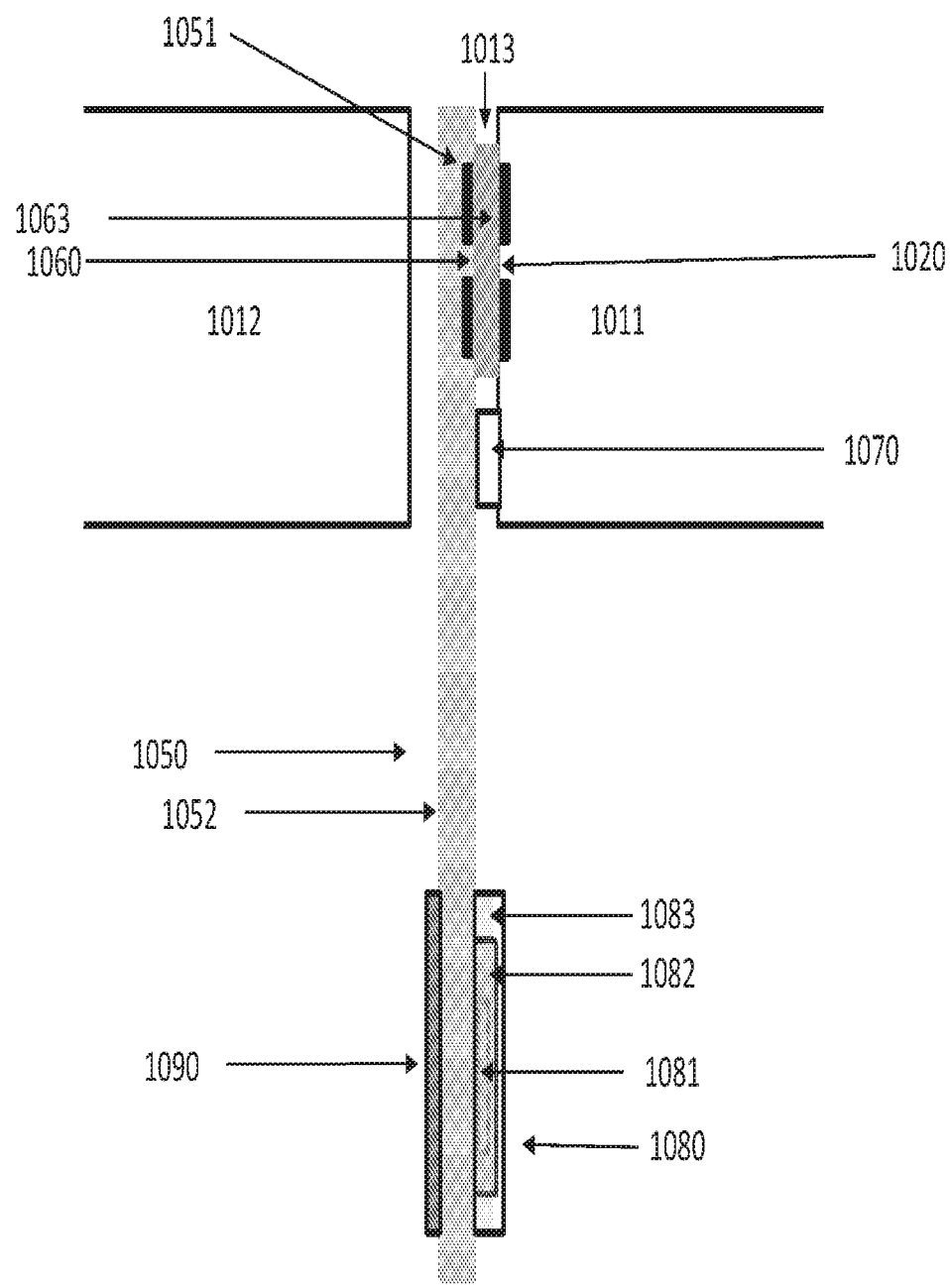

FIG. 55 show a side view of a continuous glucose sensor of an artificial electrically and mechanically connected to the pump of the artificial pancreas, according to some embodiments.

DETAILED DESCRIPTION OF AT LEAST SOME OF THE EMBODIMENTS

Figure 1:
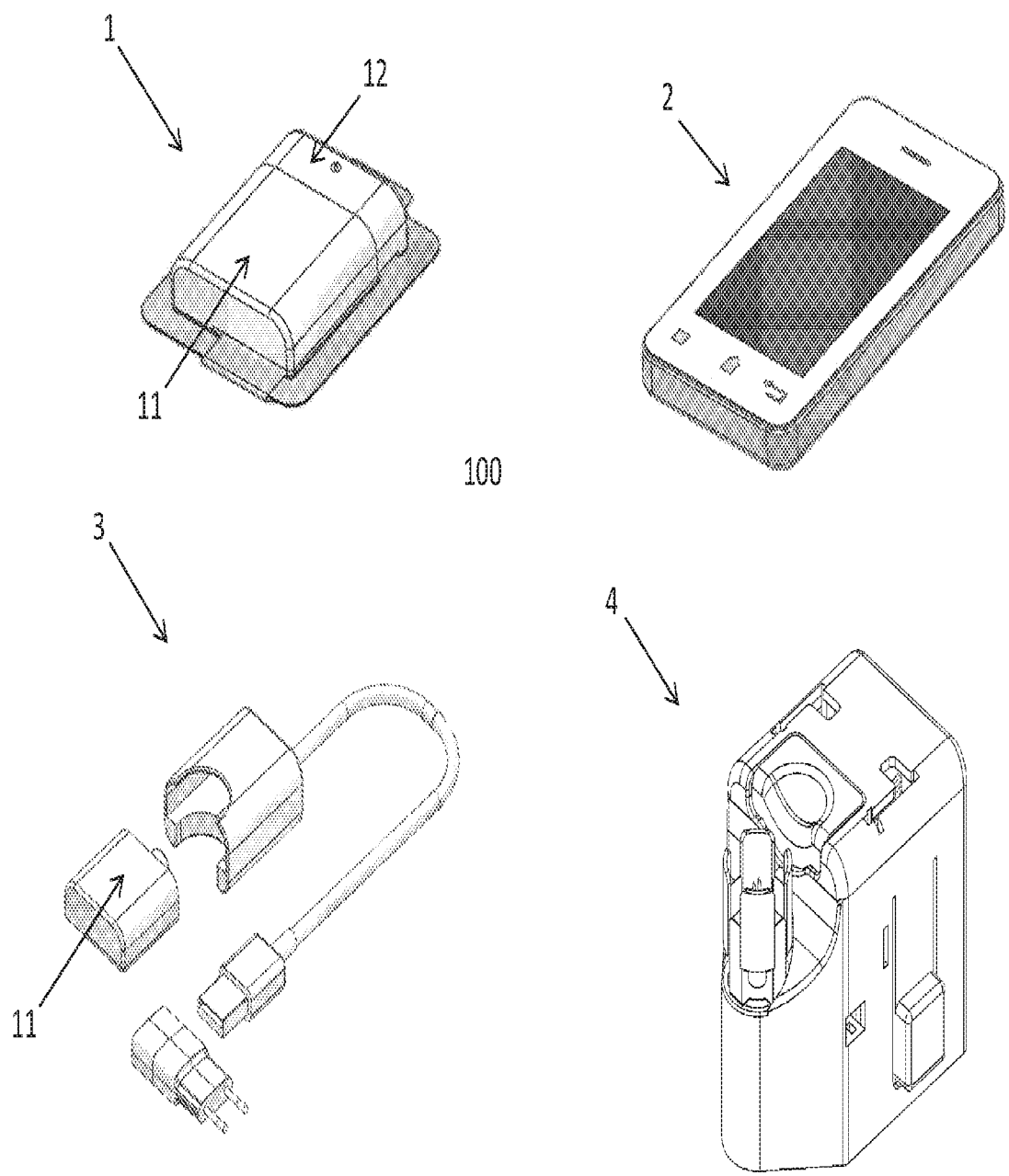
FIG. 1 shows the main or general components of the insulin delivery system ("IDS"), including a patch pump, according to some embodiments.

FIG. 1 shows components of insulin delivery system 100, according to some embodiments of the present disclosure. The system includes at least one of the following components (and in some embodiments, two or more of, and in some embodiments, all of): insulin patch pump 1 (also referred to as a pump, substance delivery pump, drug delivery pump, and the like), controller 2, charger 3, and assistance device 4. In some embodiments, the controller 2 remotely commands the patch pump 1 and receives alerts and alarms from the patch pump 1. The controller 2 can include a user interface(s) such as touch screen and operating buttons. The controller 2 may also communicate with other drug/diabetes management devices (e.g., glucose meters), BLE enabled devices (PC, smartphone, tablets, etc.)

and the cloud. In addition, in some embodiments, the controller may comprise a smartphone and the like.

The patch pump 1, in some embodiments, includes a reusable part (RP) 11 and a disposable part (DP) 12. The RP 11 can include one or more of (and depending upon the embodiments, two or more of, or all of) the driving mechanism, electronics, and power source (e.g., battery). The DP 12 can include all or a plurality of an adhesive base, reservoir, pumping mechanism, filling port, exit port, and a cannula(s).

Insulin (and/or another drug or substance) can be configured for delivery from the reservoir to the exit port, and from the exit port through the cannula into the body (in some embodiments). The power source, within the RP 11 (but in some embodiments, may be included in the DP—and be a single time use battery) may be charged with a charger 3. The assistance device 4 may be used for at least one of: to connect the RP 11 and DP 12, filling the reservoir, adhering the patch pump 1 to the skin, and cannula insertion. After cannula insertion the assistance device 4 can be discarded.

Figure 2:
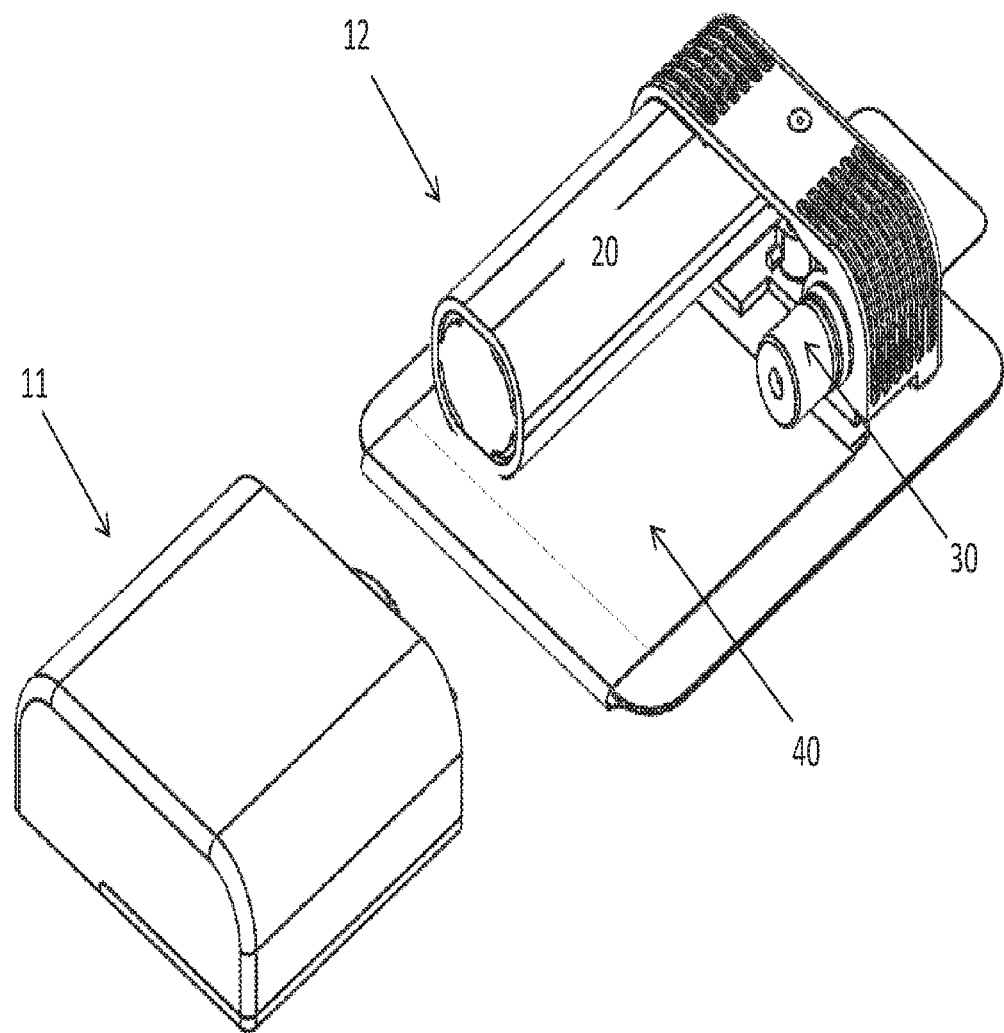
FIG. 2 shows disconnected parts of the patch pump according to some embodiments, including, for example, a disposable part (DP) and a reusable part (RP)

FIG. 2 shows the disconnected components of the patch pump 1: the RP 11 and the DP 12, according to some embodiments. As shown, the DP 12 includes the adhesive base 40, reservoir 20, and doser 30. Insulin can be delivered from the reservoir 20 to the doser 30, and from the doser 30 through the cannula (not shown) into the user's body. According to some embodiments, before operation, the user connects the RP 11 and the DP 12 (forming the patch pump 1), fills the reservoir 20, adheres the patch pump 1 to the skin, and inserts the cannula (not shown). At the end of the operation cycle (from patch pump mounting to patch pump removal, i.e., about 1-5 days), the user removes the patch pump 1 from the skin, disconnects the RP 11 from the DP 12, and disposes the DP 12. In some embodiments, the patch pump may be provided in a kit, which includes at least two RPs 11 so that upon one RP 11 being operated (connected to the DP and adhered to the user body) the second RP 11 is charging. Accordingly, at the end of one operation cycle, a new DP 12 is connected to the charged RP 11 (second RP) and the used RP (first RP) is charged.

FIG. 3 shows a spatial view of the assistance device 4 according to some embodiments. The assistance device 4 may include at least one of (and in some embodiments, two or more of, and in some embodiments, all of) a vial connector 80, RP notch 70, trigger 52, safety catch(es) 51. In one preferred embodiment, the DP (reservoir 20 and adhesive base 40 are shown) is preassembled to the bottom side of the assistance device 4. The adhesive base 40 can includes two adhesive/sticky surfaces, a bottom surface for adhering the patch pump 1 to the skin, and an upper surface for securing the DP 12 to the RP 11 (e.g., after DP-RP connection). The assistance device 4 can include at least one of: a reservoir filling mechanism (200 in FIG. 5), a cannula insertion mechanism (300 in FIG. 5), and DR-RP alignment mechanism. The insertion mechanism may be activated by concomitant pressing on the trigger 52 and safety catches 51 (only one side is shown). The reservoir filling mechanism may be activated by connection of an insulin vial to the vial connector 80 and pressing the vial against the vial connector 80. The RP notch 70 may be configured to provide alignment between the RP 11 and DP 12 during RP-DP connection. The RP 11 (not shown) may be configured to slide over the reservoir 20 and connect to the DP 12 within the assistance device 4.

Figure 4B:
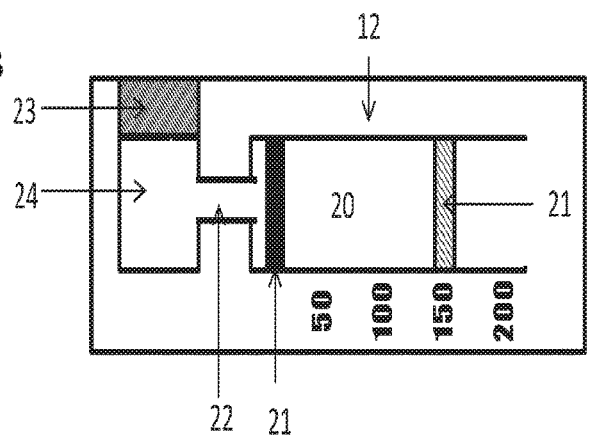
Figure 4A:
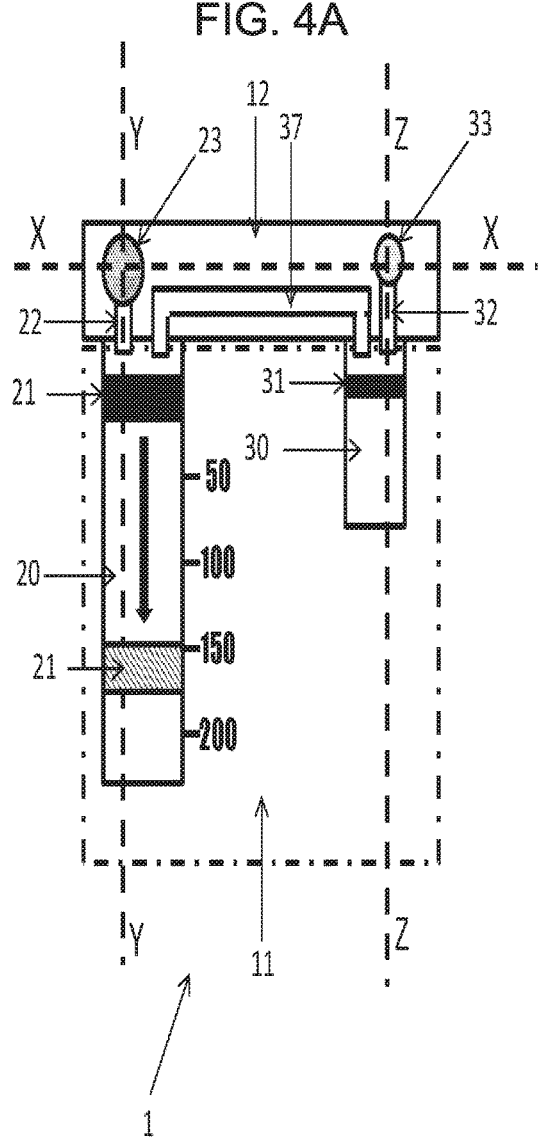

FIGS. 4A-D show the patch pump (A) and cross section views of the DP 12 (B-D), according to some embodiments. FIG. 4A shows the patch pump 1 that includes, for example, the RP 11 (dashed dotted line) and DP 12. The DP 12 can include at least a plurality of (and in some embodiments, all of): reservoir 20, reservoir plunger 21, doser 30, doser plunger 31, filling conduit 22, filling port septum 23, filling port well 24, exit port conduit 32, exit port well 34, cannula 36, cannula septum 33, cannula opening 35, and reservoir-doser conduit 37.

Filling of reservoir 20 (in this case, insulin, but can be any substance for delivery into tissue of a user) may be done with a designated syringe (not shown), or with the assistance device 4 (FIGS. 3 and 5-19). With the syringe, the user draws insulin from a vial, pierces the filling port septum 23 with the syringe needle, and injects insulin into the filling port well 24 and through the filling conduit 22 into the reservoir 20 (i.e. the syringe is a "transporting tool" for insulin delivery from the vial to the patch pump reservoir 20). With the assistance device 4, insulin can be directly delivered from the vial into the patch pump reservoir 20 (no "transporting tool"), insulin is delivered through the filling port septum 23 into the filling port well 24, and through the filling conduit 22 into the reservoir 20.

The amount of insulin that is drawn from the vial and injected into the reservoir 20 can depend on the user's insulin daily consumption and the predicted days of use. For example, if the daily consumption is 50 units/day (50 U/day) and the replacement cycle (time between replacements) is 3 days, the total required insulin amount is 150 U (50 U×3 days). Insulin is delivered from the well 24, through the filling conduit 22 into the reservoir 20. During reservoir 20 filling, the reservoir plunger 21 is displaced in the direction of the bold arrow to its final position (downward diagonal lines). The final position of the reservoir plunger 21 is configured to depend on the amount of insulin that the user injects into the reservoir 20. In FIG. 4A, the reservoir may be marked with four graduations (50 U, 100 U, 150 U, and 200 U), the reservoir is filled with 150 U and the final position of the reservoir plunger 21 (downward diagonal lines) is at the mark of 150 U.

During patch pump 1 operation, the doser plunger 31 can be configured to be displaced backward and forward by the RP driving mechanism (not shown). When the doser plunger 31 is displaced backward, insulin can be delivered through the reservoir-doser conduit 37 into the doser 30. When the doser plunger 31 is displaced forward, insulin can be delivered from the doser 30 through the exit port conduit 32, exit port well 34, cannula opening 35, and cannula 36 into the user's body.

Figure 4C:
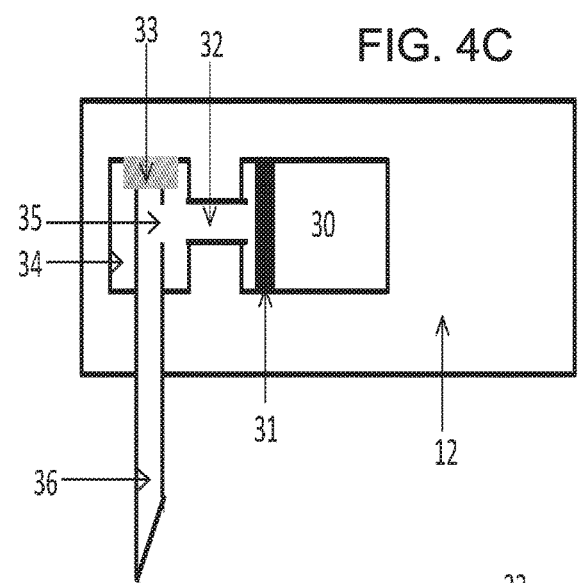
Figure 4D:
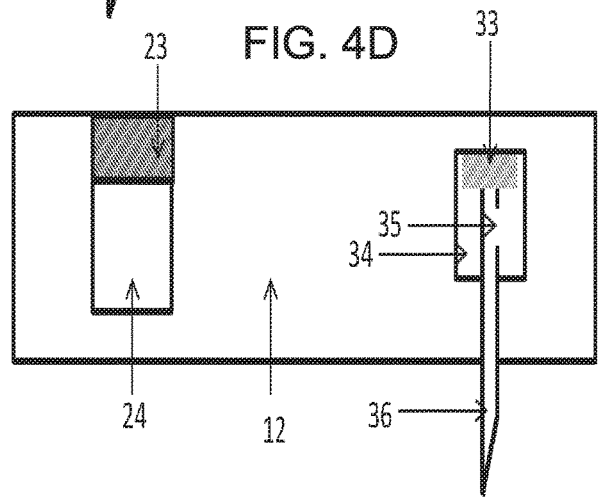

FIGS. 4B, 4C, and 4D show cross section views of the DP 12 through cross section planes (dotted lines) y-y (4B), z-z (4C), and x-x (4D), respectively. FIG. 4B shows a longitudinal cross section view of plane y-y of FIG. 4A. The DP 12 includes the reservoir 20, reservoir plunger 21 (before filling—black, and after filling with 150 U of insulin—downward diagonals), filling conduit 22, filling port septum 23, and filling port well 24. FIG. 4C shows a longitudinal cross section view of plane z-z of FIG. 4A (after cannula 36 insertion). The DP 12 includes the doser 30, doser plunger 31, exit port conduit 32, exit port well 34, cannula 36, cannula septum 33, and cannula opening 35. During insulin administration to the user, insulin can be delivered from the doser 30 through the exit port conduit 32, exit port well 34, cannula opening 35, and cannula 36 into the user's body. Before insertion of cannula 36 (FIG. 5), the cannula septum 33 and cannula opening 35 are situated externally to the DP 12 and the cannula 36 tip is situated within the DP 12. In some embodiments, the DP 12 can be preassembled with the assistance device (FIGS. 3, 5-8, and 19), and after reservoir 20 filling and DP-RP connection (within the assistance device), the patch pump 1 is adhered to the user's skin with the assistance device and the cannula 36 is inserted by activation of the cannula insertion mechanism (FIG. 19).

In some embodiments, during cannula insertion, the cannula 36, and cannula opening 35 are downwardly displaced to the position shown in FIG. 4C—cannula septum 33 is sealing the exit port well 34, cannula opening 35 is situated within the exit port well 34, and the tip of cannula 36 is situated below the bottom of the DP 12. FIG. 4D shows a transverse cross section view of plane x-x of FIG. 4A. The DP 12 includes the filling port septum 23, filling port well 24, exit port well 34, cannula 36, cannula septum 33, and cannula opening 35.

FIG. 5 shows a scheme of the main components of the assistance device 4 and the preassembled DP 12. In some embodiments, the assistance device 4 can include at least one of the reservoir filling mechanism 200, and the cannula insertion mechanism 300. In another embodiment (not shown), insulin filling and cannula insertion can be performed with two separated devices, a filling device and an insertion device (inserter), where each device can have (and in some embodiments has) a separate housing. The filling device can be configured with a reservoir filling mechanism 200, and the insertion device has a cannula insertion mechanism 300. Hereinafter, the reservoir filling mechanism 200, with respect to at least one and/or another of embodiments of the disclosure, may interchangeably be part of the assistance device 4 (including the insertion mechanism 300) or a standalone filling device having a separate housing and a separate reservoir filling mechanism 200.

The assistance device 4 shown in FIG. 5 includes the preassembled DP 12, the reservoir filling mechanism 200, and the cannula insertion mechanism 300. The reservoir filling mechanism 200 may include at least one of (and in some embodiments, two or more of, and in some embodiments, all of) the vial adaptor 41, filling needle 43, venting needle 44, filling piston 42, filling interspace 48, transferring needle 47, piston spring 45, and venting aperture 46. The cannula insertion mechanism 300 may include trigger 52, inserter spring 69, and inserter hammer 54. The DP 12 may include the filling port septum 23, filling port well 24, exit port well 34, cannula 36, cannula septum 33, and cannula opening 35. Accordingly, after cannula insertion, the cannula septum 33 is configured to seal exit port well 34, cannula opening 35 is situated within the exit port well 34, and tip of cannula 36 is situated below the bottom of the DP 12 (FIG. 4C). FIG. 5 shows the reservoir filling mechanism 200 during the interspace 48 filling phase (phase 3, FIGS. 8A and 12), the vial 50 is connected to the vial adaptor 41 and insulin is delivered from the vial 50 into the interspace 48. The transferring needle 47 pierces the filling port septum 23 and the tip of the transferring needle 47 is position within the filling port well 34.

FIGS. 6, 7A-B, and 8A-B show spatial views of the assistance device 4 (FIG. 6) and the operation phases of the reservoir filling mechanism (FIGS. 7A-B and 8A-B), according to some embodiments. First, vial connection (7A)—vial 50 is connected to the vial adaptor 41, second, interspace filling (7B)—vial is pressed downward and insulin is delivered from the vial into the interspace 48. Third, reservoir filling (8A)—pressure is removed from the vial 50, vial 50 is retracted, and insulin is delivered from the interspace 48 to the reservoir 20. Four, Vial disconnection (8B)—vial 50 is removed from the assistance device 4.

Figure 6:
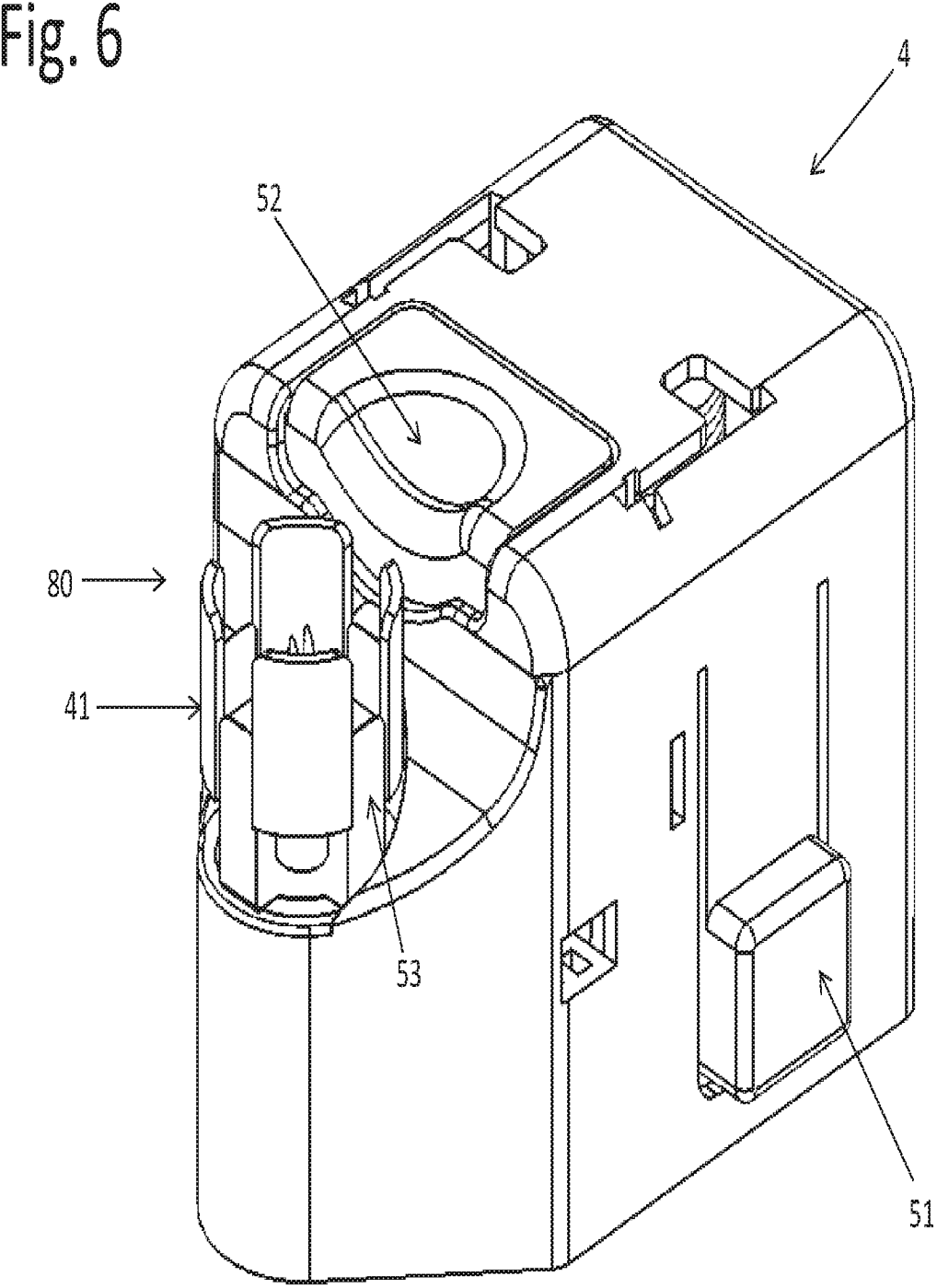

FIG. 6 shows a spatial view of the assistance device 4 according to some of the embodiments. The assistance device 4 includes the trigger, 52, safety catches 51, and vial connector 80. The vial connector 80 may comprise the vial adaptor 41 and the needles protector 53.

Figure 7A:
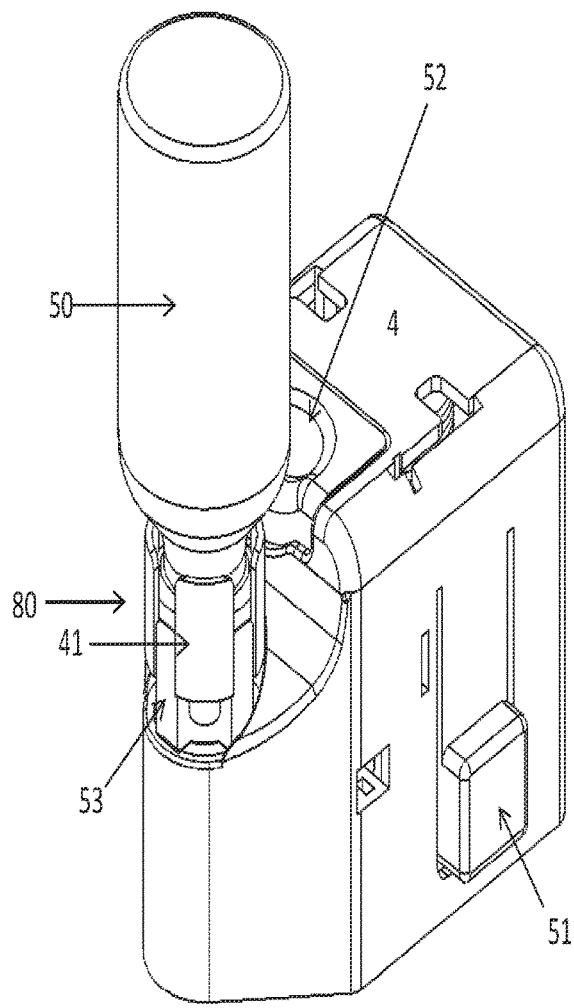

FIG. 7A shows a spatial view of the assistance device 4 at phase 1 of the reservoir filling (vial connection), according to some embodiments. The assistance device includes the trigger, 52, safety catches 51, and vial connector 80 (vial adaptor 41 and the needles protector 53). During phase 1 of reservoir filling, the vial 50 is connected to the vial adaptor 41 (operation scheme in FIG. 10).

Figure 7B:
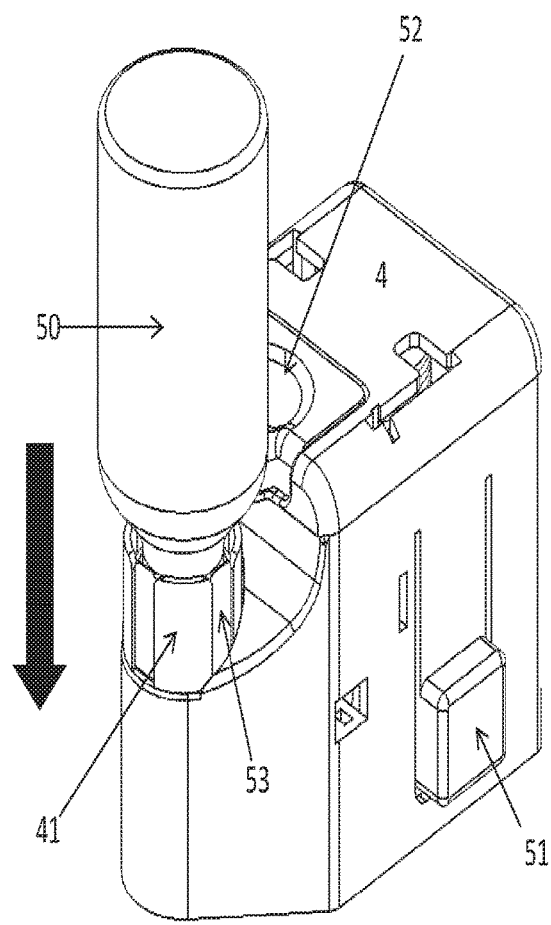

FIG. 7B shows a spatial view of the assistance device 4 at phase 2 of the reservoir filling (interspace filling), according to some embodiments. The assistance device may include trigger 52, safety catche(s) 51, and vial connector 80 (vial adaptor 41 and the needles protector 53). During phase 2 of reservoir filling, the vial 50 may be forced downward in the direction of the bold arrow. Insulin may now be delivered from the vial 50 into the interspace 48 (operation scheme in FIG. 11).

FIG. 8A shows a spatial view of the assistance device 4 at phase 3 of the filling process (reservoir filling), according to some embodiments. The assistance device 4 includes trigger 52, safety catches 51, and vial connector 80 (vial adaptor 41 and needles protector 53). During phase 3 of filling process, the vial 50 can be retracted in the direction of the bold arrow. Insulin is delivered from the interspace 48 into the reservoir 20 (operation scheme in FIG. 12).

FIG. 8B shows a spatial view of the assistance device 4 at phase 4 of the filling process (vial disconnection), according to some embodiments. The assistance device 4 includes trigger, 52, safety catches 51, and vial connector 80 (vial adaptor 41 and needles protector 53). During phase 4 of the filling process, the vial 50 is removed from the assistance device 4 (operation scheme in FIG. 13).

Figure 9:
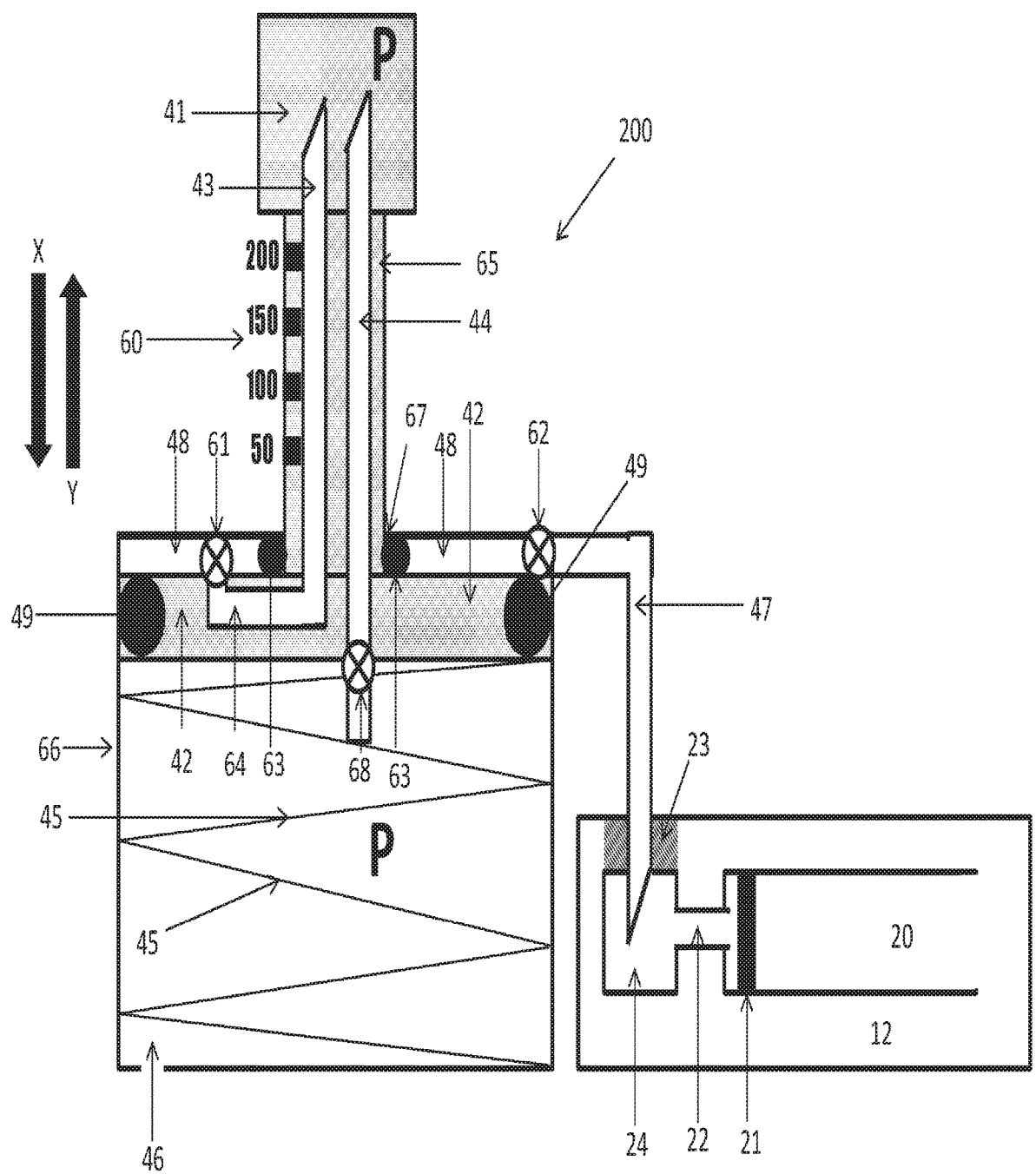

FIGS. 9-14 show schemes of the reservoir filling mechanism 200 of the assistance device 4 (FIG. 9) and the operation phases (phase 1→phase 4) of the reservoir filling (FIGS. 10-14), according to some embodiments. FIG. 9 shows a scheme of a cross section of the reservoir filling mechanism 200. The reservoir filling mechanism 200 may include a plurality of, and preferably all of, the vial adaptor 41, sliding rod 65, sliding rod opening 67, filling needle 43, venting needle 44, filling piston 42, filling interspace 48, piston conduit 64, transferring needle 47, piston gasket 49, interspace gasket 63, first unidirectional valve 61, second unidirectional valve 62, third unidirectional valve 68, transferring needle 47, graduation marks 60, filling sleeve 66, piston spring 45, and venting aperture 46. In some embodiments, the reservoir filling mechanism 200 can be preassembled with the DP 12 within the assistance device 4 (not shown).

The DP 12 may also include a plurality of and preferably all of the filling port septum 23, filling port well 24, filling conduit 22, reservoir 20, and reservoir plunger 21. The transferring needle 47 is configured to pierce the filling port septum 23, with the tip of the transferring needle 47 residing within the filling port well 24. The vial adaptor 41 may be connected with the filling piston 42 via the cylindrically shaped sliding rod 65. The filling sleeve 66 may comprise at least one of, and in some embodiments, a plurality of, and in some embodiments, all of, a cylinder that can include a plurality of and preferably all of the piston spring 45, filling piston 42, venting aperture 46, and filling sleeve opening 67. The interspace gasket 63 may be connected to the filling sleeve opening 67 providing sealing of the interspace 48 when the sliding rod 65 is linearly displaced (in the direction of the bold arrows X and Y) within the filling sleeve opening 67. The filling piston 42 may include a gasket 49 that provides sealing of the interspace 48 when the filling piston 42 is linearly displaced within the filling sleeve 66. Displacement of the filling piston 42 in the direction of the bold arrow X is configured to increase the volume of the interspace 48 and compresses the piston spring 45, displacement of the filling piston 42 in the direction of the bold arrow Y decreases the volume of the interspace 48 and decompressed the piston spring 45. The filling needle 43 preferably includes a sharp tip and traverses the sliding rod 65. The filling needle 43 may include one-way hydraulic communication with the interspace 48 via the piston conduit 64 that traverses the filling piston 42.

The first unidirectional valve 61 provides one way of insulin delivery from the tip of the filling needle 43 through the piston conduit 64 to the interspace 48. The interspace 48 preferably includes a one-way hydraulic communication with the reservoir 20 via the transferring needle 47, filling port well 24, reservoir filling conduit 22, and the reservoir 20. The second unidirectional valve 62 preferably provides one way of insulin delivery from the interspace 48 to the reservoir 20 via the transferring needle 47, filling port well 24, and reservoir filling conduit 22. The venting needle 44 preferably includes a sharp tip and transverses the sliding rod 65. The venting needle 44 is configured to provide air communication between the filling sleeve 66 and the tip of the venting needle 44. In some embodiments, a third unidirectional valve 68 can be provided, which may be arranged at the end of the venting needle 44 within the piston sleeve 66. The third unidirectional valve 68 is configured to provide one-way air delivery from the atmosphere into the vial 50 and prevents inadvertent insulin delivery if the pressure within the vial 50 is above atmospheric pressure (this can happen if, for example, the vial was filled with air by using a syringe for reservoir filling).

Figure 11:
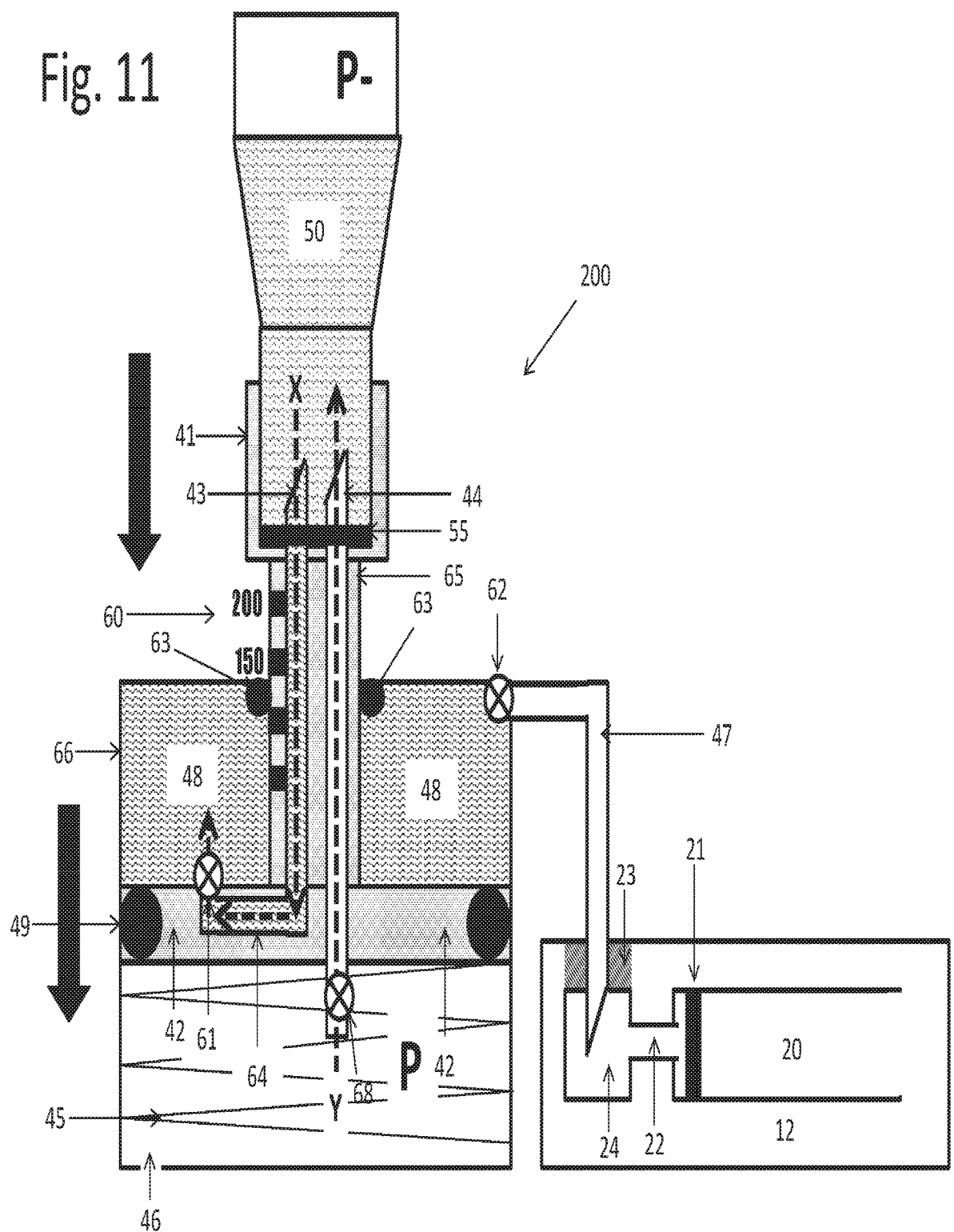

The venting aperture 46 is configured to provide atmospheric pressure (P) equilibrium between the atmosphere and the filling sleeve 66. When the vial is not connected to the vial adaptor 41, the pressure at the tip of the venting needle 44 is atmospheric pressure (P) and there is no air movement along the venting needle 44. The sliding rod 65 is preferably configured with graduation marks 60 that provide the user with an indication of the volume of insulin that is delivered from the vial 50 into the reservoir 20 (according to the required insulin consumption during the operation cycle (i.e. 1-5 days). FIG. 9 shows an example of marks—50, 100, 150, and 200 insulin units. During the filling process, the user presses the vial 50 and displaces the vial adaptor 41 and the sliding rod 65 in the direction of the bold arrow X. The extent of displacement (linear movement of the sliding rod 65 and the filling piston 42) is configured to correlate with the amount of insulin delivered from the vial 50 into the reservoir 20. For example—if the required amount is 150 units (150 U), the user presses the vial 41 and the sliding rod 65 to the level of the 150 units mark. In another embodiment, the reservoir filling mechanism 200 can be provided with a volume setting knob (not shown) that is positioned on the sliding rod 65. Rotation of the knob by the user in one direction or the opposite direction (e.g., clockwise or counterclockwise) increases or decreases the insulin amount to be delivered respectively. The graduations can be marked on the knob (i.e. 0 U-200 U). The user rotates the volume setting knob to the desired amount (i.e. 150 units) and presses the vial 50 (FIG. 11). In another preferred embodiment, the amount of insulin delivered from the vial 50 into the reservoir 20 can be preset to a fixed quantity (i.e. 50 insulin units). The extent of downward displacement (bold arrow X) of the sliding rod 65 can be preset and accordingly the amount of insulin delivered from the vial 50 into the reservoir 20 in one press is preset. The total amount of delivered insulin=Quantum (in insulin units)×number of presses. For example, if the fixed quantum is 50 units (50 U) and the user requirement for one replacement cycle (i.e. 1-5 days) is 150 units (150 U), the user should press the vial 3 times (50 U×3=150 U). In the example shown in FIG. 9, if the maximal volume of the reservoir is 200 U, then, accordingly, for achieving a full reservoir, the maximal number of presses is 4 (50 U×4=200 U).

Figure 10:
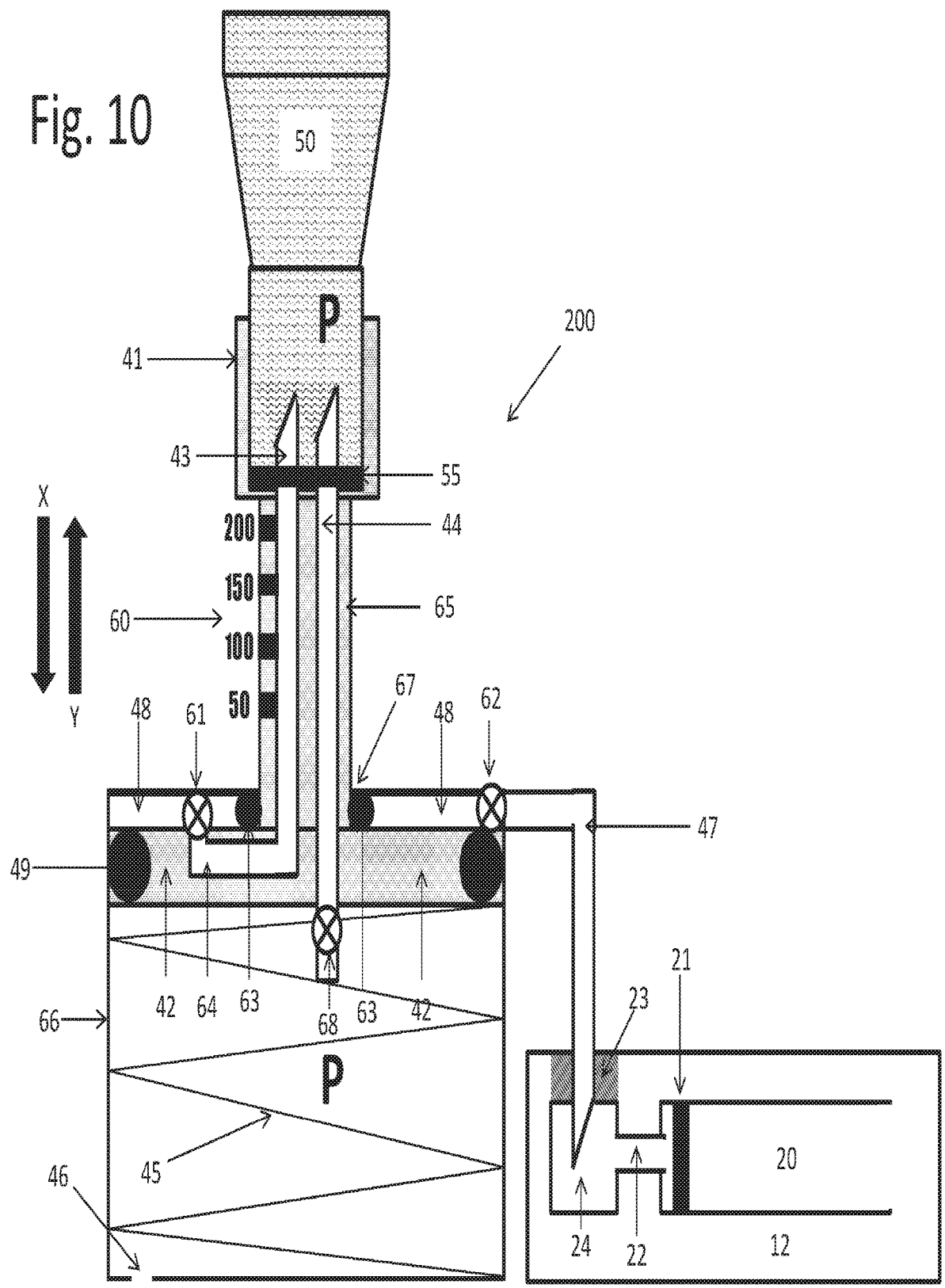

FIG. 10 shows a cross-section of the reservoir filling mechanism 200 at phase 1 of the filling process (vial connection), according to some embodiments. The reservoir filling mechanism 200 includes a plurality of, and preferably all of, the vial adaptor 41, sliding rod 65, sliding rod opening 67, filling needle 43, venting needle 44, filling piston 42, filling interspace 48, piston conduit 64, transferring needle 47, piston gasket 49, interspace gasket 63, first unidirectional valve 61, second unidirectional valve 62, third unidirectional valve 68, transferring needle 47, graduation marks 60, filling sleeve 66, piston spring 45, and venting aperture 46. The reservoir filling mechanism 200 provides delivery of insulin from the vial 50 to the reservoir 20 (that resides within the DP 12) through the transferring needle 47. The DP 12 includes a plurality of, and preferably all of, the filling port septum 23, filling port well 24, filling conduit 22, reservoir 20, and reservoir plunger 21. At phase 1 of the filling process, the vial 50 is connected to the vial adaptor 41. The filling needle 43 and venting needle 44 pierce the rubber septum of the vial cover 55.

FIG. 11 shows a scheme of a cross section of the reservoir filling mechanism 200 at phase 2 of the filling process (interspace filling), according to some embodiments. The reservoir filling mechanism 200 includes a plurality of, and preferably all of, the vial adaptor 41, sliding rod 65, sliding rod opening 67, filling needle 43, venting needle 44, filling piston 42, filling interspace 48, piston conduit 64, transferring needle 47, piston gasket 49, interspace gasket 63, first unidirectional valve 61, second unidirectional valve 62, third unidirectional valve 68, transferring needle 47, graduation marks 60, filling sleeve 66, piston spring 45, and venting aperture 46. The DP 12 includes a plurality of, and preferably all of, the filling port septum 23, filling port well 24, filling conduit 22, reservoir 20, and reservoir plunger 21. At phase 2 of the filling process, the vial 50 is pressed in the direction of the bold arrow, and, concomitantly, the sliding rod 65 and the filling piston 42 are displaced in the same direction (bold arrow). The displacement of the filling piston 42 creates a negative pressure within the interspace 48 that is hermetically sealed by the piston gasket 49 and interspace gasket 63. Insulin (wavy lines) in the vial 50 follows the pressure gradient and is delivered in the direction of the dashed line arrow X through the filling needle 43, piston conduit 64, and first unidirectional valve 61 into the interspace 48.

In the example of FIG. 11, the sliding rod 65 can be displaced to the 150 units mark, and accordingly, the interspace 48 is filled with 150 units of insulin. During displacement of the filling piston 42, the piston spring 45 is compressed. The second unidirectional valve 62 can be configured to prevent air from getting into the interspace and creating air bubbles. During insulin delivery from the vial 50 into the interspace 48, the pressure within the vial 50 drops below the atmospheric pressure (P−). Following the pressure drop (P−) within the vial, air follows the pressure gradient and is delivered in the direction of the dashed line arrow Y from the filling sleeve 66 through the venting needle 44 and into the vial 50 through optional third valve 68. At the end of filling phase 2, the pressure within the vial 50 is the atmospheric pressure.

Figure 12:
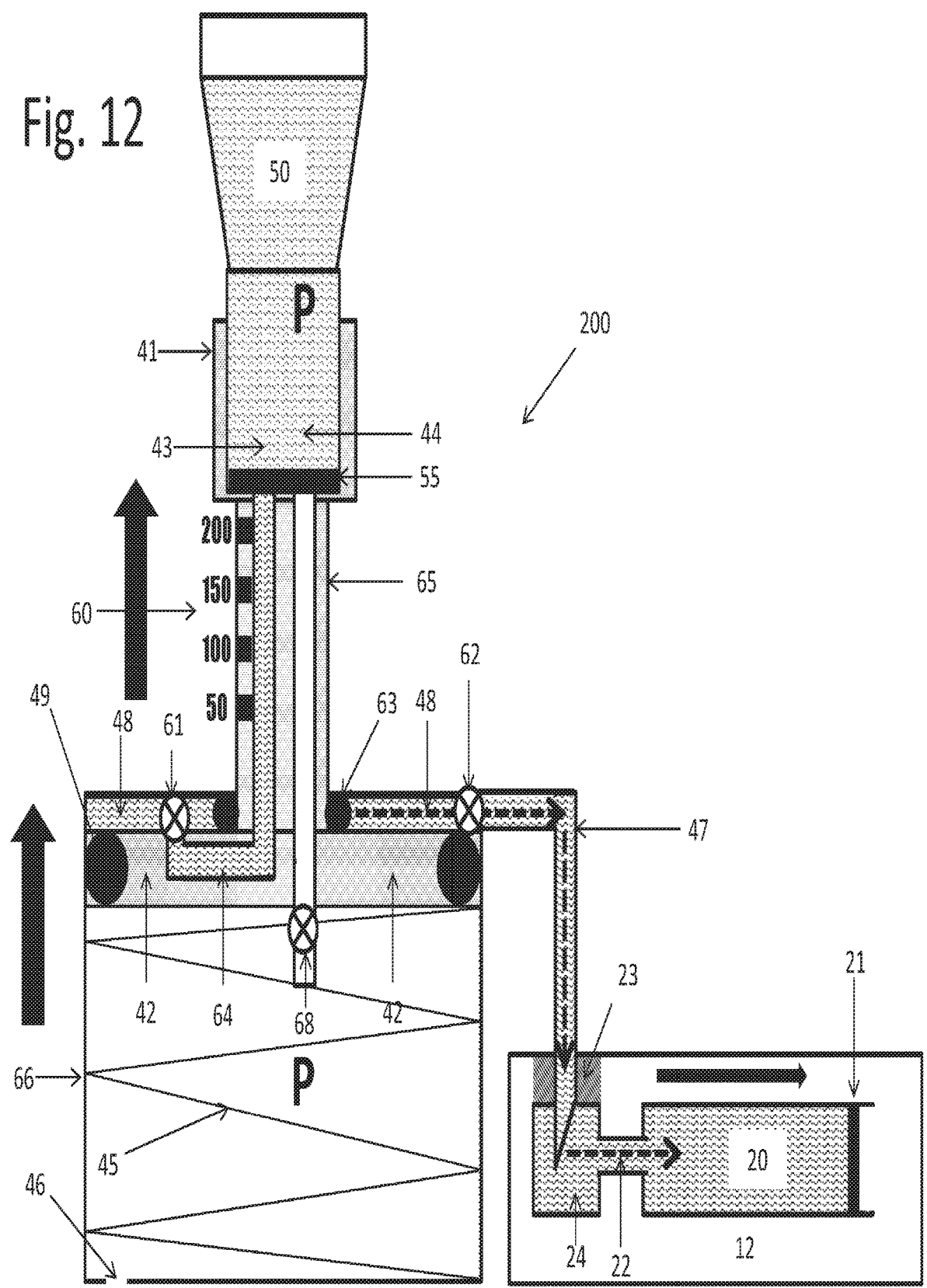

FIG. 12 shows a scheme of a cross section of the reservoir filling mechanism 200 at phase 3 of the filling process (reservoir filling), according to some embodiments. The reservoir filling mechanism 200 includes a plurality of, and preferably all of, the vial adaptor 41, sliding rod 65, sliding rod opening 67, filling needle 43, venting needle 44, filling piston 42, interspace 48, piston conduit 64, transferring needle 47, piston gasket 49, interspace gasket 63, first unidirectional valve 61, second unidirectional valve 62, transferring needle 47, graduation marks 60, filling sleeve 66, piston spring 45, and venting aperture 46. The DP 12 includes a plurality of, and preferably all of. The filling port septum 23, filling port well 24, filling conduit 22, reservoir 20, and reservoir plunger 21. At phase 3 of the filling process, the pressure applied by the user on the vial 50 is removed, releasing stored energy within the compressed piston spring 45. The filling piston 42, sliding rod 65, and vial adaptor 41 are displaced in the direction of the bold arrows. The movement of the filling piston 42 decreases the volume of the interspace 48 and insulin that was momentarily stored in the interspace 48 is displaced from the interspace 48 and delivered in the direction of the dashed line arrow X through the second unidirectional valve 62, transferring needle 47, filling port well 24, filling conduit 22 and into the reservoir 20. During the reservoir 20 filling, the reservoir plunger 21 is displaced in the direction of the thin arrow towards the rear side of the reservoir 20. The first unidirectional valve 61 can be configured to prevent reverse insulin delivery from the interspace 48 into the insulin vial. The pressure (P) within the vial 50 remains equal to the atmospheric pressure within the filling sleeve 66.

Figure 13:
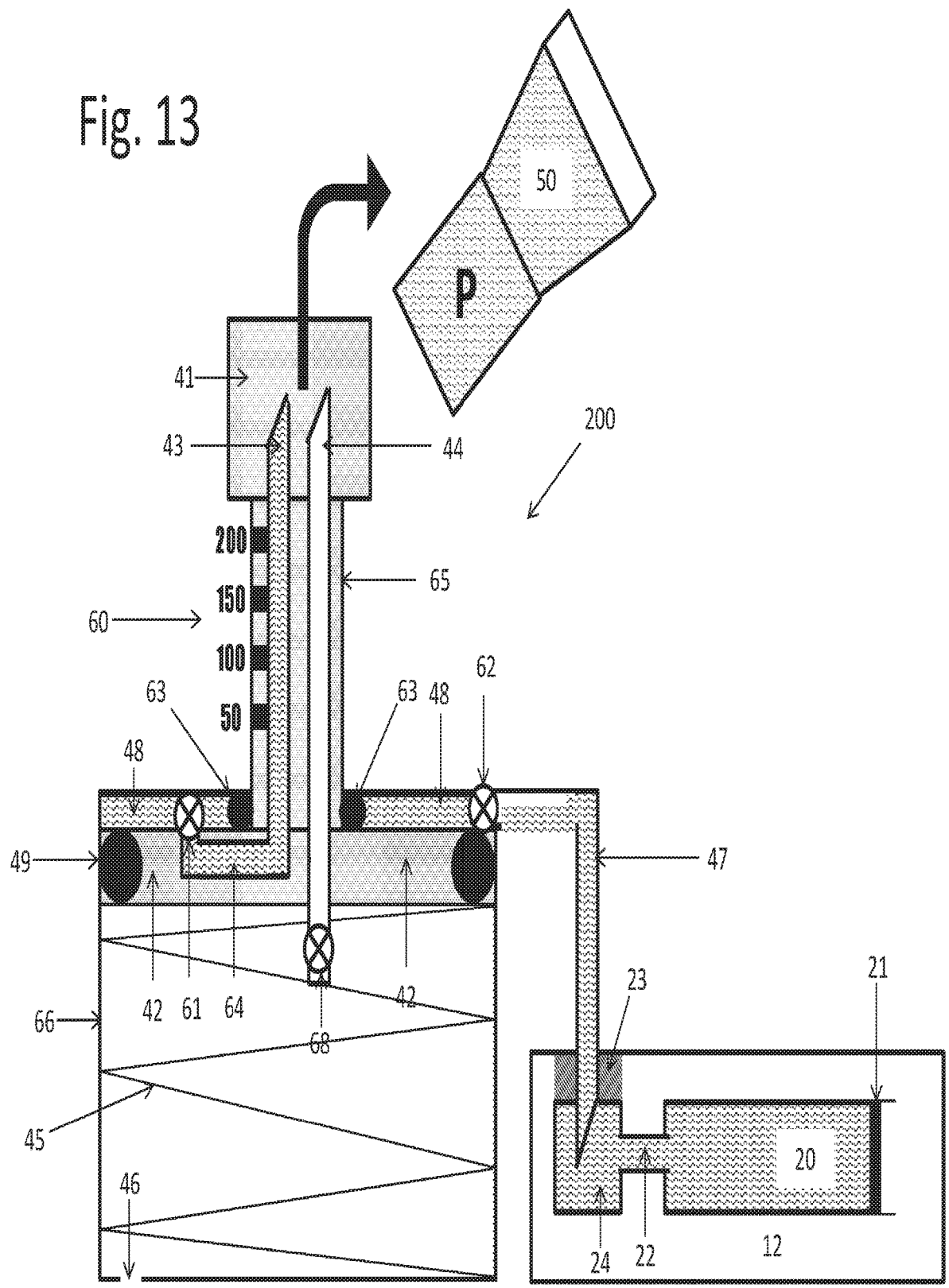

FIG. 13 shows a scheme of a cross section of the reservoir filling mechanism 200 at phase 4 of the filling process (vial disconnection), according to some embodiments. The reservoir filling mechanism 200 includes a plurality of, and preferably all of, the vial adaptor 41, sliding rod 65, filling needle 43, venting needle 44, filling piston 42, interspace 48, piston conduit 64, transferring needle 47, piston gasket 49, interspace gasket 63, first unidirectional valve 61, second unidirectional valve 62, third unidirectional valve 68, transferring needle 47, graduation marks 60, filling sleeve 66, piston spring 45, and venting aperture 46. The DP 12 includes a plurality of, and preferably all of, the filling port septum 23, filling port well 24, filling conduit 22, reservoir 20, and reservoir plunger 21. At phase 4 of the filling process the vial 50 is removed (curved bold arrow). The pressure within the removed vial 50 is equal to the atmospheric pressure and the vial 50 is ready for another filling cycle.

Figure 14:
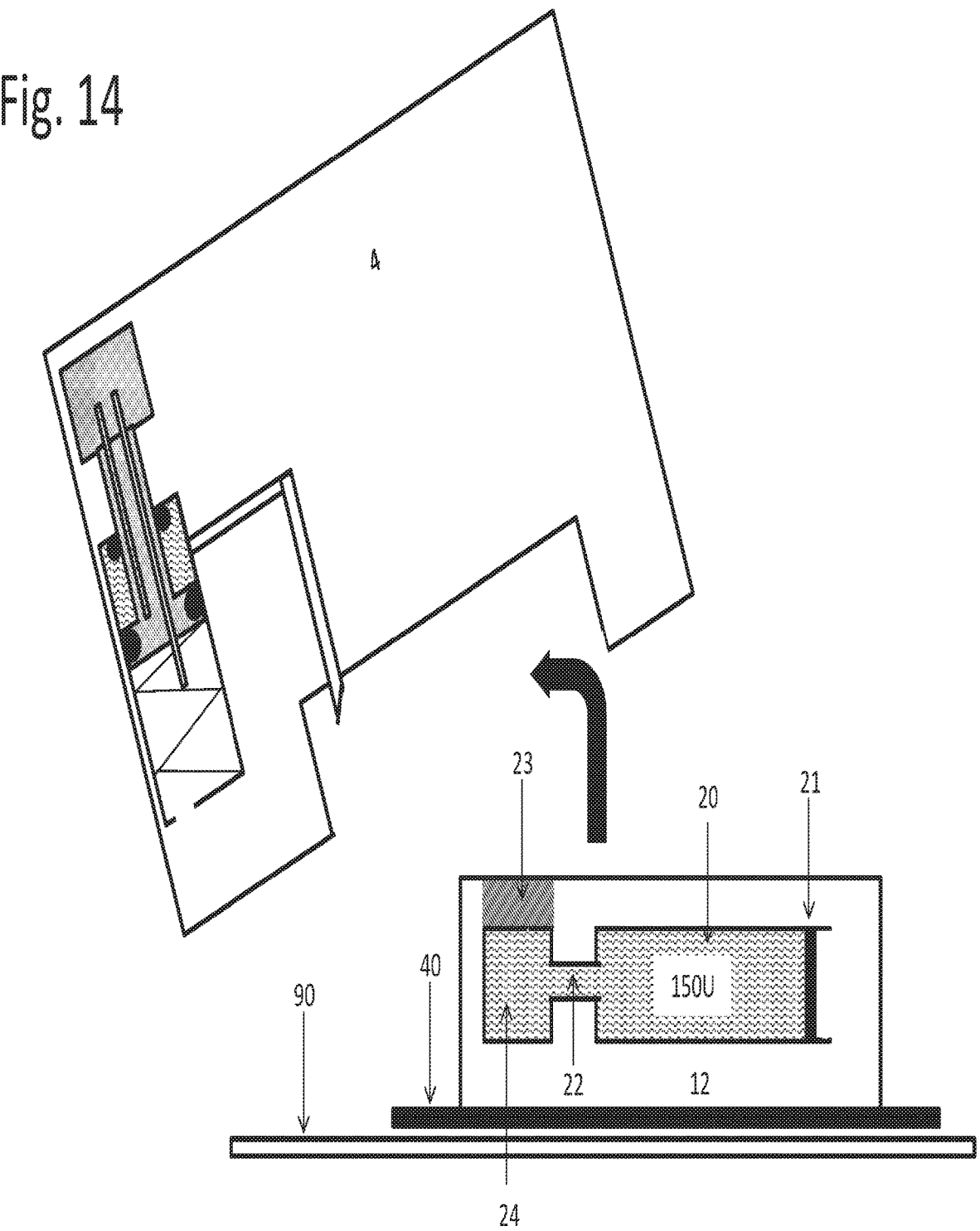

FIG. 14 shows a scheme of a cross section of the DP 12 after completion of the filling process and after cannula insertion and removal of the assistance device 4 from the user skin 90 (cannula insertion mechanism, cannula insertion, and the cannula are not shown), according to some embodiments. The DP 12 can include a plurality of, and preferably all of, the adhesive base 40, filling port septum 23, filling port well 24, filling conduit 22, reservoir 20, and reservoir plunger 21. The reservoir 20 is filled (waves) and the reservoir plunger 21 is at the rear position. The reservoir is filled with 150 units of insulin (150 U) (as shown in the examples mentioned in FIGS. 10-12).

FIGS. 15-16 show cross-section views of the reservoir filling mechanism 200 and the DP 12 (FIG. 15) and the standalone reservoir filling mechanism 200 (FIG. 16), according to some embodiments. FIG. 15 shows a cross-section view of the reservoir filling mechanism 200 and the DP 12. The reservoir filling mechanism 200 can include a plurality of, and preferably all of, the vial adaptor 41, needles protector 53, sliding rod 65, filling needle 43, venting needle 44, filling piston 42, interspace 48, piston conduit 64, transferring needle 47, piston gasket 49, interspace gasket 63, first unidirectional valve 61, second unidirectional valve 62, transferring needle 47, filling sleeve 66, piston spring 45, and venting aperture 46. The DP 12 includes a plurality of, and preferably all of, the filling port septum 23, filling port well 24, filling conduit 22, reservoir 20, and reservoir plunger 21. The needles protector 53 may comprise a petal-like shaped spring with banding "leaves" (e.g., one or more leaves). In some embodiments, four leaves are interposed within the vial adaptor 41, each comprising a "leaf" (e.g., four leaves), preferably a rigid leaf (spatial views in FIGS. 6-8). The vial adaptor 41 may be displaced linearly down and up (bold arrows X and Y) relative to the needle protector 43. Before connection of the vial 50 to the vial adaptor 41, the leaves of the needle protector are parallel to the filling needle 43 and the venting needle 44. After vial 50 removal, the leaves of the needles protector 53 and reconfigured to bend over both needles 43 and 44, thereby protecting the user from inadvertent self-pricking (FIG. 18).

FIG. 16 shows a magnified cross section view of the reservoir filling mechanism 200 before vial connection, according to some embodiments. The reservoir filling mechanism 200 includes a plurality of, and preferably all of, the vial adaptor 41, needles protector 53, sliding rod 65, filling needle 43, venting needle 44, filling piston 42, interspace 48, piston conduit 64, transferring needle 47, piston gasket 49, interspace gasket 63, first unidirectional valve 61, second unidirectional valve 62, transferring needle 47, filling sleeve 66, piston spring 45, and venting aperture 46. Leaves of the needles protector 53 are shown before vial 50 connection (continuous lines 53) and after vial 50 disconnection (dashed lines 53).

FIGS. 17A-C show cross section views of the reservoir filling mechanism 200 at first three phases of the filling process, according to some embodiments: phase 1—vial connection (17A), phase 2—interspace filling (17B), and phase 3—reservoir filling (17C). FIGS. 17A-C (cross section views) correspond to FIGS. 10-12 (schemes) respectively: FIG. 17A—FIG. 10, FIG. 17B—FIG. 11, and FIG. 17C—FIG. 12. The reservoir filling mechanism 200 includes a plurality of, and preferably all of, the vial adaptor 41, needles protector 53, sliding rod 65, filling needle 43, venting needle 44, filling piston 42, interspace 48, piston conduit 64, transferring needle 47, piston gasket 49, interspace gasket 63, first unidirectional valve 61, second unidirectional valve 62, optional third unidirectional valve 68 (not shown), transferring needle 47, filling sleeve 66, piston spring 45, and venting aperture 46. FIG. 17A shows phase 1 of the filling process—vial 50 connection. The vial 50 is connected to the vial adaptor 41, the filling needle 43 and the venting needle 44 pierce the vial rubber seal (shown in FIGS. 10 and 11), and the tips of the filling needle 43 and the venting needle are in contact with the vial content (i.e. insulin).

FIG. 17B shows phase 2 of the filling process—interspace 48 filling, according to some embodiments. The vial 50 is pressed by the user in the direction of the bold arrow (downward) to the amount that corresponds to the desired amount of insulin to be filled in the reservoir (i.e. if the required amount is 150 U, the vial should be pressed until the 150 U mark is approached (FIG. 11)). The sliding rod 65 and filling piston 42 are displaced in the direction of the bold arrow and the piston spring 45 is compressed. Insulin is delivered from the vial 50 via the filling needle 43, the piston conduit 64 and the first unidirectional valve 61 into the interspace 48. Air follows the pressure gradient and is delivered through the venting needle 44 from the filling sleeve 66 (atmospheric pressure) to the vial 50 (sub-atmospheric pressure). At the end of the interspace filling phase, the interspace 48 is filled with the desire amount of insulin and the pressure within the vial 50 is atmospheric pressure. FIG. 17C shows phase 3 of the filling process, which also includes reservoir filling. Accordingly, the pressure from the vial 50 is removed and the filling piston 42, sliding rod 65, and vial adaptor 41 are displaced in the direction of the bold arrow (release of energy that was stored in the piston spring 45 during phase 1). The volume of interspace 48 is decreased and insulin is displaced from the interspace 48 into the reservoir (FIG. 15) via the second unidirectional valve 62 and the transferring needle 47.

FIG. 18 shows a magnified cross-section view of the reservoir filling mechanism 200 after the filling process is completed and the vial is disconnected, according to some embodiments. The reservoir filling mechanism 200 includes a plurality of, and preferably all of, the vial adaptor 41, needles protector 53, sliding rod 65, filling needle 43, venting needle 44, filling piston 42, interspace 48, piston conduit 64, transferring needle 47, piston gasket 49, interspace gasket 63, first unidirectional valve 61, second unidirectional valve 62, transferring needle 47, filling sleeve 66, piston spring 45, and venting aperture 46. Leaves of the petal-like shaped spring (needles protector 53) bend over the filling needle 43 and the venting needle 44 protecting the user from inadvertent self-pricking. The spring leaves of the needles protector 53 are preloaded in the straight position (parallel to the filling needle 43, venting needle 44 and vial adaptor 41) and resume their preset bent shape (spring unloaded) after vial displacement.

FIG. 19 shows a transverse cross-section view of the assistance device 4 including a few components of the reservoir filling mechanism 200, cannula insertion mechanism 300, and the DP 12. The reservoir filling mechanism 200 (dashed line) includes a plurality of, and preferably all of, the vial adaptor 41, needles protector 53, sliding rod 65, filling needle 43, venting needle 44, filling piston 42, interspace 48, piston conduit 64, transferring needle 47, piston gasket 49, interspace gasket 63, transferring needle 47, filling sleeve 66, piston spring 45, and venting aperture 46. The cannula insertion mechanism 300 (dashed line) includes a plurality of, and preferably all of, trigger 52 and inserter spring 69 (other parts are not shown). The DP 12 includes a plurality of, and preferably all of, the filling port septum 23, filling port well 24, reservoir 20, and reservoir plunger 21. The vial adaptor 41, the tip of the filling needle 43, and the tip of the venting needle 44 are preferably arranged below the trigger 52 proving free access to the trigger 52.

FIG. 20 shows a cross section of an assistance device 401 along the plane XX depicted in FIG. 4. Assistance device 401 includes cannula insertion mechanism 300 and reservoir filling mechanism 201. Reservoir filling mechanism 201, according to some embodiments, includes vial adaptor 541, plunger 548, venting needle 543, filling needle 544, filling needle cap 545, and cylinder 546.

Filling needle 544 and venting needle 543 may run through the body of plunger 548, with their ends protruding from the extremities of the plunger. The first end 550 of plunger 548 may be connected with vial adaptor 541. The first end of venting needle 543 and the first end of filling needle 544 may both protrude from the first end 550 of plunger 548 into the interior of vial adaptor 541. Various other features, according to various embodiments, may include the following functionality/structure/clarification:

The second end of plunger 548 may be configured to slidably or otherwise fit within cylinder 546. An airtight seal between plunger 548 and cylinder 546 may be established by means of a gasket 549. The closed end of the cylinder 546 may be configured with a septum 552.

The filling and the venting needles may be made from a metal, such as steel, or a plastic. The filling and the venting needles may be configured with sharp tips on both ends.

Vial adaptor 541 may be configured to reversibly receive vial 501. Whenever vial 501 is placed in vial adaptor 541 the septum of the vial adaptor is pierced by the first end of venting needle 543 and the first end of filling needle 544.

Venting needle 543 may be configured with a unidirectional valve 547 allowing air to flow from the interior of cylinder 546 to the interior of vial 501.

and/or

The second end of filling needle 544 may be provided with a filling needle cap 545. Filling needle cap 545 may be made from plastic. Filling needle cap 545 may be configured to seal the second tip of filling needle 544.

Figure 21:
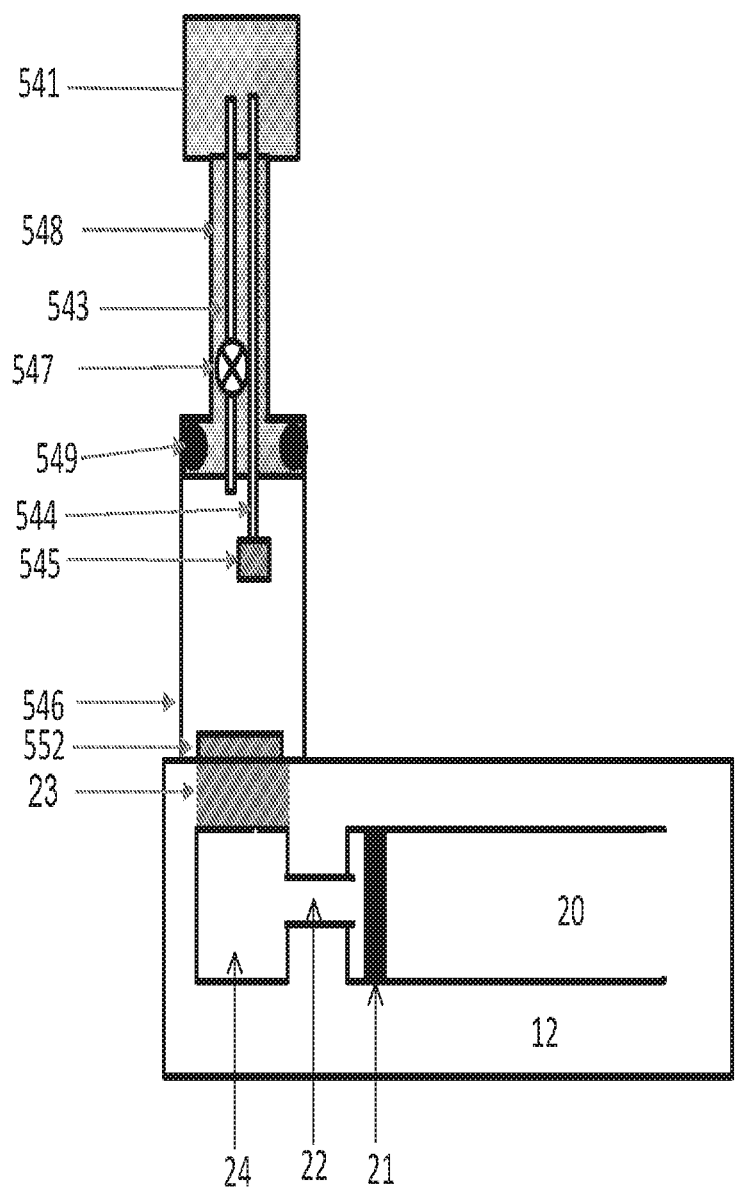
Figure 22:
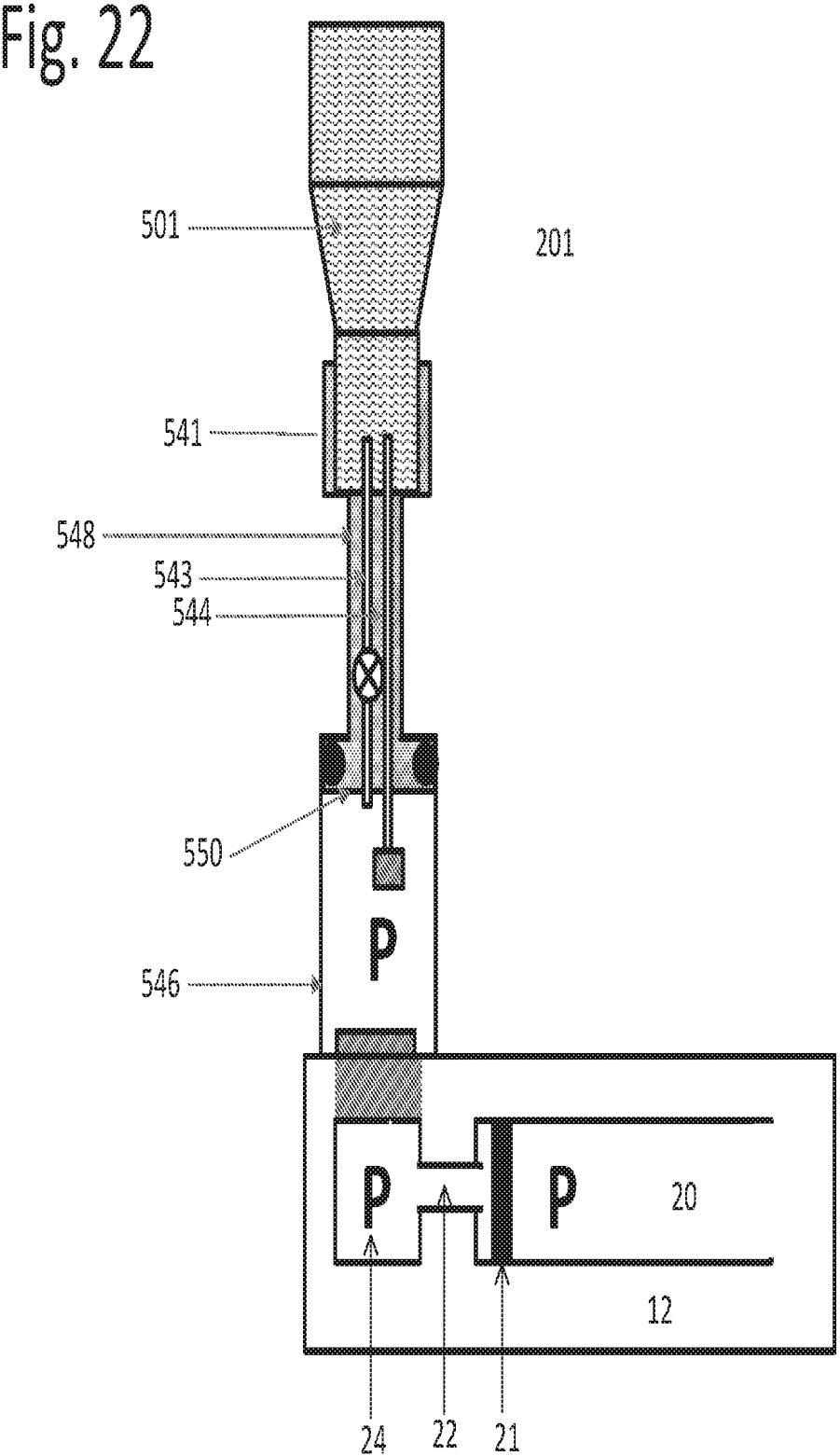
Figure 23:
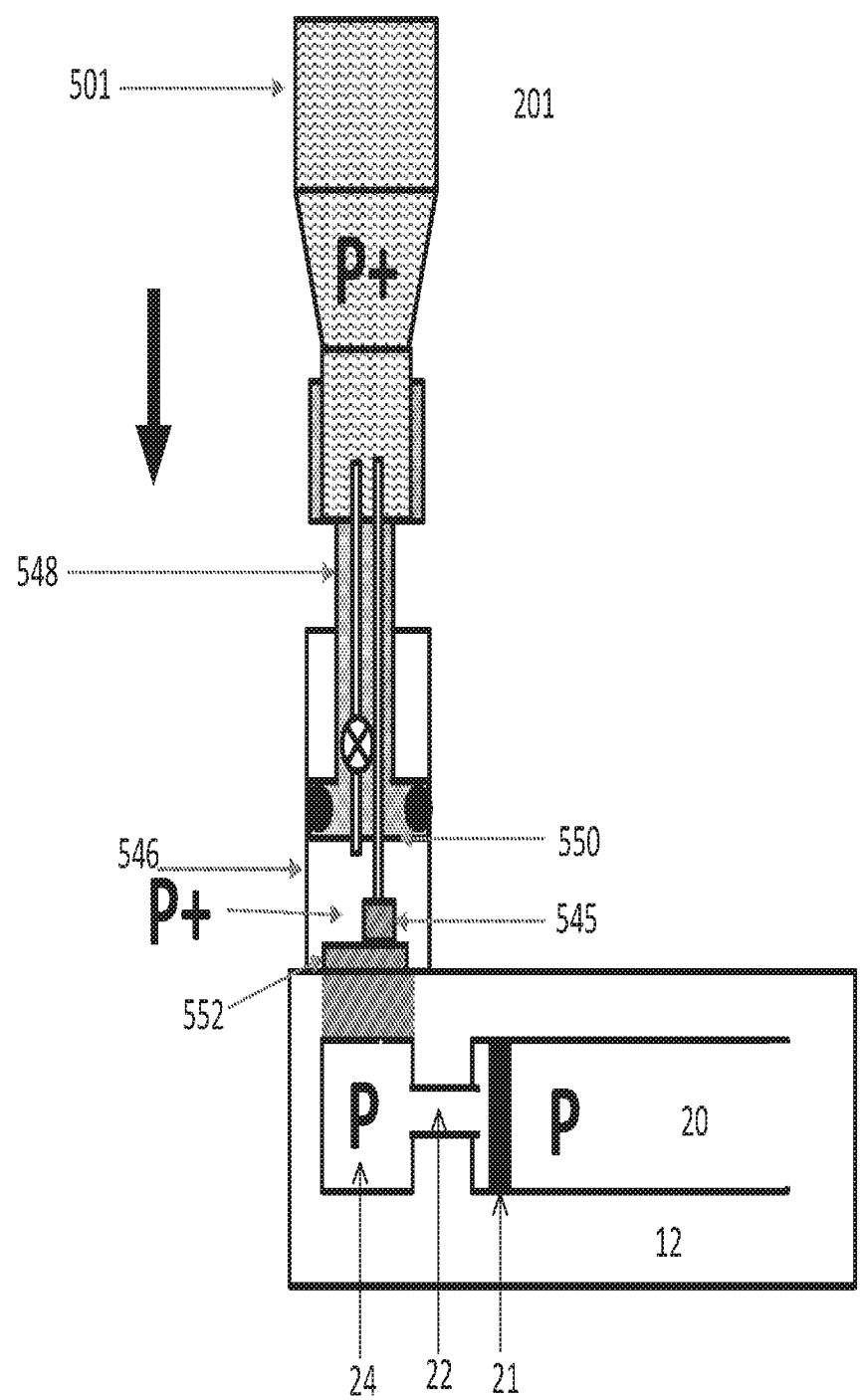
Figure 24:
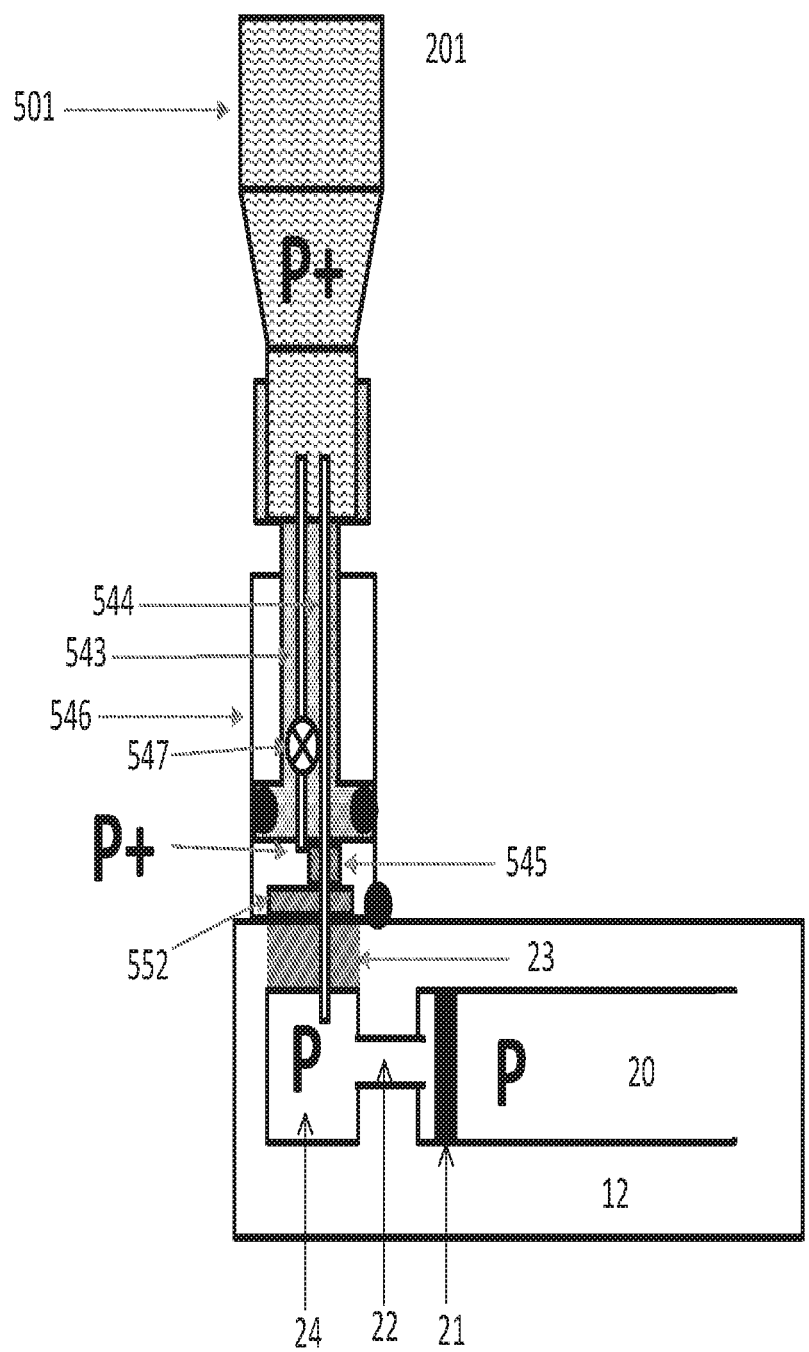

Reference is made to FIGS. 21-26, which show a cross section of reservoir filling mechanism 201, taken along the plane YY of FIG. 4, in action, according to some embodiments. Reservoir filling mechanism 201 can be configured within assistance device 401 such that septum 552 of cylinder 546 is adjacent to or in contact with filling port septum 23 (FIG. 21). The first step in filling reservoir 20 of pump disposable part 12 using reservoir filling mechanism 401, according to some embodiments, is placing vial 501 in vial adaptor 541 such that the first tip of venting needle 543 and the first tip of filling needle 544 pierce the septum of vial 501 (FIG. 22). Thus, following the placement of vial 501 in vial adaptor 541, air from the interior of cylinder 546 may flow through venting needle 543 into the interior of vial 501. Initially, the pressure within cylinder 543 may be the atmospheric pressure P. The pressures within the interior of filling port well 24, filling conduit 22, and the pressure exterior to reservoir plunger 21 may also be the atmospheric pressure P. The pressure in vial 501 may be greater than or equal to P. Vial 501 may initially include a volume of air (not shown) as well as insulin. End 550 of plunger 548 may initially be placed near the open end of cylinder 546.

In the second step (FIG. 23), the user pushes vial 501 downwards in the direction of the closed end of cylinder 546, thereby pushing end 550 of plunger 548 towards the closed end of cylinder 546. As a result, the volume of air trapped in the interior of cylinder 546 is reduced and the air within it is compressed. Air pressure within the interior of cylinder 546 increases to P+>P. Because the interior of cylinder 546 is in fluid communication with the interior of vial 501, the insulin in vial 501 becomes pressurized to P+ as well. Plunger 543 may advance in cylinder 546 to a position in which filling needle cap 545 comes into contact with cylinder septum 552.

Figure 25:
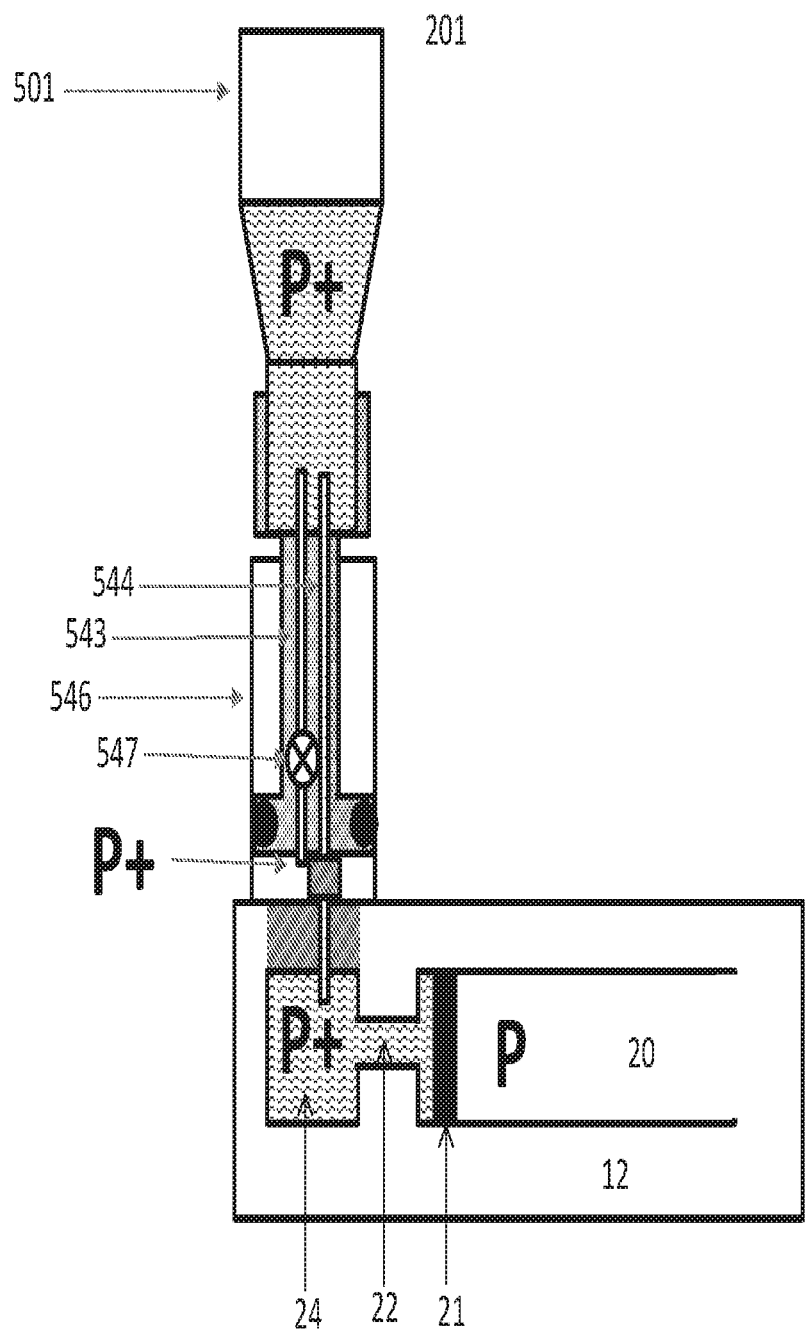
Figure 26:
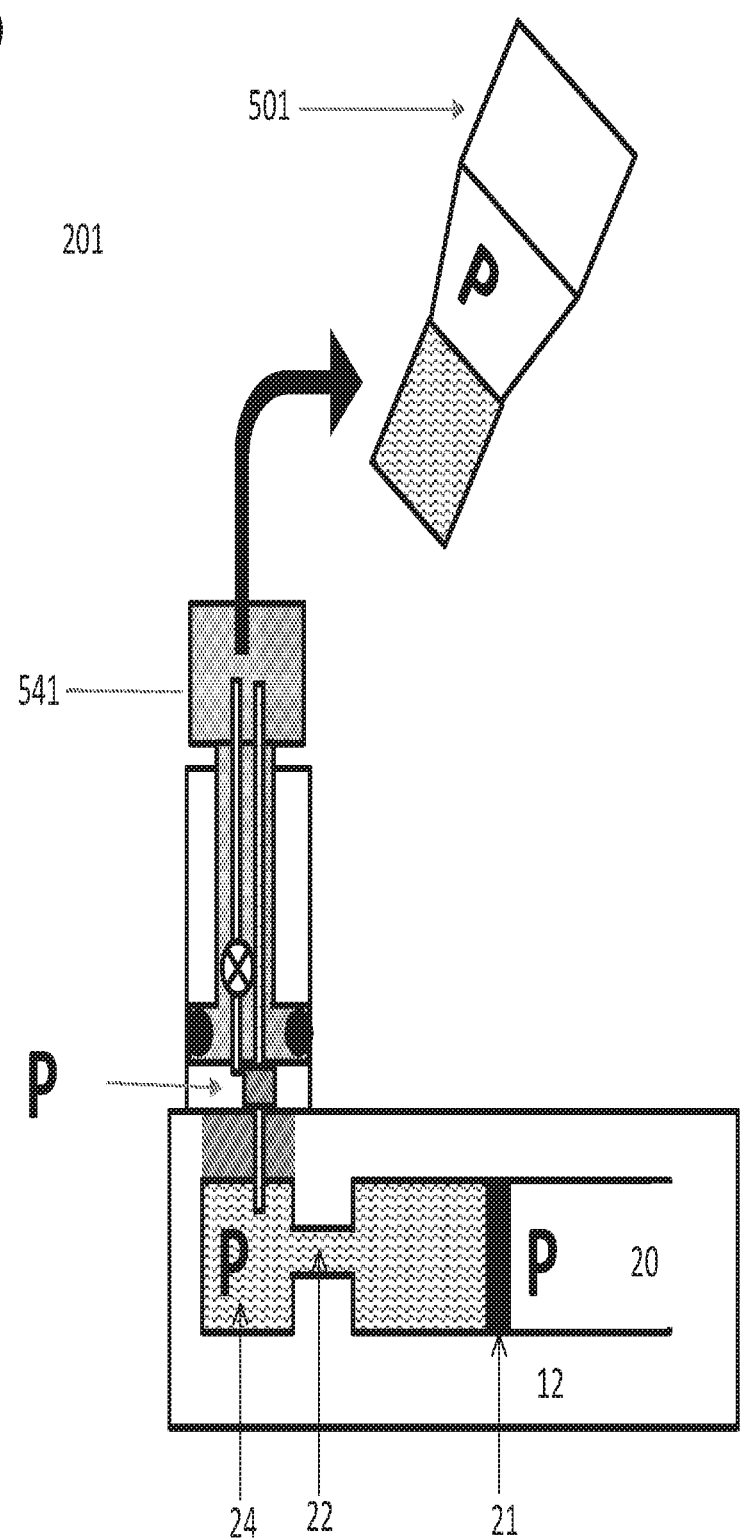

In the third step (FIG. 24), the user continues to push vial 501 in the direction of the closed end of cylinder 546. Filling needle 544 pierces through filling needle cap 545, cylinder septum 552 and filling port septum 23. As the second tip of filling needle 544 exits filling port septum 23 into filling well 24, fluid communication is established between the interior of vial 501 and filling well 24. Because the pressure P+ in vial 501 is greater than the atmospheric pressure P in filling well 24, insulin begins to flow from vial 501 into well 24 and air begins to flow from the interior of cylinder 546 through venting needle 543 into vial 501 (FIG. 25). Unidirectional valve 547 may prevent backflow of insulin or air from vial 501 to cylinder 546. Pressure P+ is established in filling well 24 and filling conduit 22. As a result, reservoir plunger 21 moves backwards and insulin enters reservoir 20 (FIG. 25). Insulin continues to fill the reservoir until the pressure in vial 501 and well 24 equals the atmospheric pressure (FIG. 26). The vial 501 is then removed from vial adaptor 541 and the filling process is complete.

FIG. 27 shows a cross section of an assistance device 402 along the plane XX depicted in FIG. 4. Assistance device 402 includes cannula insertion mechanism 300 and reservoir filling mechanism 202. Reservoir filling mechanism 202 includes vial adaptor 641, plunger 648, venting needle 643, filling needle 644, cylinder 646, and conduit 647 which may optionally be equipped with unidirectional valve 651. Filling needle 644 and venting needle 643 may protrude from the bottom end 650 of vial adaptor 641 and configured to puncture the septum of vial 601 and communicate with the interior of vial 601. Venting needle 643 may be in fluid communication with conduit 647, and conduit 647 may be in fluid communication with the interior of cylinder 646. Valve 651 may enable the flow of air through conduit 647 from the interior of cylinder 646 to venting needle 643, yet prevent the flow of air or insulin in the reverse direction. Filling needle 644 may initially be positioned across filling port septum 23, thereby enabling fluid communication between the interior of vial 601 and filling well 24. Plunger 648 may be configured to slidably fit within cylinder 646. An airtight seal between plunger 648 and cylinder 646 may be established by means of a gasket 649. Other functionality/features/clarifications may include:

The filling and the venting needles may be made from a metal, such as steel, or a plastic. The filling and the venting needles may be configured with sharp tips on both ends.

and/or

Vial adaptor 641 may be configured to reversibly receive vial 601. Whenever vial 601 is placed in vial adaptor 641 the septum of the vial adaptor is pierced by the first end of venting needle 643 and the first end of needle 644.

Figure 28:
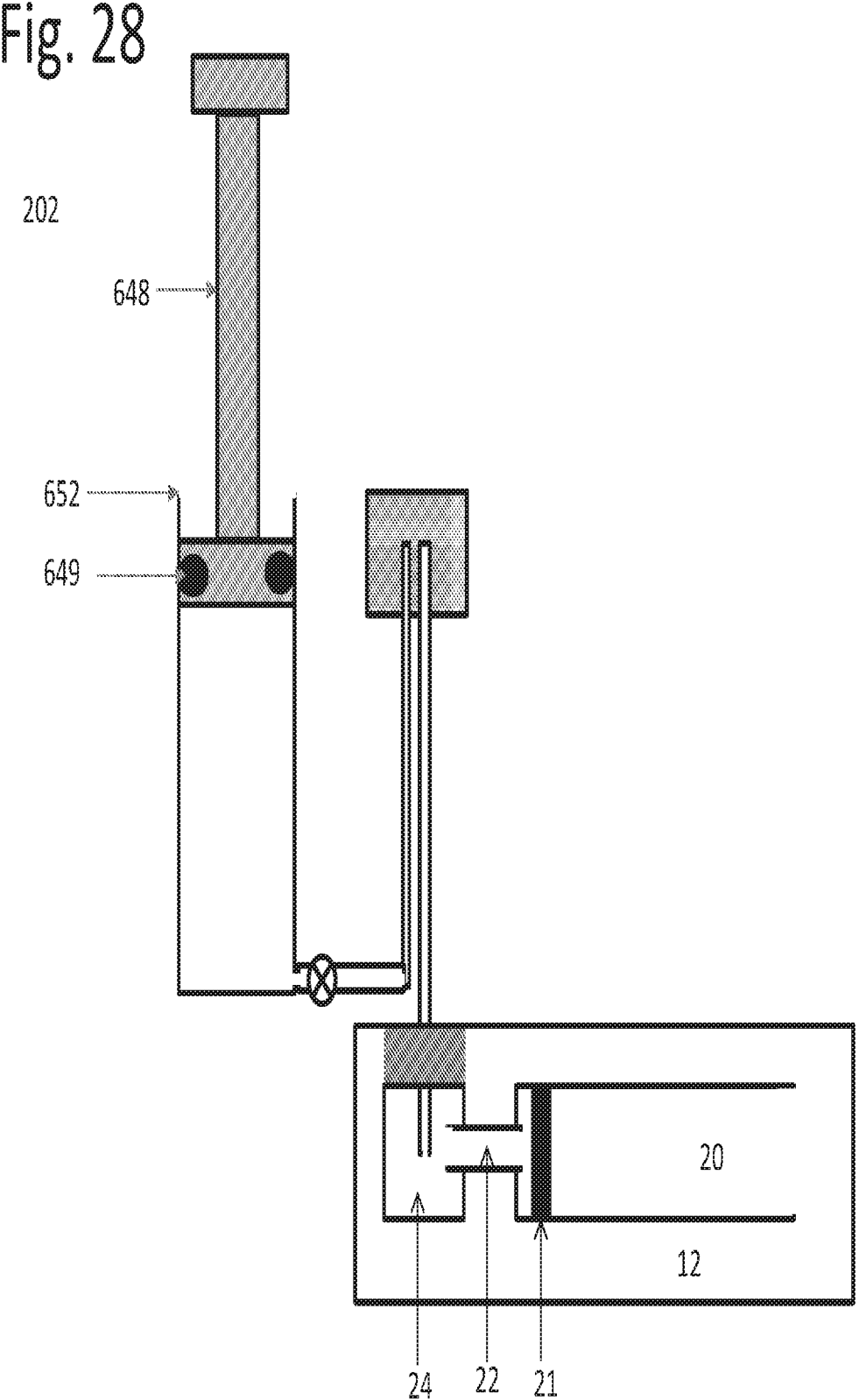
Figure 29:
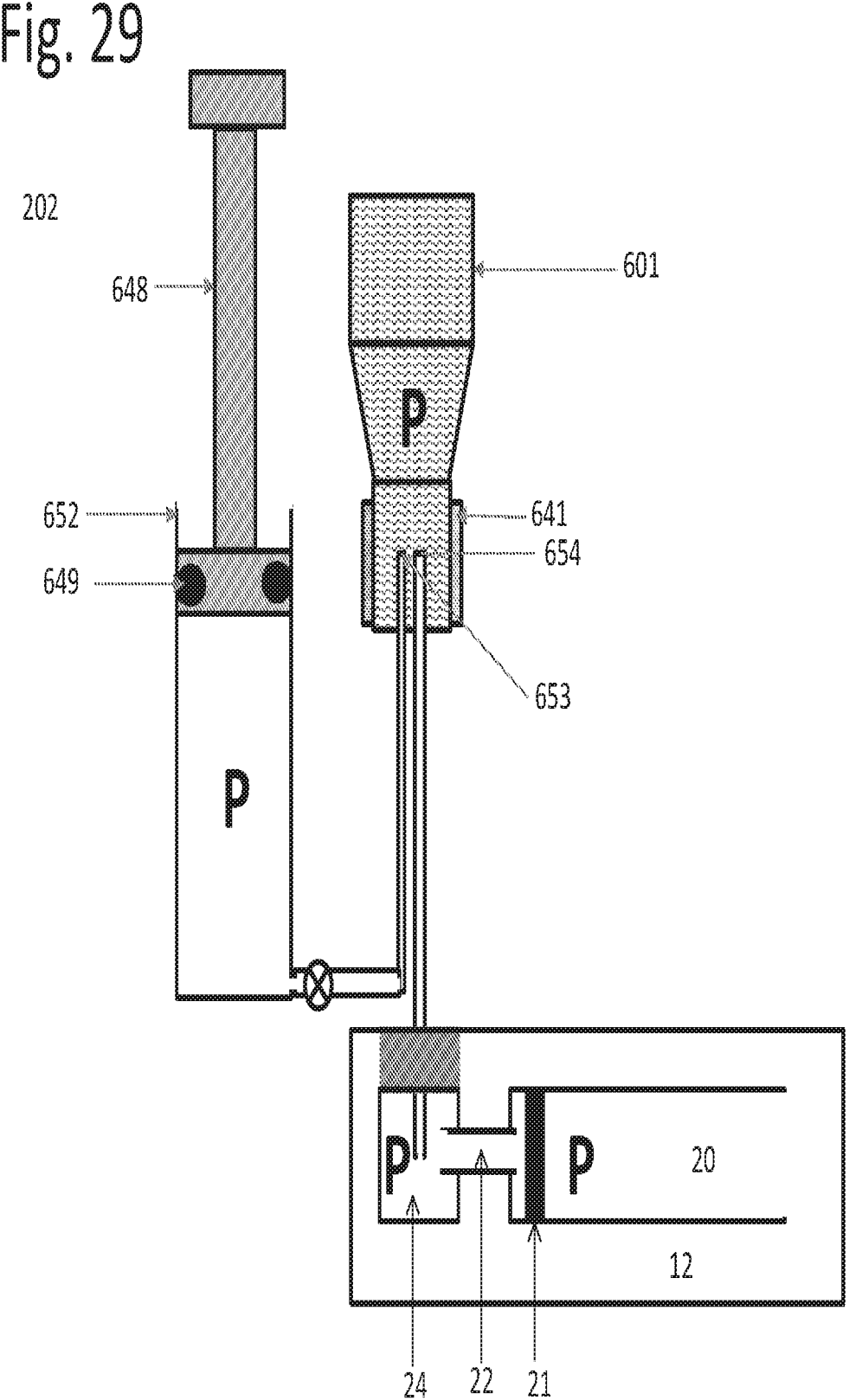
Figure 30:
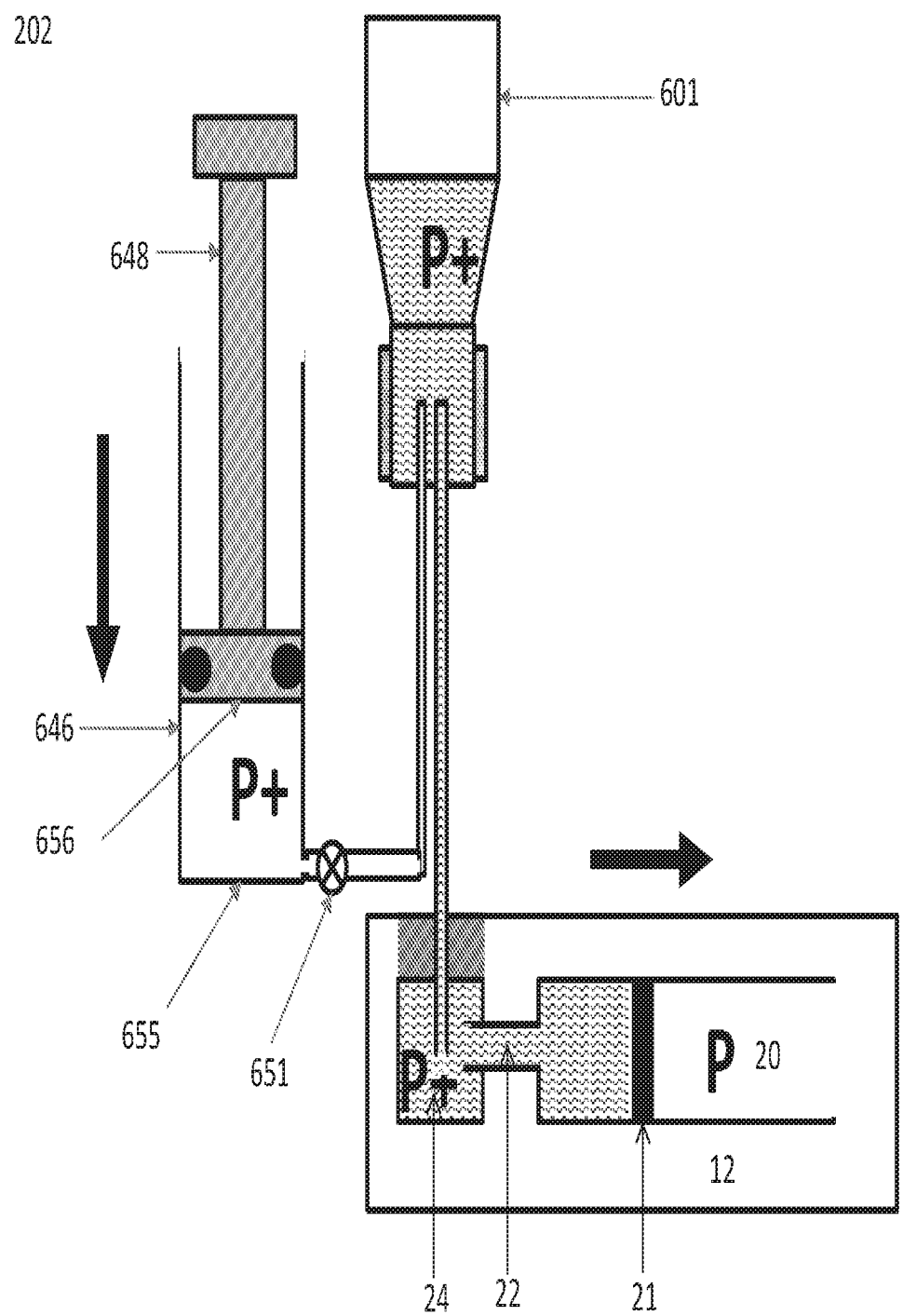
Figure 31:
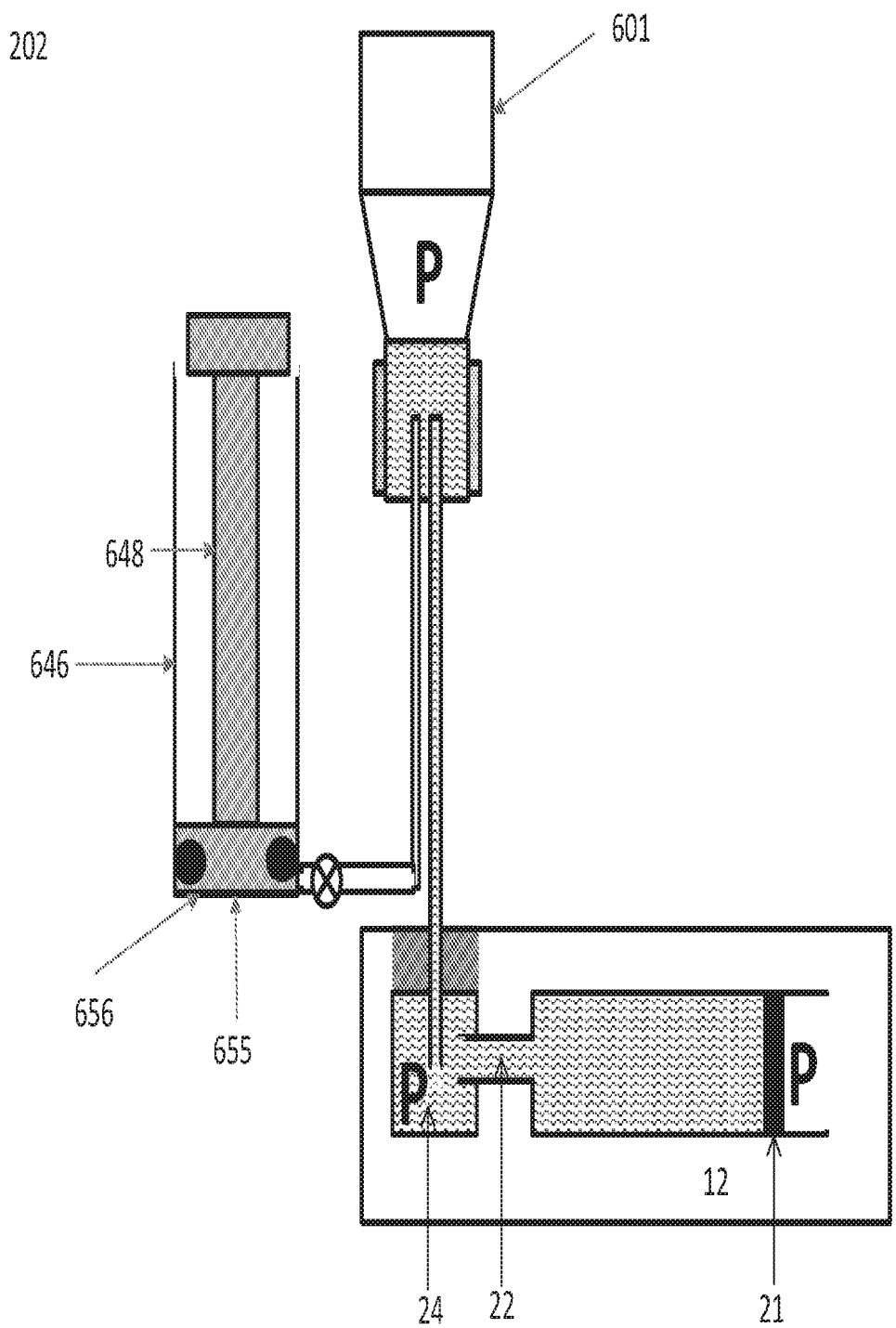
Figure 31:
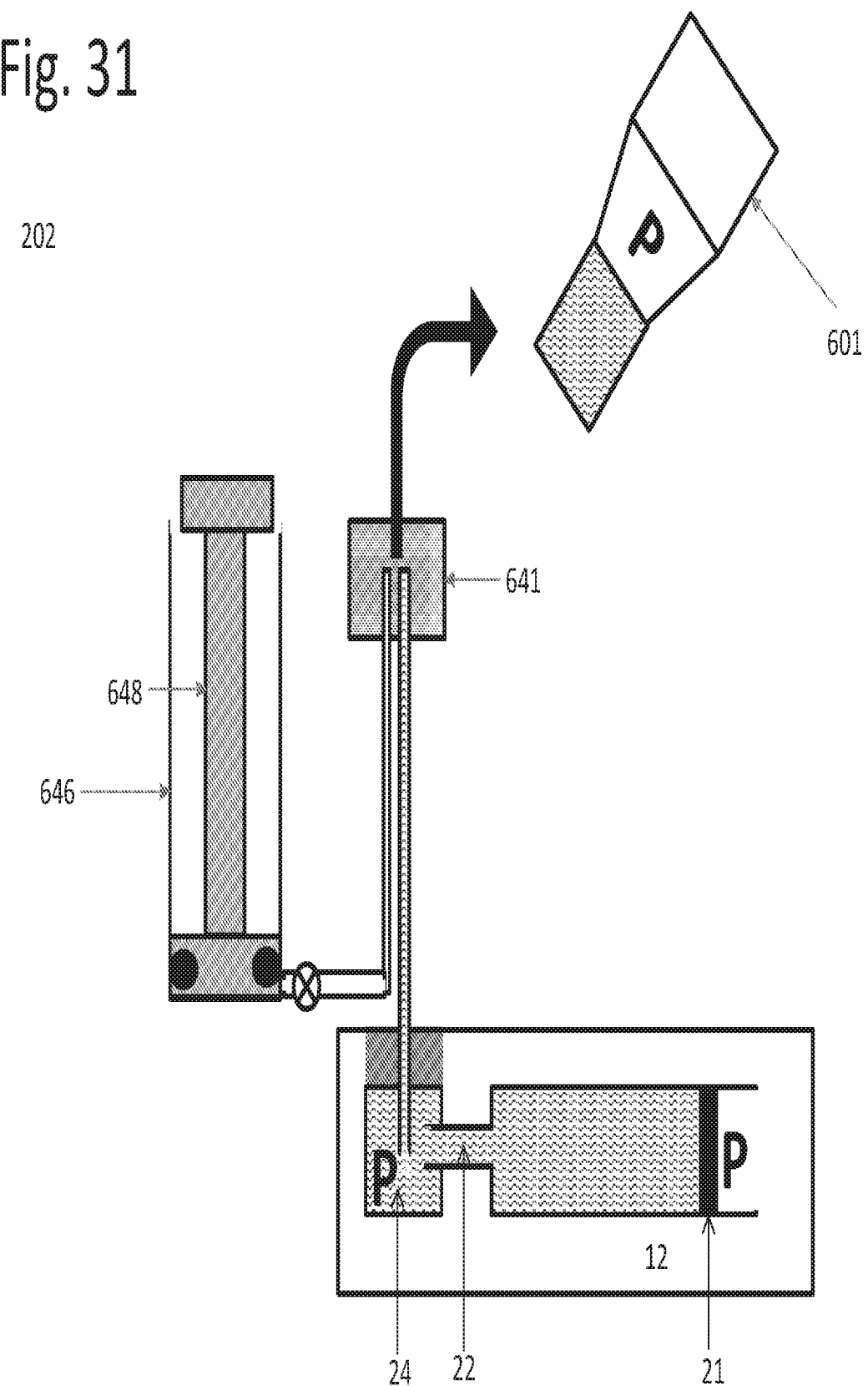

Reference is made to FIGS. 28-31, which show a cross section of reservoir filling mechanism 202, taken along the plane YY of FIG. 4, in action, according to some embodiments. Initially, plunger 648 is placed in cylinder 646 such that gasket 649 is near the opening 652 of the cylinder (FIG. 28). The first step in filling reservoir 20 of pump disposable part 12 using reservoir filling mechanism 202 is, according to some embodiments, placing vial 601 in vial adaptor 641 such that the tip 653 of venting needle 643 and the first tip 654 of filling needle 644 pierce the septum of vial 601 (FIG. 29). Thus, following the placement of vial 601 in vial adaptor 641, air from the interior of cylinder 646 may flow through venting needle 643 into the interior of vial 601. Initially, the pressure within cylinder 643 may be the atmospheric pressure P. The pressures within the interior of filling port well 24, filling conduit 22, and the pressure exterior to reservoir plunger 21 may also be the atmospheric pressure P. The pressure in vial 601 may be greater than or equal to P. Vial 601 may initially include a volume of air (not shown) as well as insulin.

In the second step (FIG. 30), the user pushes plunger 648 downwards in the direction of the closed end of cylinder 646. As a result, the volume of air trapped in the interior of cylinder 646 is reduced and the air within it is compressed. Air pressure within the interior of cylinder 646 increases to P+>P. Because the interior of cylinder 646 is in fluid communication with the interior of vial 601, the insulin in vial 601 becomes pressurized to P+ as well. Insulin flows from vial 601 to filling well 24 and filling conduit 22, which thus become pressurized to P+. As a result of the pressure differential across reservoir plunger 21, the reservoir plunger moves backwards in reservoir 20, which thereby fills with insulin. How of insulin from vial 601 towards cylinder 646 is prevented by optional unidirectional valve 651, which may be especially necessary if vial 601 is initially pressurized. The process continues until either the reservoir is completely filled with insulin (reservoir 20 may be equipped with stoppers preventing the exit of plunger 21 from the interior of the reservoir), until the end 656 of plunger 648 reaches the closed end 655 of cylinder 646 (FIG. 31), or until the pressure in vial 601 equalizes the atmospheric pressure P. A sensor measuring the level of insulin in reservoir 20 may provide the user with an indication once the desired level of insulin in the reservoir is reached. The vial 601 is then removed from vial adaptor 641 and the filling process is complete (FIG. 32).

FIG. 33 shows a cross section of an assistance device 403 along the plane XX depicted in FIG. 4. Assistance device 403 is similar to assistance device 402, except that it includes an automatic mechanism for depressing the plunger in the cylinder in lieu of manual depression as in device 402.

Device 403 includes cannula insertion mechanism 300 and reservoir filling mechanism 203. Reservoir filling mechanism 203 includes vial adaptor 741, plunger 748, venting needle 743, filling needle 744, cylinder 746, and conduit 747 which may optionally be equipped with unidirectional valve 751. Filling needle 744 and venting needle 743 may protrude from the bottom end 750 of vial adaptor 741 and be configured to puncture the septum of vial 701 and communicate with the interior of the vial. Venting needle 743 may be in fluid communication with conduit 747, and conduit 747 may be in fluid communication with the interior of cylinder 746. Valve 751 may enable the flow of air through conduit 747 from the interior of cylinder 746 to venting needle 743, yet prevent the flow of air or insulin in the reverse direction. Filling needle 744 may initially be positioned across filling port septum 23, thereby enabling fluid communication between the interior of vial 701 and filling well 24. Plunger 748 may be configured to slidably fit within cylinder 746. An airtight seal between plunger 748 and cylinder 746 may be established by means of a gasket 749.

The filling and the venting needles may be made from a metal, such as stainless, or a plastic. The filling and the venting needles may be configured with sharp tips on both ends.

Vial adaptor 741 may be configured to reversibly receive vial 701. Whenever vial 701 is placed in vial adaptor 741 the septum of the vial adaptor is pierced by the first end of venting needle 743 and the first end of needle 744.

Filling mechanism 203 may include a driving mechanism 770. The driving mechanism may comprise a power source 771, a controller 772, a motor 773, and a gear 774. The power source may be, for example, a single use battery or a rechargeable battery. The control unit may be a microcomputer, including a microprocessor and memory. The motor may be a direct current motor, such as a brush motor, a brushless motor, or a stepper motor. The power source may be the battery of the insulin pump residing in assistance device 403, and the controller may be the pump's controller. The gear may be coupled to the plunger by means, for example, of a lead screw or a rack. Driving mechanism 770 may also include an input device such as an operating button.

In operation, filling mechanism 203 works mechanically in similar fashion to filling mechanism 202. Therefore, a detailed description of the mechanics is omitted. However, in mechanism 203 the depression of plunger 748 in cylinder 746 is brought about by the action of driving mechanism 770. Upon connection of vial 701 to vial adaptor 741, the user may instruct driving mechanism 770 to depress plunger 748 in cylinder 746 through the input/output device. Alternatively, a sensor, such as an optical sensor, may detect the connection of the vial to the adaptor and then automatically instruct driving mechanism 770 to depress the plunger 748. The instruction from the user or the sensor may be delivered to controller 772, which may in turn provide voltage from power source 771 to motor 773. Motor 773 may in turn cause plunger 748 to depress in cylinder 746 by means of gear 774, thereby causing insulin to be delivered from vial 701 to filling well 24 and the pump reservoir as previously described for mechanism 202.

FIG. 34 shows a cross section of an assistance device 404 along the plane XX depicted in FIG. 4. Device 404 includes cannula insertion mechanism 300 and reservoir filling mechanism 204. FIG. 35 shows a cross section of filling mechanism 204 along the plane ZZ depicted in FIG. 4.

Reference is made to FIG. 34. In some embodiments, reservoir filling mechanism 204 includes vial adaptor 841, venting needle 843, filling needle 844, and conduit 847 which may optionally be equipped with unidirectional valve 851. Filling needle 844 and venting needle 843 may protrude from the bottom end 850 of vial adaptor 841, and be configured to puncture the septum of vial 801 and communicate with the interior of the vial. Venting needle 843 may be in fluid communication with conduit 847, and conduit 847 may be in fluid communication with the atmosphere. Optional valve 851 may enable the flow of air through conduit 847 from the atmosphere to venting needle 843, yet prevent the flow of air or insulin in the reverse direction. Filling needle 844 may initially be positioned across filling port septum 23, thereby enabling fluid communication between the interior of vial 801 and filling well 24.

Reference is made to FIG. 35. In some embodiments, reservoir filling mechanism 204 may further include a driving mechanism 870, and a coupling string. The driving mechanism may comprise a power source 871, a controller 872, a motor 873, and a reel 874. The power source may be, for example, a single use battery or a rechargeable battery. The control unit may be a microcomputer, including a microprocessor and memory. The motor may be a direct current motor, such as a brush motor, a brushless motor, or a stepper motor. The power source may be the battery of the insulin pump residing in assistance device 404, and the controller may be the pump's controller. Driving mechanism 770 may also include an input device such as an operating button. The coupling string 880 may have a first end 881 connected to reel 874, and a second end 882 connected to reservoir plunger 21. String 880 may be configured with a nick 883 near its distal end 882. Reservoir 20 may be configured with a stopper 884 disposed near its open end 885. String 880 may be configured to transmit pulling force exerted by driving mechanism 870 sufficient to retract reservoir plunger 882, yet break at nick 883 upon the reservoir plunger being pulled by the string against the stopper.

Figure 38:
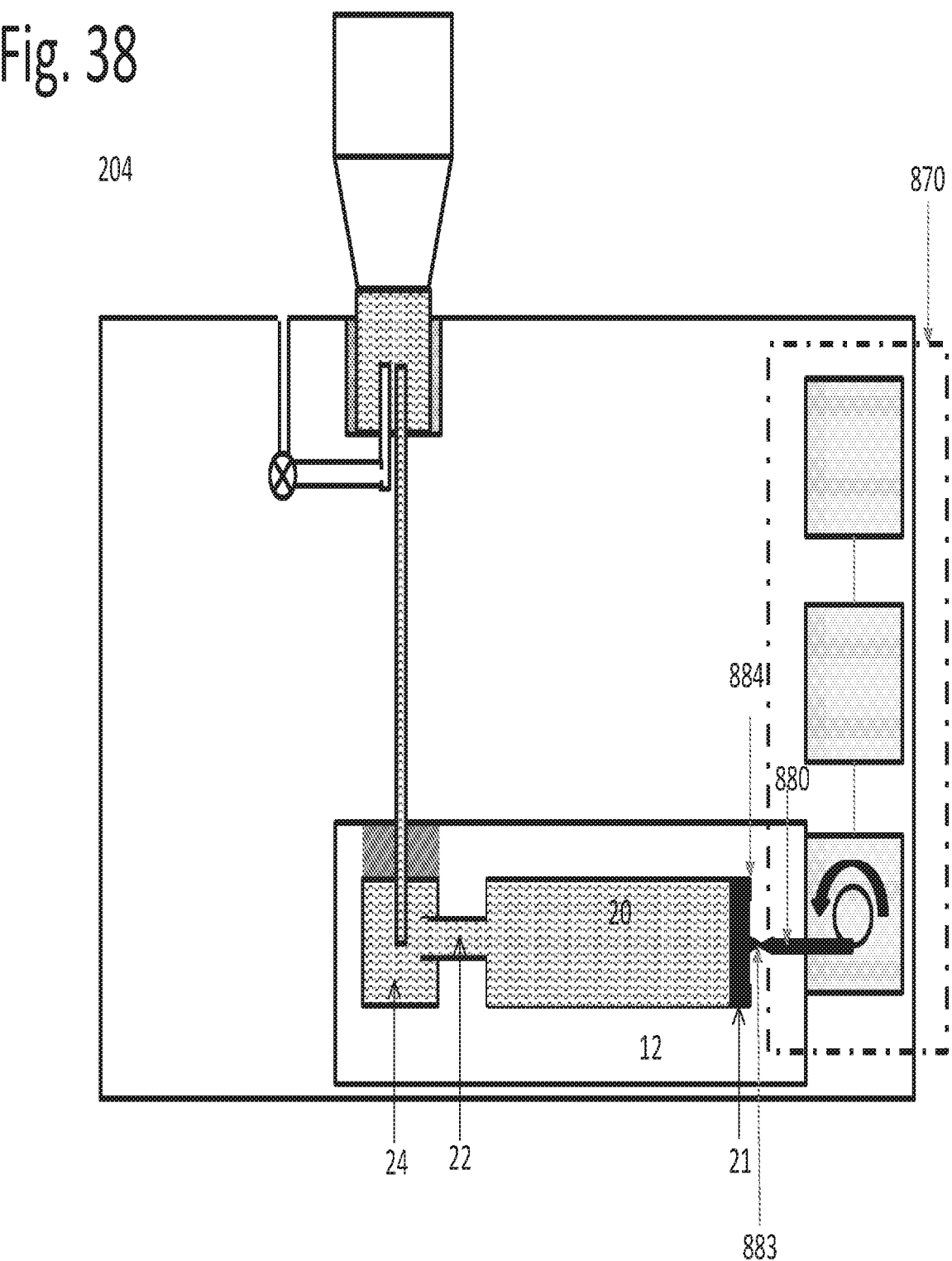
Figure 39:
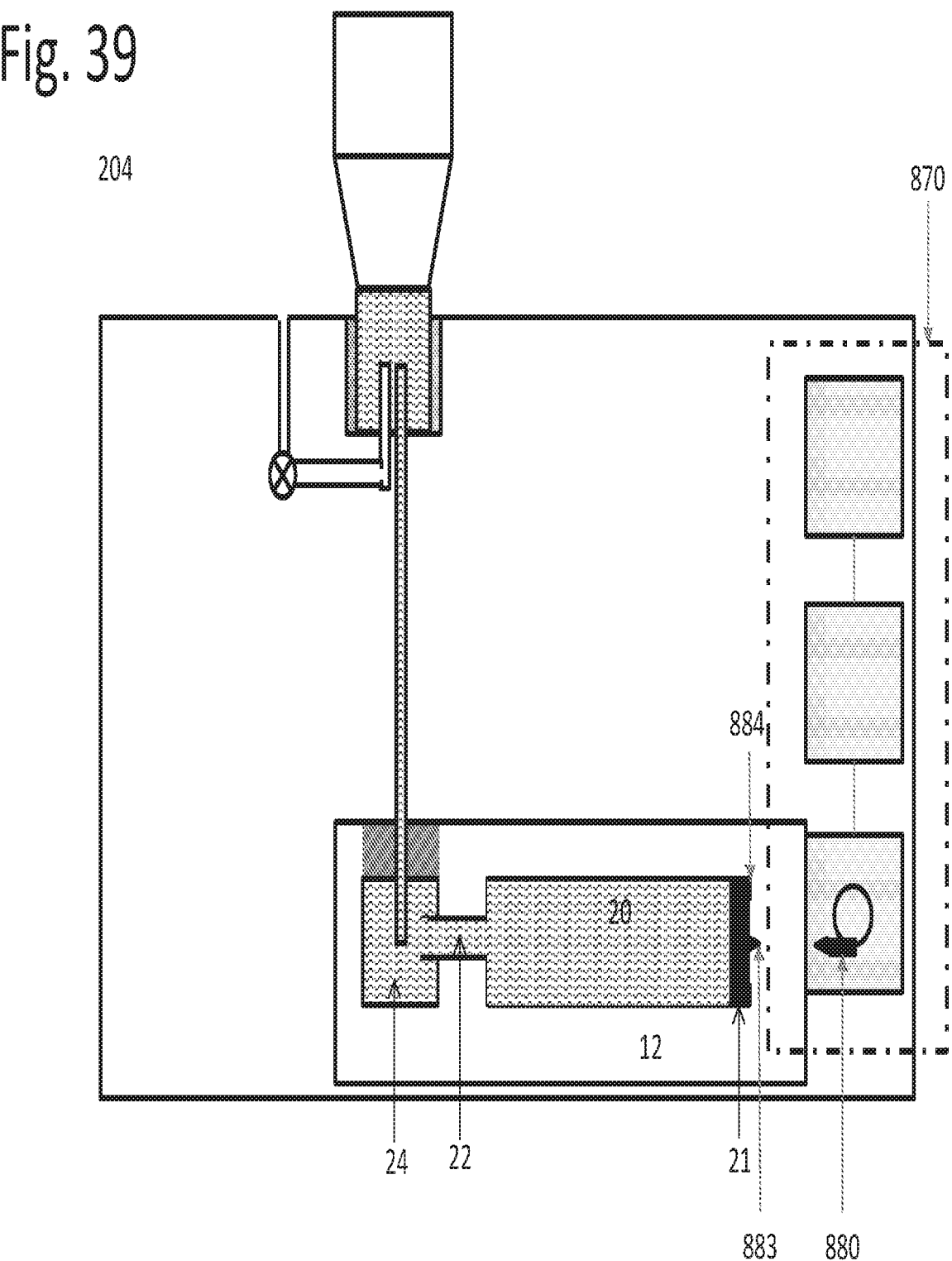
Figure 40:
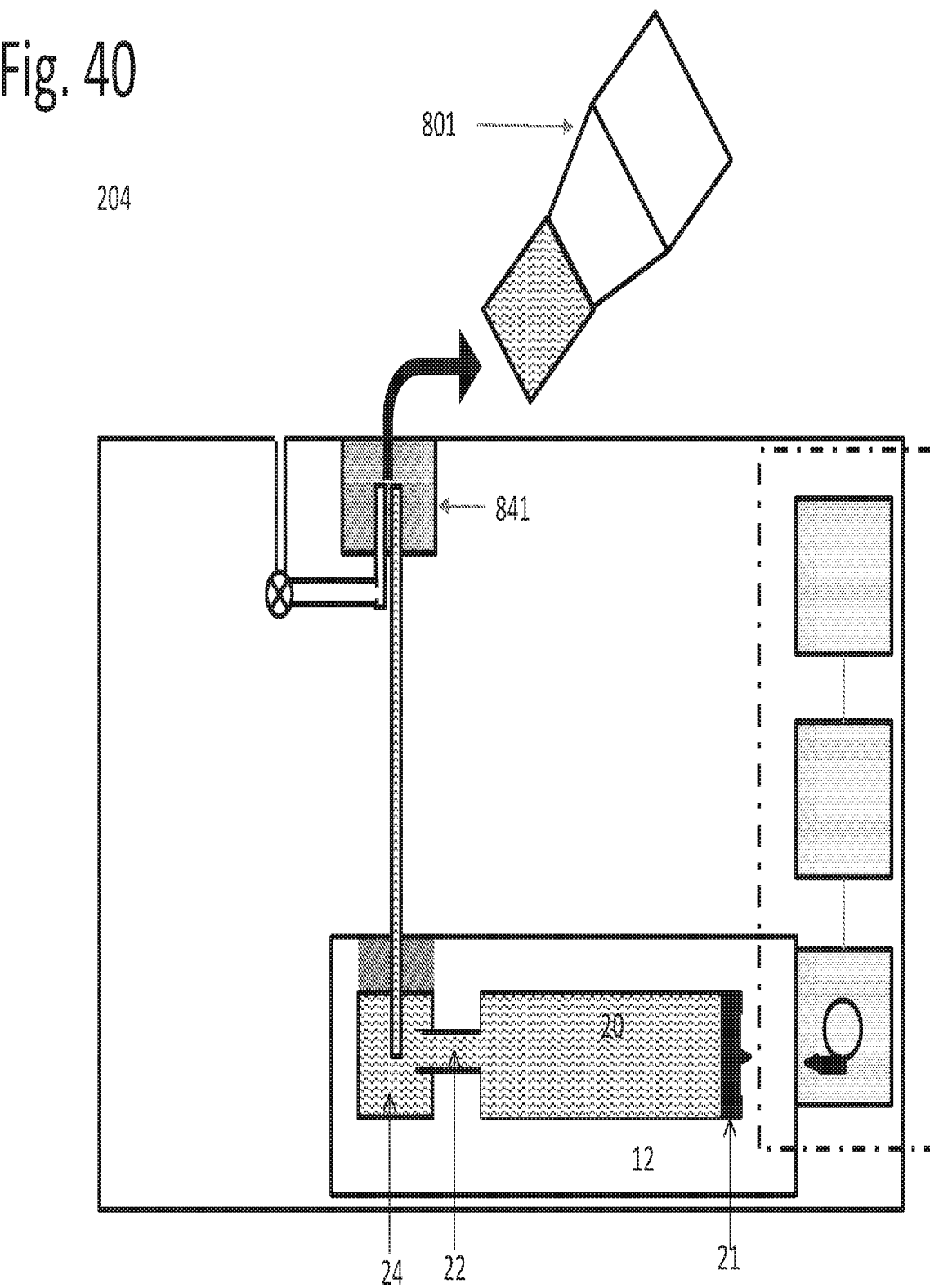

Reference is made to FIGS. 35-40, which depict a cross section of assistance device 404 taken along the ZZ plane of FIG. 4 in operation, according to some embodiments. In the first step of operation (FIG. 35), vial adaptor 841 is empty and reservoir plunger 21 is at the reservoir end proximate filling conduit 22. In the second step (FIG. 36), the user inserts vial 801 into vial adaptor 841. The first end of filling needle 843 pierces the septum of vial 801, thereby enabling fluid communication between the interior of the vial and the atmosphere. The first end of filling needle 844 also pierces the septum of vial 801. The second end of filling needle 844 traverses filling port septum 23, thereby enabling fluid communication between the interior of vial 801, filling port well 24 and filling port conduit 22. In the third step (FIG. 37), the user instructs the driving mechanism to fill the reservoir with insulin. The instruction may be given through the input device. Alternatively, a sensor in the vial adaptor, such as an optical or a mechanical sensor, may detect the presence of the vial 801 in the vial adaptor 841 and instruct the driving mechanism automatically to begin insulin filling. The instruction from the user or sensor may be delivered to controller 872, which may subsequently supply voltage from power source 871 to motor 873. The motor may cause reel 874 to rotate in the direction of the curved arrow (counter-clockwise) thereby pulling coupling string 880 in the direction of the straight arrow (right). The string may therefore cause reservoir plunger 21 to move towards stopper 884, thereby causing a negative pressure to form in the interior of vial 801. Insulin will thus flow from the vial to reservoir. Air from the atmosphere may flow into vial 801 through venting needle 843 and, optionally through valve 851, thereby replacing in the vial the insulin supplied to the reservoir. This process may continue until reservoir plunger 21 reaches stopper 884, which marks the end of reservoir filling (FIG. 38). Driving mechanism will continue to pull string 880 against stopper 884 until string 880 breaks at nick 883 (FIG. 39). At this point, driving mechanism 870 will cease to rotate reel 874, by, for example, means of an instruction from a motor current sensor, or by means of a motor revolution counter. Vial 801 may be removed (FIG. 40) from vial adaptor 841, which completes the filling process.

FIG. 41 shows a cross section of an assistance device 405 along the plane XX depicted in FIG. 4, according to some embodiments. Assistance device 405 includes cannula insertion mechanism 300 and reservoir filling mechanism 205. Reservoir filling mechanism 205 is similar to reservoir filling mechanism 201 of device 401, except that the cylinder 546 and the plunger 548 of mechanism 201 are replaced with a bellow 949 in filling mechanism 205.

Reservoir filling mechanism 205 includes vial adaptor 941, shaft 948, venting needle 943, filling needle 944, filling needle cap 945, and collapsible bellow 949. Filling needle 944 and venting needle 943 may run through the body of shaft 948, with their ends protruding from the extremities of the shaft. The first end 950 of shaft 948 may be connected with vial adaptor 941. The first of venting needle 943 and the first end of filling needle 944 may both protrude from the first end 950 of plunger 948 into the interior of vial adaptor 941.

The second end of shaft 948 may be connected to the first end 951 of bellow 949. The second end 954 of bellow 949 may be configured with a bellow septum 952. The connection of the bellow to the shaft may be airtight.

The filling and the venting needles may be made from a metal, such as steel, or a plastic. The filling and the venting needles may be configured with sharp tips on both ends.

Vial adaptor 941 may be configured to reversibly receive vial 901. Whenever vial 901 is placed in vial adaptor 941 the septum of the vial adaptor can be pierced by the first end of venting needle 943 and the first end of needle 944.

Venting needle 943 may optionally be configured with a unidirectional valve 947 allowing air to flow from the interior of cylinder 943 to the interior of vial 901, yet preventing air or fluid flow from the interior of the vial to the interior of the bellow.

The second end of filling needle 943 may be provided with a filling needle cap 945. Filling needle cap 945 may be made from plastic. Filling needle cap 945 may be configured to seal the second tip of filling needle 945.

The operation of filling mechanism 205 is similar to that of filling mechanism 201. Therefore, its detailed description is omitted. Briefly, the first step is to connect vial 901 to vial adaptor 941. Fluid communication is established between the interior of bellow 949 and the interior of vial 901. Next, the user pushes the vial down, thereby compressing the air trapped in the bellow. The increased pressure is transmitted to the interior of the vial. This continues until filling needle cap 945 touches bellow septum 952. The user then continues to push the bottle down, thereby causing filling needle 944 to pierce the cap, the bellow septum and the filling port septum 23. Fluid communication is established between the interior of the vial and filling port well 24. The increased pressure in the vial causes insulin to flow from the vial to the filling port well. The increased pressure in the filling port causes the reservoir plunger to retract, thereby filling the reservoir with insulin. Once the reservoir is filled, the vial is disconnected from the vial adaptor and the filling process is complete.

Reference is made to FIG. 42, which shows various schematic drawings of an insulin pump 302 according to some embodiments. FIG. 42A shows a schematic top view of pump 302. FIG. 42B shows a schematic cross section taken along the plane YY. FIG. 42C shows a schematic cross section taken along the plane ZZ, and FIG. 42D shows a schematic cross section taken along the plane XX.

Figure 42A:
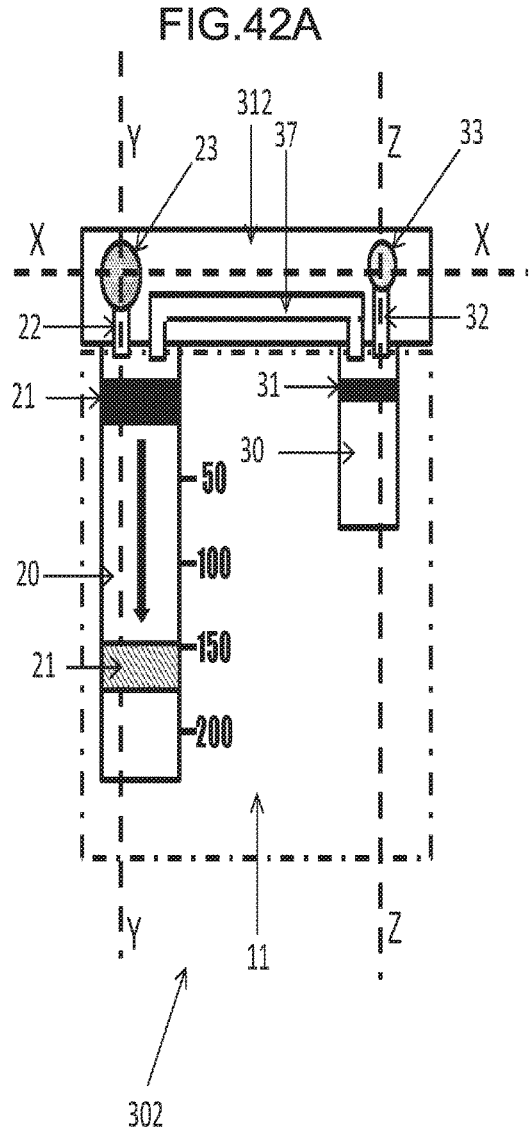
Figure 42B:
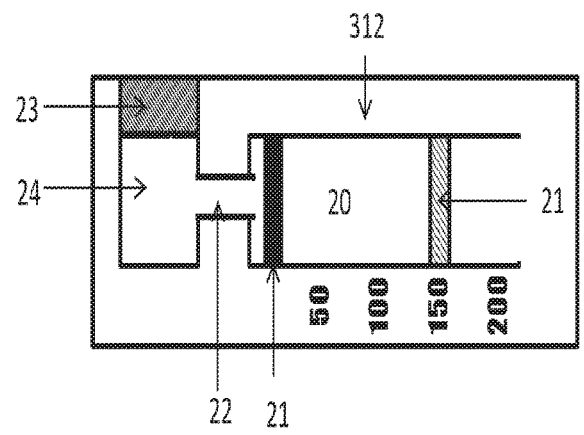
Figure 42C:
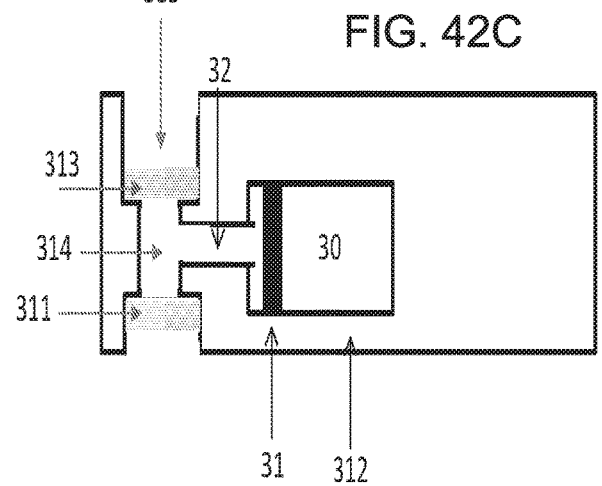
Figure 42D:
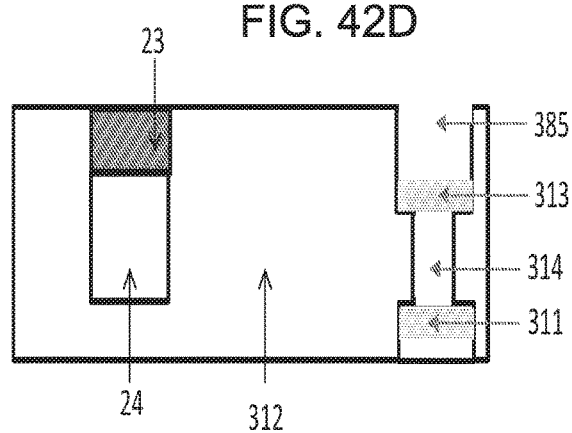

Pump 302 is very similar to pump 1 described above, except that disposable part 12 is replaced with disposable part 312. Disposable part 312 is very similar to disposable part 12, except that (1) exit port septum 33 is replaced with top exit port septum 313 configured within a cup hole 385, which is integral with disposable part 312, (2) exit port well 34 is replaced with exit port well 314 and (3) bottom exit port septum 311 is added (FIGS. 42C and D).

Reference is made to FIG. 43, which shows a schematic drawing of an assistance device 406 including pump 302 assembled therein, according to some embodiments. Assistance device 406 includes the reservoir filling mechanism 200 described above, as well as a soft cannula insertion mechanism 301. Soft cannula insertion mechanism 301 includes trigger 352, inserter spring 369, inserter hammer 354, steel cannula 336 (which may also be referred to as a rigid cannula), soft cannula 377, cup 381, and cup septum 382. Cup 381 is configured to ultimately fit snugly (i.e., securely) within cup hole 385.

Steel cannula 336 may be made from metal, such as steel or, for example, from a hard plastic. Soft cannula 377 may be made from a soft plastic, such as, for example, Teflon. Steel cannula 336 may be configured with a steel cannula side hole 337 and soft cannula 377 may be configured with a soft cannula side hole 378. Initially, steel cannula 336 may be arranged in the lumen of soft cannula 377 such that side holes 337 and 378 coincide.

The top end of steel cannula 336 may be rigidly connected to inserter hammer 354. The top end of soft cannula 377 may include a stopper 379, configured to prevent soft cannula 377 from sliding out of the bottom end of cup 381. The stopper may be integral with the cannula. Cup septum 382 may seal the interior of cup 381. Steel needle 336 may initially traverse cup septum 382. Initially, the sharp bottom end of steel cannula 336 may protrude beyond the bottom end of soft cannula 377. Both ends may initially reside in exit port well 314. Initially, both steel cannula 336 and soft cannula 377 may traverse top exit port septum 313. Initially, inserter spring 369 may be cocked, that is, placed in a condition under which the inserter spring includes potential energy. Cannula bending spring 371 may also be cocked (i.e., placed in a condition under which the bending spring includes potential energy), prevented from bending towards the cannulas by the side of pump 302.

Reference is made to FIGS. 43-45. According to some embodiments, in operation, assistance device 406 may be used as previously described to assemble pump 302 from the reusable and disposable parts. Reservoir filling mechanism 200 may be used to fill the reservoir with insulin. Once the reservoir is full, doser 30 may be operated to prime the pump by pumping fluid through exit port conduit 32 into filling port well 314, and from there through the lumen of steel cannula 336 and out of side holes 337 and 378 (FIG. 43). The priming process may continue until air exits the doser and reservoir and insulin drips out of side hole/opening 378. Note that the top end of steel cannula 336 may be sealed and that the top end of soft cannula 377 may create a seal with steel cannula 336, and therefore the only way for insulin to flow out of exit port well 314 during priming is through the side holes 337 and 378.

Once priming is complete, the user may peel the liner from the adhesive base (not shown) and reversibly place pump 302 on the body using assistance device 406. The user may then use soft cannula insertion mechanism 301 to place the bottom tip of soft cannula 377 under the skin. This may be done in the following way (FIG. 43): First, the user may press trigger 352 and the safety catches (no shown) to release the energy stored in cocked inserter spring 369 and drive inserter hammer 354 in the bottom direction. Thus, cup 381, cup septum 382, steel cannula 336 and soft cannula 377 may move towards the patient's skin. The sharp tip of steel cannula 336 may puncture the skin and subcutaneous tissue, making a path to follow for soft cannula 377. The insertion process may end (FIG. 44) when the bottom of cup 381 resides on the top of top septum 313, with cup 81 placed in cup hole 385, and side holes 337 and 378 are in fluid communication with exit port well 314. The bottom ends of steel cannula 336 and soft cannula 377 are under the patient's skin.

Next, the user may remove assistance device 301 (FIG. 45), thereby also removing steel cannula 336 from the lumen of soft cannula 377. The elastic energy stored in cannula bending spring 371 may be released upon separation of the assistance device and the pump. The spring may bend in the direction of steel cannula 336, thereby bending the steel cannula into the interior of the assistance device. Sharp injury by the steel cannula is thus prevented. Pump 302 remains adhered to the patient's body, with soft cannula 377 inserted transcutaneously with its bottom end under the patient's skin, and with side hole 378 in fluid communication with exit port well 314. The user and doser 30 are in fluid communication via exit port conduit 32 (FIG. 42C), exit port well 314, soft cannula side hole 378 and the patient's subcutaneous tissue. As cup septum 382 is sealed once steel cannula 336 is removed, the only place insulin can flow from doser 30 is to the user. The pump is ready to deliver insulin to the user.

Note that any combination of a reservoir filling mechanism 200, 201, 202, 303, 204, or 205 may be used in combination with either cannula insertion mechanism 300 or soft cannula insertion mechanism 301 to produce an assistance device.

Reference is made to FIG. 46, which shows a closed loop insulin delivery system, (or artificial pancreas) 1000, according to some embodiments. Closed loop system 1000 can include a pump 1001, a controller 1002, a charger 3, and an assistance device 1004. Pump 1001 includes a reusable motor unit 1011 and a disposable cannula unit 1012 that are reversibly attachable.

Motor unit 1011, according to some embodiments, is substantially similar to motor unit 11 described previously. Accordingly, it may include an electronics module, a driving mechanism and a battery (all not shown). The electronics module may comprise a microprocessor, memory, and communications, such as low energy blue tooth radio (BLE). The memory may include software comprising a closed loop algorithm that calculates the instantaneous insulin infusion rate as a function of inputs including, for example, past and present glucose levels sensed by a continuous glucose sensor. Motor unit 1011 (FIG. 47) may include electrical contacts 1020 electrically connected to the electronics module. Electrical contacts 1020 may include one or more contacts. Electrical contacts 1020 may include four contacts, with two contacts 1021 configured to supply power from the motor unit and two contacts 1022 configured to transmit data. Data may be transmitted in analog or digital form.

Cannula unit 1012 (FIG. 48), according to some embodiments, is substantially similar to cannula unit 12 described previously. Cannula unit 1012 may include a reservoir 20, a doser 30, and an adhesive base 40, similar to the corresponding parts of cannula unit 12. The main difference is that cannula unit 1012 may include a channel 1013 traversing it from top to bottom. Channel 1013 is configured to receive a continuous glucose sensor and to assist in establishing electrical contact between contacts 1020 on motor unit 1011 and the continuous glucose sensor.

Controller 1002, according to some embodiments, is substantially similar to controller 2 of system 1, except that it may include in addition software to support the closed loop algorithm of system 1000. The charger of system 1000 is similar to the charger 3 of system 1.

Assistance device 1004, according to some embodiments, is similar to assistance device 4, except that it includes a modified inserter module capable of storing a continuous glucose sensor and inserting it under the patient's skin.

Reference is made to FIG. 49. FIG. 49A shows a schematic top view of pump 1001 when deployed in a user, according to some embodiments. The plane where motor unit 1011 interfaces with cannula unit 1012 is denoted WW, and the plane parallel to WW and intersecting filling port septum 23 and exit port septum 33 is denoted XX as before. A continuous glucose sensor 1050 is placed in channel 1013. FIG. 49B shows a cross section of Pump 1001 along plane WW, with continuous glucose sensor 1050 placed in channel 1013, with the pointed end of sensor 1050 protruding beyond the skin-facing plane of the pump 1001. FIG. 49C shows a cross section a cross section of pump 1001 along plane XX, with the sharp end of cannula 36 protruding from the skin-facing plane of pump 1001.

Reference is made to FIG. 50 which shows a front view of continuous glucose sensor 1050 according to some embodiments. Sensor 1050 comprises a head 1051 a prong 1052, both of which may include a basis made from an insulator such as a biocompatible plastic or a ceramic. Electrical contacts 1060 may be placed on the head by, for example, printing. Electrical contacts 1060 may include one or more contacts configured to interface with contacts 1020 on motor unit 1011. Electrical contacts 1060 may include four contacts, including a pair of contacts for transmitting power from the motor unit, and a pair of contacts 1062 for transmitting analog or digital data. Sensor 1050 may include a front-end chip 1070, possibly including an analog-to-digital converter, working electrode 1080, and a counter-electrode 1090 on its back side (FIG. 51). Sensor 1050 may optionally include a reference electrode (not shown). Whenever a reference electrode is used, additional contacts 1020 and 1060 may include five or more contacts.

Working electrode 1080 (FIG. 51) may include a conductor 1081 made from a metal such as platinum, an enzyme 1082, such as glucose oxidase, configured to generate an electrical current proportional to the ambient glucose concentration, and a selective membrane 1082, such as PTFE, configured to prevent interference from non-glucose electrochemically active agents. The various layers of the working electrode may be printed. Counter electrode 1090 may be made, for example, from silver or silver chloride. Working electrode 1080 may be electrically connected to front end chip 1070 by a conductor 1066. Counter-electrode 1090 may be connected to front-end chip 1070 by a conductor 1067, configured to traverse prong 1052 from the front to the back through a hole in the prong.

Working electrode 1080 may comprise a metal catalyst in lieu of the enzyme. Selective membrane 1082 may be optional.

Electrical contacts 1060 may be covered by a tape 1063, which may be adhesive on both sides. Tape 1063 may have high electrical conductivity in the Z directions and very low electrical conductivity in the X and Y directions. For example, tape 1063 may be a Z-Axis Conductive Tape made by 3M. Optionally, tape 1063 may be surrounded by a ring or frame of double sided adhesive, which may create a water proof seal around contacts 1020 and 1060 when pressed between the two plane surfaces sandwiching them (not shown). Contacts 1061 may be electrically connected to front-end chip 1070 by power-supplying conductors 1064, and data may be transmitted to and from chip 1070 by data conductors 1065.

The head of sensor 1050 may be covered by a liner 1100 (FIG. 51), according to some embodiments. Liner 1100 may be made out of, for example, a thin layer of plastic, a thin layer of paper, or paper coated by a plastic layer. Liner 1100 may include a motor unit facing part (MU facing part) 1101 and a cannula-unit facing part (CU facing part) 1102. The CU facing part 1102 may be folded over itself and connected to the back side of head 1051 using an adhesive layer. The MU facing part 1101 may also be folded over itself and connected to the front of the head using tape 1063. Proximal end 1103 may be connected to hammer 1054 of assistance device 1004's insertion mechanism 1300 (FIG. 52).

Reference is made to FIGS. 52 and 53, which schematically show an assistance device 1004 according to some embodiments. Assistance device 1004, according to some embodiments, is similar to, for example, assistance device 4. It includes a filling mechanism 200, and an insertion mechanism 1300 configured to insert subcutaneously both cannula 36 and continuous glucose sensor 1050. FIG. 52 shows a schematic cross section of assistance device 1004 taken along the XX plane depicted in FIG. 49A, and FIG. 53 shows a schematic cross section of assistance device 1004 taken along the WW plane depicted in FIG. 49A. The main differences between assistance device 1004 and assistance device 4 are that device 1004 initially includes pump 1001 instead of pump 1, insertion mechanism 1300 includes sensor 1050, and inserter hammer 54 is replaced with inserter hammer 1054. Inserter hammer 1054 is configured to simultaneously deploy both cannula 36 and sensor 1050 through the pump (the latter via channel 1013) and traverse the user's skin. Alternatively, two separate hammers may be used in insertion mechanism 1300 to insert the cannula and the sensor.

The operation of system 1000, according to some embodiments, is similar to the operation of system 1 described above. Motor unit 1011 may be inserted into a slot in assistance device 1004, thereby assembling pump 1001 from motor unit 1011 and cannula unit 1012. Pump 1001 may be filled with insulin using insulin filling mechanism 200 as described above. The pump may then be primed using a command from controller 1002. The adhesive on the skin-facing side of pump 1001 may be exposed by peeling a liner (not shown). Assistance device 1004 may then be used to place pump 1001 on the user's skin at a desired location. Once the pump is adhered to the skin, trigger 52 may be pressed to shoot the cannula and the sensor by means of releasing the elastic energy stored in spring 69. The force generated by the spring may be transmitted to the cannula 36 and the sensor 1050 by hammer 1054.

The sharp tip of prong 1052 may penetrate the user's skin. Alternatively, a guiding needle (not shown) may be used to penetrate the skin and lead the way for prong 1052.

FIG. 51 shows sensor 1050 immediately after it has been driven through channel 1013 by hammer 1054, according to some embodiments. The CU facing fold 1102 of liner 1100 is positioned between cannula unit 1012 and the back side of sensor head 1051. MU facing fold 1101 of liner 1100 is positioned between the front side of sensor head 1051 and motor unit 1011. Contacts 1020 on the motor unit are aligned with the corresponding contacts 1060 on the sensor head.

To finalize the connection of artificial pancreas 1001 to the user, in some embodiments, assistance device 1004 may be pulled away from the patient's skin (FIG. 54). This causes MU facing fold 1101 of liner 1100 to peel from tape 1063, thereby exposing the tape. This also causes CU-facing fold 1102 to push sensor head 1051 towards motor unit 1011, thereby electrically connecting sensor 1050 and motor unit 1011 by means the tape's high conductance in the Z direction. The low conductance in the X and Y directions ensures that the cross-talk between non-corresponding contacts is sufficiently low. Moreover, the system is made less sensitive to cross talk because the signal transferred through contacts 1022 and 1062 is digitized by front end chip 1070, and not transmitted in the more error prone analog form. Tape 1063 may cover contacts 1060 on its one side and contacts 1029 on its other side to seal them in waterproof fashion.

FIG. 55 shows the sensor in its subcutaneously inserted configuration, electrically connected to pump 1001 via the motor unit, according to some embodiments. Artificial pancreas 1000 is thus prepared for operation.

While various inventive embodiments have been described and illustrated herein, those of ordinary skill in the art will readily envision a variety of other means and/or structures for performing the functionality disclosed herein and/or obtaining the results and/or one or more of the advantages described—each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, function, system, article, material, kit, and/or method/step described herein. In addition, any combination of two or more such features, functions, systems, articles, materials, kits, and/or methods/steps, if such features, functions, systems, articles, materials, kits, and/or methods/steps are not mutually inconsistent, is included within the inventive scope of the present disclosure. Some embodiments may be distinguishable from the prior art for specifically lacking one or more features/elements/functionality (i.e., claims directed to such embodiments may include one or more negative limitations).

In addition, and as noted, with respect to the various inventive concepts embodied as one or more methods, the acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, or of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. A patch pump assisting system comprising:
an assisting device including a soft cannula insertion mechanism configured to at least insert a soft cannula in tissue, the device including:
a housing;
a first exit port septum configured within a cup opening;
an exit port well; and
a second exit port septum;
and
a soft cannula having a lumen, and a rigid cannula having a lumen,
wherein:
the soft cannula and rigid cannula each include at least one lateral opening along a length thereof;
the housing is configured for placement on skin of a user for cannula insertion;
prior to insertion, the rigid cannula is positioned within the soft cannula with both cannulas initially traversing a cup septum, and distal ends of the soft cannula and rigid cannula are positioned within the exit port well;
immediately after insertion, the distal ends of the rigid cannula and soft cannula are positioned within and/or below the skin of the user, and corresponding lateral openings thereof are positioned within the exit port well,
and
the rigid cannula is configured for removal from the soft cannula by retraction of the assistance device from the skin of the user.

2. The system of claims 1, wherein the lateral opening of the soft cannula is aligned with the at least one lateral opening of the rigid cannula.

3. The system of claim 1, wherein the cup opening is integral with the housing.

4. The system of claim 1, wherein a sharp end of the rigid cannula protrudes beyond an end of the soft cannula.

5. The system of claim 1, wherein the device further comprises:
a trigger, an inserter spring, an inserter hammer, a cup, and a cup septum, wherein the cup is configured to fit within the cup opening.

6. The system of claim 5, wherein a first end of the soft cannula includes a stopper configured to prevent the soft cannula from moving out of an end of the cup.

7. The system of claim 1, wherein the assisting device includes a cannula bending spring.

8. The system of claim 7, wherein energy stored in the cannula bending spring is released upon separation of the assisting device from a drug delivery system.

9. The system of claim 7, wherein the at least one lateral opening of the soft cannula 1 s aligned with the lateral opening of the rigid cannula.

10. The system of claim 7, wherein a sharp end of the rigid cannula protrudes beyond an end of the soft cannula.

11. The system of claim 7, wherein the energy released by the cannula bending spring moves the rigid cannula from a first position to a second position.

12. The system of claim 11, wherein in the first position is approximately orthogonal relative to a side or portion of the housing, and the second position is approximately parallel to the side or portion of the housing.

13. The system of claim 1, wherein the device further comprises at least one of the following: a trigger, an inserter spring, an inserter hammer, a cup, and a cup septum, wherein the cup is configured to fit within the cup opening.

14. The system of claim 13, wherein a first end of the rigid cannula is rigidly connected to the inserter hammer.

15. The system of claim 13, wherein the cup septum is configured to seal the interior of the cup.

16. The system of claim 13, wherein the cup septum is configured to seal the interior of the cup.

17. The system of claim 13, wherein a first end of the soft cannula includes a stopper configured to prevent the soft cannula from moving out of an end of the cup.

18. The system of claim 17, wherein the stopper is integral with the soft cannula.

19. A drug delivery patch-pump system comprising: a drug-delivery patch pump including a reservoir; a doser device; and the assisting device according to claim 1, wherein: upon filing the reservoir, the pump is configured for priming via the doser, such that, fluid is pumped through an exit port conduit into a filling port well, through the lumen of the rigid cannula, and out the at least one lateral opening of each cannula.

20. A method for inserting a soft cannula for a drug delivery system into tissue of a user, comprising:
triggering a trigger of a cannula insertion mechanism such that one or more safety catches release energy stored in an inserter spring of an inserter mechanism such that:
an inserter hammer of the inserter mechanism is driven in a first direction,
a cup, a cup opening, a cup septum, a rigid cannula and a soft cannula of the inserter mechanism move towards a patient's skin; and
a tip of a rigid cannula punctures the skin establishing a path for a soft cannula;
upon an end of the cup residing on an end of cup septum, the cup placed in the cup opening, and lateral openings of the rigid and the soft cannulas being in fluid communication with an exit port well, and corresponding ends of the rigid cannula and the soft cannula are under the patient's skin, the assisting device is removed while removing the rigid cannula from the lumen of the soft cannula.

21. A patch pump assisting system comprising:
an assisting device including a soft cannula insertion mechanism configured to at least insert a soft cannula in tissue, the device including:
a housing;
a first exit port septum;
an exit port well; and
a second exit port septum;
and
a soft cannula having a lumen, and a rigid cannula having a lumen,
wherein:
the soft cannula and rigid cannula each include at least one lateral opening along a length thereof;
the housing is configured for placement on skin of a user for cannula insertion;
prior to insertion, the rigid cannula is positioned within the soft cannula with distal ends of the soft cannula and rigid cannula positioned within the exit port well;
immediately after insertion, the distal ends of the rigid cannula and soft cannula are positioned within and/or below the skin of the user, and corresponding lateral openings thereof are positioned within the exit port well,
and
the rigid cannula is configured for removal from the soft cannula by retraction of the assistance device from the skin of the user.

* * * * *